(12) United States Patent
Hoegenhaug et al.

(10) Patent No.: US 8,835,604 B2
(45) Date of Patent: *Sep. 16, 2014

(54) ANTIMICROBIAL PEPTIDE VARIANTS AND POLYNUCLEOTIDES ENCODING SAME

(75) Inventors: Hans-Henrik Kristensen Hoegenhaug, Soelleroed Holte (DK); Per Holse Mygind, Vaerloese (DK); Thomas Kruse, Copenhagen (DK); Dorotea Raventos Segura, Rungsted Kyst (DK); Dorthe Hoj Sandvang, Slangerup (DK); Soren Neve, Lyngby (DK)

(73) Assignee: Adenium Biotech Aos, Copenhagen (DK)

( * ) Notice: Subject to any disclaimer, the term of this patent is extended or adjusted under 35 U.S.C. 154(b) by 96 days.

This patent is subject to a terminal disclaimer.

(21) Appl. No.: 13/151,600

(22) Filed: Jun. 2, 2011

(65) Prior Publication Data

US 2011/0306750 A1 Dec. 15, 2011

Related U.S. Application Data

(60) Provisional application No. 61/357,230, filed on Jun. 22, 2010, provisional application No. 61/357,243, filed on Jun. 22, 2010, provisional application No. 61/382,118, filed on Sep. 13, 2010.

(30) Foreign Application Priority Data

Jun. 12, 2010 (EP) .................................. 10165773
Jun. 18, 2010 (EP) .................................. 10166483
Sep. 10, 2010 (EP) .................................. 10176204

(51) Int. Cl.
*A61K 38/00* (2006.01)
*C07H 21/00* (2006.01)
*C12N 15/63* (2006.01)
*C07K 14/435* (2006.01)

(52) U.S. Cl.
CPC ............ *C07K 14/43536* (2013.01); *A61K 38/00* (2013.01)
USPC .......... 530/326; 536/22.1; 435/419; 435/325; 435/320.1; 435/69.1; 435/252.3

(58) Field of Classification Search
None
See application file for complete search history.

(56) References Cited

U.S. PATENT DOCUMENTS

2008/0214450 A1 * 9/2008 Spodsberg ....................... 514/12

FOREIGN PATENT DOCUMENTS

WO WO 2006/097110 A2 9/2006
WO WO 2007/023163 A1 3/2007

OTHER PUBLICATIONS

Andra et al., Biological Chemistry, vol. 390, No. 4, pp. 337-349 (2009).
Ovchinnikova et al., Biochemical and Biophysical Research Communications, vol. 360, No. 1, pp. 156-162 (2007).
Park et al. Biochimica et Biophysica Acta, vol. 1788, No. 9, pp. 1790-1796 (2009).

* cited by examiner

*Primary Examiner* — Karlheinz R Skowronek
*Assistant Examiner* — Lianko Garyu
(74) *Attorney, Agent, or Firm* — Cheryl H. Agris; Agris & Von Natamer, LLP

(57) ABSTRACT

The present invention relates to variants of a parent antimicrobial peptide. The present invention also relates to polynucleotides encoding the variants; nucleic acid constructs, vectors, and host cells comprising the polynucleotides; and methods of using the variants.

19 Claims, No Drawings

ANTIMICROBIAL PEPTIDE VARIANTS AND POLYNUCLEOTIDES ENCODING SAME

REFERENCE TO A SEQUENCE LISTING

This application contains a Sequence L is mg in computer readable form, which is incorporated herein by reference.

BACKGROUND OF THE INVENTION

1. Field of the Invention

The present invention relates to variants of an antimicrobial peptide, polynucleotides encoding the variants, methods of producing the variants, and methods of using the variants.

2. Description of the Related Art

Several classes of antimicrobial peptides (AMPs) have been described in literature, examples of which include defensins and alpha-helical peptides.

The present invention provides variants of an antimicrobial peptide isolated from *Arenicola marina*, and described in WO 2007/023163.

The variant antimicrobial peptides of the present invention exhibit improved antimicrobial activity as compared to the parent antimicrobial peptide. In particular, the variants exhibit improved antimicrobial activity in the presence of serum and blood proteins. Another advantage of the variant peptides of the invention is a reduced protein binding e.g. to serum and blood proteins, which results in an improved bioavailability as compared to the parent antimicrobial peptide.

SUMMARY OF THE INVENTION

The present invention relates to isolated variants of an antimicrobial peptide having the amino acid sequence of SEQ ID NO: 2, comprising an alteration at one or more (several) of positions 1, 2, 3, 4, 5, 6, 7, 8, 9, 10, 11, 12, 13, 15, 17, 19, and 21 of the mature peptide of SEQ ID NO: 2, wherein the variant has antimicrobial activity.

The present invention also relates to isolated polynucleotides encoding the variants; nucleic acid constructs, vectors, and host cells comprising the polynucleotides; and methods of producing the variants.

The present invention also relates to a method of treating a microbial infection using the variants of the invention; and use of variants for manufacturing a medicament for the treatment of a microbial infection.

DETAILED DESCRIPTION OF THE INVENTION

The present invention relates to isolated variants of an antimicrobial peptide having the amino add sequence of SEQ ID NO: 2, comprising an alteration at one or more (several) of positions 1, 2, 3, 4, 5, 6, 7, 8, 9, 10, 11, 12, 13, 15, 17, 19, and 21 of the mature peptide of SEQ ID NO: 2, wherein the variant has antimicrobial activity.

DEFINITIONS

Antimicrobial activity: The term "antimicrobial activity" is defined herein as an activity which is capable of killing or inhibiting growth of microbial cells. In the context of the present invention the term "antimicrobial" is intended to mean that there is a bactericidal and/or a bacteriostatic and/or fungicidal and/or fungistatic effect and/or a virucidal effect, wherein the term "bactericidal" is to be understood as capable of killing bacterial cells. The term "bacteriostatic" is to be understood as capable of inhibiting bacterial growth, i.e. inhibiting growing bacterial cells. The term "fungicidal" is to be understood as capable of killing fungal cells. The term "fungistatic" is to be understood as capable of inhibiting fungal growth, i.e. inhibiting growing fungal cells. The term "virucidal" is to be understood as capable of inactivating virus. The term "microbial cells" denotes bacterial or fungal cells (including yeasts).

In the context of the present invention the term "inhibiting growth of microbial cells" is intended to mean that the cells are in the non-growing state, i.e., that they are not able to propagate.

In a preferred embodiment, the term "antimicrobial activity" is defined as bactericidal and/or bacteriostatic activity. More preferably, "antimicrobial activity" is defined as bactericidal and/or bacteriostatic activity against *Escherichia*, preferably *Escherichia coli*.

For purposes of the present invention, antimicrobial activity may be determined according to the procedure described by Lehrer et al., 1991, *Journal of Immunological Methods* 137(2): 167-174. Alternatively, antimicrobial activity may be determined according to the NCCLS guidelines from CLSI (Clinical and Laboratory Standards Institute; formerly known as National Committee for Clinical and Laboratory Standards).

Peptides having antimicrobial activity may be capable of reducing the number of living cells of *Escherichia coli* (DSM 1576) to 1/100 after 8 hours (preferably after 4 hours, more preferably after 2 hours, most preferably after 1 hour, and in particular after 30 minutes) incubation at 37° C. in a relevant microbial growth substrate at a concentration of 500 micrograms/ml; preferably at a concentration of 250 micrograms/ml; more preferably at a concentration of 100 micrograms/ml; even more preferably at a concentration of 50 micrograms/ml; most preferably at a concentration of 25 micrograms/ml; and in particular at a concentration of 10 micrograms/ml of the peptides having antimicrobial activity.

Peptides having antimicrobial activity may also be capable of inhibiting the outgrowth of *Escherichia coli* (DSM 1576) for 8 hours at 37° C. in a relevant microbial growth substrate, when added in a concentration of 500 micrograms/ml; preferably when added in a concentration of 250 micrograms/ml; more preferably when added in a concentration of 100 micrograms/ml; even more preferably when added in a concentration of 50 micrograms/ml; most preferably when added in a concentration of 10 micrograms/ml; and in particular when added in a concentration of 5 micrograms/ml.

The variant peptides of the present invention have improved antimicrobial activity compared to the antimicrobial peptide of SEQ ID NO: 2. In an embodiment, the variant peptides of the present invention have more than 100% of the antimicrobial activity of the peptide of SEQ ID NO: 2 in the presence of blood serum.

Variant: The term "variant" means a peptide having antimicrobial activity comprising an alteration, i.e., a substitution, insertion, and/or deletion, at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

Mutant: The term "mutant" means a polynucleotide encoding a variant.

Wild-type antimicrobial peptide: The term "wild-type" antimicrobial peptide means an antimicrobial peptide expressed by a naturally occurring microorganism, such as a bacterium, yeast, or filamentous fungus found in nature.

Parent or Parent antimicrobial peptide: The term "parent" or "parent antimicrobial peptide" means an antimicrobial peptide to which an alteration is made to produce the enzyme variants of the present invention. The parent may be a naturally occurring (wild-type) peptide or a variant thereof.

Isolated variant: The term "isolated variant" means a variant that is modified by the hand of man. In one aspect, the variant is at least 1% pure, e.g., at least 5% pure, at least 10% pure, at least 20% pure, at least 40% pure, at least 60% pure, at least 80% pure, and at least 90% pure, as determined by SDS-PAGE.

Substantially pure variant: The term "substantially pure variant" means a preparation that contains at most 10%, at most 8%, at most 6%, at most 5%, at most 4%, at most 3%, at most 2%, at most 1%, and at most 0.5% by weight of other peptide material with which it is natively or recombinantly associated. Preferably, the variant is at least 92% pure, e.g., at least 94% pure, at least 95% pure, at least 96% pure, at least 97% pure, at least 98% pure, at least 99%, at least 99.5% pure, and 100% pure by weight of the total peptide material present in the preparation. The variants of the present invention are preferably in a substantially pure form. This can be accomplished, for example, by preparing the variant by well known recombinant methods or by classical purification methods.

Mature peptide: The term "mature peptide" means a peptide in its final form following translation and any post-translational modifications, such as N-terminal processing, C-terminal truncation, glycosylation, phosphorylation, etc.

Mature peptide coding sequence: The term "mature peptide coding sequence" means a polynucleotide that encodes a mature peptide having antimicrobial activity.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment)

Fragment: The term "fragment" means a peptide having one or more (several) amino acids deleted from the amino and/or carboxyl terminus of a mature peptide; wherein the fragment has antimicrobial activity. In one aspect, a fragment contains at least 15 amino acid residues, e.g., at least 17 and at least 19 amino acid residues (e.g., amino acids 1 to 20 of SEQ ID NO: 2).

Subsequence: The term "subsequence" means a polynucleotide having one or more (several) nucleotides deleted from the 5'- and/or 3'-end of a mature peptide coding sequence; wherein the subsequence encodes a fragment having antimicrobial activity.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded peptide) or may encode peptides having altered amino acid sequences. An allelic variant of a peptide is a peptide encoded by an allelic variant of a gene.

Isolated polynucleotide: The term "isolated polynucleotide" means a polynucleotide that is modified by the hand of man. In one aspect, the isolated polynucleotide is at least 1% pure, e.g., at least 5% pure, at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Substantially pure polynucleotide: The term "substantially pure polynucleotide" means a polynucleotide preparation free of other extraneous or unwanted nucleotides and in a form suitable for use within genetically engineered peptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5'- and 3'-untranslated regions, such as promoters and terminators. It is preferred that the substantially pure polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Coding sequence: The term "coding sequence" means a polynucleotide, which directly specifies the amino acid sequence of its peptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" means all components necessary for the expression of a polynucleotide encoding a variant of the present invention. Each control sequence may be native or foreign to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Conventions for Designation of Variants

For purposes of the present invention, the mature peptide disclosed in SEQ ID NO: 2 is used to determine the corresponding amino acid residue in another antimicrobial peptide. The amino acid sequence of another antimicrobial peptide is aligned with the mature peptide disclosed in SEQ ID NO: 2, and based on the alignment, the amino acid position number corresponding to any amino acid residue in the mature peptide disclosed in SEQ ID NO: 2 is determined using the Needleman-Wunsch algorithm (Needleman and Wunsch, 1970, *J. Mol, Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later.

Identification of the corresponding amino acid residue in another antimicrobial peptide can be confirmed by an alignment of multiple peptide sequences using "ClustalW" (Larkin et al., 2007, *Bioinformatics* 23: 2947-2948).

When the other enzyme has diverged from the mature peptide of SEQ ID NO: 2 such that traditional sequence-based comparison fails to detect their relationship (Lindahl and Elofsson, 2000, *J. Mol. Biol.* 295: 613-615), other pairwise sequence comparison algorithms be used. Greater sensitivity in sequence-based searching can be attained using search programs that utilize probabilistic representations of peptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the peptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the peptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementations of these algorithms can additionally be utilized to query structure databases with a structure of interest in order to discover possible structural homologs (e.g., Holm and Park, 2000, *Bioinformatics* 16: 566-567).

In describing the antimicrobial peptide variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine with alanine at position 226 is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G-K-A |

Multiple alterations. Variants comprising multiple alterations are separated by addition marks ("+"), e.g., "Arg170Tyr+Gly195Glu" or "R170Y+G195E" representing a substitution of tyrosine and glutamic acid for arginine and glycine at positions 170 and 195, respectively.

Different substitutions. Where different substitutions can be introduced at a position, the different substitutions are separated by a comma, e.g., "Arg170Tyr,Glu" or "R170Y,E" represents a substitution of arginine with tyrosine or glutamic acid at position 170. Thus, "Tyr167Gly,Ala+Arg170Gly,Ala" or "Y167G,A+R170G,A" designates the following variants: "Tyr167Gly+Arg170Gly", "Tyr167Gly+Arg 170Ala", "Tyr167Ala+Arg170Gly", and "Tyr167Ala+Arg170Ala".

Parent Antimicrobial Peptides

The parent antimicrobial peptide is (a) a peptide with at least 60% sequence identity with the mature peptide of SEC) ID NO: 2; (b) a peptide encoded by a polynucleotide that hybridizes under medium stringency conditions with (i) the mature peptide coding sequence of SEQ ID NO: 1, or (ii) the full-length complementary strand of (i); or (c) a peptide encoded by a polynucleotide with at least 60% sequence identity with the mature peptide coding sequence of SEQ ID NO: 1.

In a first aspect, the parent has a sequence identity to the mature peptide of SEQ ID NO: 2 of at least 60%, e.g., at least 65%, at least 70%, at least 75%, at least 80%, at least 85%, at least 90%, at least 95%, at least 96%, at least 97%, at least 98%, at least 99%, or 100%, which have antimicrobial activity. In one aspect, the amino acid sequence of the parent differs by no more than ten amino acids, e.g., by five amino acids, by four amino acids, by three amino acids, by two amino acids, and by one amino acid from the mature peptide of SEQ ID NO: 2.

The parent preferably comprises or consists of the amino acid sequence of SEQ ID NO: 2.

In an embodiment, the parent is a fragment of the peptide of SEQ ID NO: 2 containing at least 15 amino acid residues, e.g., at least 17 and at least 19 amino acid residues.

In another embodiment, the parent is an allelic variant of the peptide of SEQ ID NO: 2.

In a second aspect, the parent peptide is encoded by a polynucleotide that hybridizes under medium stringency conditions, medium-high stringency conditions, high stringency conditions, or very high stringency conditions with (i) the mature peptide coding sequence of SEQ ID NO: 1, or (ii) the full-length complementary strand of (i) (J. Sambrook, E. F. Fritsch, and T. Maniatis, 1989, *Molecular Cloning, A Laboratory Manual,* 2d edition, Cold Spring Harbor, New York).

The polynucleotide of SEQ ID NO: 1 or a subsequence thereof, as well as the amino acid sequence of SEQ ID NO: 2 or a fragment thereof, may be used to design nucleic acid probes to identify and clone DNA encoding a parent from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, or at least 35 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other organisms may be screened for DNA that hybridizes with the probes described above and encodes a parent. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or a subsequence thereof, the carrier material is used in a Southern blot.

For purposes of the present invention, hybridization indicates that the polynucleotide hybridizes to a labeled nucleotide probe corresponding to the polynucleotide shown in SEQ ID NO: 1, its complementary strand, or a subsequence thereof, under low to very high stringency conditions. Molecules to which the probe hybridizes can be detected using, for example, X-ray film or any other detection means known in the art.

In one aspect, the nucleic acid probe is SEQ ID NO: 1.

For long probes of at least 60 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), 50° C. (low stringency), 55° C. (medium stringency), 60° C. (medium-high stringency), 65° C. (high stringency), or 70° C. (very high stringency).

For short probes that are about 15 nucleotides to about 60 nucleotides in length, stringency conditions are defined as prehybridization and hybridization at about 5° C. to about 10° C. below the calculated $T_m$, using the calculation according to Bolton and McCarthy (1962, *Proc. Natl. Acad. Sci. USA* 48: 1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

In a third aspect, the parent is encoded by a polynucleotide with a sequence identity to the peptide coding sequence of SEQ ID NO: 1 of at least 60%, e.g., at least 65%, at least 70%, at least 75%, at least 80%, at least 85%, at least 90%, at least 95%, at least 96%, at least 97%, at least 98%, at least 99%, or 100%, which encodes a peptide having antimicrobial activity.

The parent may be obtained from microorganisms of any genus. For purposes of the present invention, the term "obtained from" as used herein in connection with a given source shall mean that the parent encoded by a polynucleotide is produced by the source or by a cell which the polynucleotide from the source has been inserted. In one aspect, the parent is secreted extracellularly.

The parent may be a bacterial antimicrobial peptide. For example, the parent may be a gram-positive bacterial peptide such as a *Bacillus, Clostridium, Enterococcus, Geobacillus, Lactobacillus, Lactococcus, Oceanobacillus, Staphylococ-* cus, *Streptococcus*, or *Streptomyces* antimicrobial peptide, or a gram-negative bacterial peptide such as a *Campylobacter, E. coli, Flavobacterium, Fusobacterium, Helicobacter, Ilyobacter, Neisseria, Pseudomonas, Salmonella*, or *Ureaplasma* antimicrobial peptide.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* antimicrobial peptide.

In another aspect, the parent is a *Streptococcus equisimilis, Streptococcus pyogenes, Streptococcus uberis*, or *Streptococcus equi* subsp. *Zooepidetnicus* antimicrobial peptide.

In another aspect, the parent is a *Streptomyces achromogenes, Streptomyces avermitilis, Streptomyces coelicolor, Streptomyces griseus*, or *Streptomyces lividans* antimicrobial peptide.

The parent may be a fungal antimicrobial peptide. For example, the parent may be a yeast antimicrobial peptide such as a *Candida, Kluyveromyces, Pichia, Saccharomyces, Schizosaccharomyces*, or *Yarrowia* antimicrobial peptide. For example, the parent may be a filamentous fungal antimicrobial peptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Colynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophylium, Scytalidium, Talaromyces, Thermoascus, Thielavia, Tolypocladium, Trichoderma, Trichophaea, Volvariella*, or *Xylaria* antimicrobial peptide.

In another aspect, the parent is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* antimicrobial peptide.

In another aspect, the parent is an *Acremonium cellutolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride* antimicrobial peptide.

In another aspect, the parent is an *Arenicola marina* antimicrobial peptide, e.g., the antimicrobial peptide of SEQ ID NO: 2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. The polynucleotide encoding a parent may then be derived by similarly screening a genomic or cDNA library of another microorganism or mixed DNA sample. Once a polynucleotide encoding a parent has been detected with a probe(s), the polynucleotide may be isolated or cloned by utilizing techniques that are known to those of ordinary skill in the art (see, e.g., Sambrook et al., 1989, supra).

The parent may be a hybrid peptide in which a portion of one peptide is fused a N-terminus or the C-terminus of a portion of another peptide.

The parent also may be a fused peptide or cleavable fusion peptide in which one peptide is fused at the N-terminus or the C-terminus of another peptide. A fused peptide is produced by fusing a polynucleotide encoding one peptide to a polynucleotide encoding another peptide. Techniques for producing fusion peptides are known in the art, and include ligating the coding sequences encoding the peptides so that they are in frame and that expression of the fused peptide is under control of the same promoter(s) and terminator. Fusion proteins may also be constructed using intein technology in which fusions are created post-translationally (Cooper et al., 1993, *EMBO J.* 12: 2575-2583; Dawson et al., 1994. *Science* 266: 776-779).

A fusion peptide can further comprise a cleavage site between the two peptides. Upon secretion of the fusion protein, the site is cleaved releasing the two peptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Preparation of Variants

The present invention also relates to methods for obtaining a variant having antimicrobial activity, comprising: (a) introducing into a parent antimicrobial peptide a substitution at one or more several) corresponding to positions 1, 2, 3, 4, 5, 6, 7, 8, 9, 10, 11, 12, 13, 15, 17, 19, and 21 of the mature peptide of SEQ ID NO: 2, wherein the variant has antimicrobial activity; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (several) mutations are created at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests at the plasmid and the oligonucleotide is the same, permitting sticky ends of the plasmid and insert to ligate to one another. See, e.g., Scherer and Davis, 1979, *Proc. Natl. Acad. Sci, USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a peptide of interest. Gene synthesis can be performed utilizing a number of techniques, such as the multiplex microchip-based technology described by Tian et al. (2004, *Nature* 432: 1050-1054) and similar technologies wherein oligionucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Aced. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized peptides expressed by host cells (Ness et al., 1999, *Nature Biotechnology* 17: 893-896). Mutagenized DNA molecules that encode active peptides can be recovered from the host cells and rapidly sequenced using standard methods in the art. These methods allow the rapid determination of the importance of individual amino acid residues in a peptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Variants

The present invention also provides variants of a parent antimicrobial peptide comprising a substitution at one or more (several) positions corresponding to positions 1, 2, 3, 4, 5, 6, 7, 8, 9, 10, 11, 12, 13, 15, 17, 19, and 21 (preferably positions 1, 2, 4, 5, 6, 8, 9, 12, 13, 15, 17, and 21; more preferably positions 4, 5, 6, 8, 9, 12, 13, 15, and 17), wherein the variant has antimicrobial activity. In an embodiment, the variant has improved antimicrobial activity compared to the peptide of SEQ ID NO: 2; preferably in the presence of blood or serum. In another embodiment, the variant exhibit less protein binding compared to the peptide of SEQ ID NO: 2. Preferably, the variant antimicrobial peptides exhibit at the most 99% serum protein binding. The variant antimicrobial peptides also exhibit improved bioavailability. Preferably the subcutaneous bioavailably is at least 30%, more preferably at least 40%, even more preferably at least 50%, and most preferably at least 60%.

In an embodiment, the variant has sequence identity of at least 60%, e.g., at least 65%, at least 70%, at least 75%, at least 80%, at least 85%, at least 90%, at least 95%, at least 96%, at least 97%, at least 98%, or at least 99%, but less than 100%, to the amino acid sequence of the parent antimicrobial peptide.

In another embodiment, the variant has at least 60%, e.g., at least 65%, at least 70%, at least 75%, at least 80%, at least 85%, at least 90%, at least 95%, such as at least 96%, at least 97%, at least 98%, and at least 99%, but less than 100%, sequence identity with the mature peptide of SEQ ID NO: 2.

In one aspect, the number of substitutions in the variants of the present invention is 1-11, e.g., 1-10 substitutions, 1-9 substitutions, 1-8 substitutions, 1-7 substitutions, 1-6 substitutions, 1-5 substitutions, 1-4 substitutions, 1-3 substitutions and 1-2 substitutions.

In one aspect, the variant comprises or consists of the amino acid sequence shown as SEQ ID NO: 3 to SEQ ID NO: 548.

The term "SEQ ID NO: 3 to SEQ ID NO: 548" is intended to mean any one of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, SEQ ID NO: 364, SEQ ID NO: 365, SEQ ID NO: 366, SEQ ID NO: 367, SEQ ID NO: 368, SEQ ID NO: 369, SEQ ID NO: 370, SEQ ID NO: 371, SEQ ID NO: 372, SEQ ID NO: 373, SEQ ID NO: 374, SEQ ID NO: 375, SEQ ID NO: 376, SEQ ID NO: 377, SEQ ID NO: 378, SEQ ID NO: 379, SEQ ID NO: 380, SEQ ID NO: 381, SEQ ID NO: 382, SEQ ID NO: 383, SEQ ID NO: 384, SEQ ID NO: 385, SEQ ID NO: 386, SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, SEQ ID NO: 406, SEQ ID NO: 407, SEQ ID NO: 408, SEQ ID NO: 409, SEQ ID NO: 410, SEQ ID NO: 411, SEQ ID NO: 412, SEQ ID NO: 413, SEQ ID NO: 414, SEQ ID NO: 415, SEQ ID NO: 416, SEQ ID NO: 417, SEQ ID NO: 418, SEQ ID NO: 419, SEQ ID NO: 420, SEQ ID NO: 421, SEQ ID NO: 422, SEQ ID NO: 423, SEQ ID NO: 424, SEQ ID NO: 425, SEQ ID NO: 426, SEQ ID NO: 427, SEQ ID NO: 428, SEQ ID NO: 429, SEQ ID NO: 430, SEQ ID NO: 431, SEQ ID NO: 432, SEQ ID NO: 433, SEQ ID NO: 434, SEQ ID NO: 435, SEQ ID NO: 436, SEQ ID NO: 437, SEQ ID NO: 438, SEQ ID NO: 439, SEQ ID NO: 440, SEQ ID NO: 441, SEQ ID NO: 442, SEQ ID NO: 443, SEQ ID NO: 444, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, SEQ ID NO: 455, SEQ ID NO: 456, SEQ ID NO: 457, SEQ ID NO: 458, SEQ ID NO: 459, SEQ ID NO: 460, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, SEQ ID NO: 471, SEQ ID NO: 472, SEQ ID NO: 473, SEQ ID NO: 474, SEQ ID NO: 475, SEQ ID NO: 476, SEQ ID NO: 477, SEQ ID NO: 478, SEQ ID NO: 479, SEQ ID NO: 480, SEQ ID NO: 481, SEQ ID NO: 482, SEQ ID NO: 483, SEQ ID NO: 484, SEQ ID NO: 485, SEQ ID NO: 486, SEQ ID NO: 487, SEQ ID NO: 488, SEQ ID NO: 489, SEQ ID NO: 490, SEQ ID NO: 491, SEQ ID NO: 492, SEQ ID NO: 493, SEQ ID NO: 494, SEQ ID NO: 495, SEQ ID NO: 496, SEQ ID NO: 497, SEQ ID NO: 498, SEQ ID NO: 499, SEQ ID NO: 500, SEQ ID NO: 501, SEQ ID NO: 502, SEQ ID NO: 503, SEQ ID NO: 504, SEQ ID NO: 505, SEQ ID NO: 506, SEQ ID NO: 507, SEQ ID NO: 508, SEQ ID NO: 509, SEQ ID NO: 510, SEQ ID NO: 511, SEQ ID NO: 512, SEQ ID NO: 513, SEQ ID NO: 514, SEQ ID NO: 515, SEQ ID NO: 516, SEQ ID NO: 517, SEQ ID NO: 518, SEQ ID NO: 519, SEQ ID NO: 520, SEQ ID NO: 521, SEQ ID NO: 522, SEQ ID NO: 523, SEQ ID NO: 524, SEQ ID NO: 525, SEQ ID NO: 526, SEQ ID NO: 527, SEQ ID NO: 528, SEQ ID NO: 529, SEQ ID NO: 530, SEQ ID NO: 531, SEQ ID NO: 532, SEQ ID NO: 533, SEQ ID NO: 534, SEQ ID NO: 535, SEQ ID NO: 536, SEQ ID NO: 537, SEQ ID NO: 538, SEQ ID NO: 539, SEQ ID NO: 540, SEQ ID NO: 541, SEQ ID NO: 542, SEQ ID NO: 543, SEQ ID NO: 544, SEQ ID NO: 545, SEQ ID NO: 546, SEQ ID NO: 547, and/or SEQ ID NO: 548.

In one aspect, a variant comprises a substitution at one or more (several) positions corresponding to positions 1, 2, 3, 4, 5, 6, 7, 8, 9, 10, 11, 12, 13, 15, 17, 19, and 21; preferably positions 1, 2, 4, 5, 6, 8, 9, 12, 13, 15, 17, and 21; and more preferably positions 4, 5, 6, 8, 9, 12, 13, 15, and 17. In another aspect, a variant comprises a substitution at two positions corresponding to any of positions 1, 2, 3, 4, 5, 6, 7, 8, 9, 10, 11, 12, 13, 15, 17, 19, and 21; preferably positions 1, 2, 4, 5, 6, 8, 9, 12, 13, 15, 17, and 21; and more preferably positions 4, 8, 9, 12, 13, 15, and 17. In another aspect, a variant comprises a substitution at three positions corresponding to any of positions 1, 2, 3, 4, 5, 6, 7, 8, 9, 10, 11, 12, 13, 15, 17, 19, and 21; preferably positions 1, 2, 4, 5, 6, 8, 9, 12, 13, 15, 17, and 21; and more preferably positions 4, 5, 6, 8, 9, 12, 13, 15, and 17. In another aspect, a variant comprises a substitution at four positions corresponding to any of positions 1, 2, 3, 4, 5, 6, 7, 8, 9, 10, 11, 12, 13, 15, 17, 19, and 21; preferably positions 1, 2, 4, 5, 6, 8, 9, 12, 13, 15, 17, and 21; and more preferably positions 4, 5, 6, 8, 9, 12, 13, 15, and 17. In another aspect, a variant comprises a substitution at five positions corresponding to any of positions 1, 2, 3, 4, 5, 6, 7, 8, 9, 10, 11, 12, 13, 15, 17, 19, and 21; preferably positions 1, 2, 4, 5, 6, 8, 9, 12, 13, 15, 17, and 21; and more preferably positions 4, 5, 6, 8, 9, 12, 13, 15, and 17. In another aspect, a variant comprises a substitution at six positions corresponding to any of positions 1, 2, 3, 4, 5, 6, 7, 8, 9, 10, 11, 12, 13, 15, 17, 19, and 21; preferably positions 1, 2, 4, 5, 6, 8, 9, 12, 13, 15, 17, and 21; and more preferably positions 4, 5, 6, 8, 9, 12, 13, 15, and 17.

In another aspect, the variant comprises the substitution G1A,D,F,H,I,K,M,Q,R,S,T,V,W,Y of the mature peptide of SEQ ID NO: 2. In another aspect, the variant comprises the substitution F2A,G,H,I,L,M,P,S,V,W,Y of the mature peptide of SEQ ID NO: 2. In another aspect, the variant comprises the substitution C3L of the mature peptide of SEQ ID NO: 2. In another aspect, the variant comprises the substitution W4A,E,F,G,I,L,M,N,Q,S,T,V,Y of the mature peptide of SEQ ID NO: 2. In another aspect, the variant comprises the substitution Y5E,F,G,H,K,N,R,S,W of the mature peptide of SEQ ID NO: 2. In another aspect, the variant comprises the substitution V6A,C,E,F,G,H,I,L,M,N,Q,R,S,T,W,Y of the mature peptide of SEQ ID NO: 2. In another aspect, the variant comprises the substitution C7V of the mature peptide of SEQ ID NO: 2. In another aspect, the variant comprises the substitution V8A,F,G,H,I,L,N,S,T,W,Y of the mature peptide of SEQ ID NO: 2. In another aspect, the variant comprises the substitution Y9A,D,F,G,H,I,K,M,Q,R,S,T,V,W of the mature peptide of SEQ ID NO: 2. In another aspect, the variant comprises the substitution R10K,P,S,T of the mature peptide of SEQ ID NO: 2. In another aspect, the variant comprises the substitution N11A,G,H,Q,R,S,Y of the mature peptide of SEQ ID NO: 2. In another aspect, the variant comprises the substitution G12A,D,E,F,H,K,N,R,S,Y of the mature peptide of SEQ ID NO: 2. In another aspect, the variant comprises the substitution V13A,C,F,G,H,K,L,P,Q,R,S,T,W,Y of the mature peptide of SEQ ID NO: 2. In another aspect, the variant comprises the substitution V15A,C,F,G,H,I,K,L,M,N,P,Q,R,S,T,W,Y of the mature peptide of SEQ ID NO: 2. In another aspect, the variant comprises the substitution Y17C,F,G,H,I,K,L,M,N,Q,R,S,T,V,W of the mature peptide of SEQ ID NO: 2. In another aspect, the variant comprises the substitution R19D,H,K,M,T,Y of the mature peptide of SEQ ID NO: 2. In another aspect, the variant comprises the substitution N21A,C,F,G,H,I,K,L,M,P,O,R,S,T,W,Y of the mature peptide of SEQ ID NO: 2.

In one aspect, the variant comprises a substitution at position 1. In another aspect, the amino acid at position 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Asp, Phe, His, Ile, Lys, Met, Gln, Arg, Ser, Thr, Val, Trp, or Tyr. In another aspect, the variant comprises the substitution G1A,D,F,H,I,K,M,Q,R,S,T,V,W,Y of the mature peptide of SEQ ID NO: 2.

In one aspect, the variant comprises a substitution at position 2. In another aspect, the amino acid at position 2 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Gly, His, Ile, Leu, Met, Pro, Ser, Val, Trp, or Tyr. In another aspect, the variant comprises the substitution F2A,G,H,I,L,M,P,S,V,W,Y of the mature peptide of SEQ ID NO: 2.

In one aspect, the variant comprises a substitution at position 3. In another aspect, the amino acid at position 3 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant comprises the substitution C3L of the mature peptide of SEQ ID NO: 2.

In one aspect, the variant comprises a substitution at position 4. In another aspect, the amino acid at position 4 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Glu, Phe, Gly, Ile, Leu, Met, Asn, Gln, Ser, Thr, Val, or Tyr. In another aspect, the variant comprises the substitution W4A,E,F,G,I,L,M,N,Q,S,T,V,Y of the mature peptide of SEQ ID NO: 2.

In another aspect, the variant comprises a substitution at position 5. In another aspect, the amino acid at position 5 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu, Phe, Gly, His, Lys, Asn, Arg, Ser, or Trp. In another aspect, the variant comprises the substitution Y5E,F,G,H,K,N,R,S,W of the mature peptide of SEQ ID NO: 2.

In another aspect, the variant comprises a substitution at position 6. In another aspect, the amino acid at position 6 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Cys, Glu, Phe, Gly, His, Ile, Leu, Met, Asn, Gln, Arg, Ser, Thr, Trp, or Tyr. In another aspect, the variant comprises the substitution V6A,C,E,F,G,H,I,L,M,N,Q,R,S,T,W,Y of the mature peptide of SEQ ID NO: 2.

In one aspect, the variant comprises a substitution at position 7, In another aspect, the amino acid at position 7 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the variant comprises the substitution C7V of the mature peptide of SEQ ID NO: 2.

In another aspect, the variant comprises a substitution at position 8. In another aspect, the amino acid at position 8 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Phe, Gly, His, Ile, Leu, Asn, Ser, Thr, Trp, or Tyr. In another aspect, the variant comprises the substitution V8A,F,G,H,I,L,N,S,T,W,Y of the mature peptide of SEQ ID NO: 2.

In another aspect, the variant comprises a substitution at position 9. In another aspect, the amino acid at position 9 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Asp, Phe, Gly, His, Ile, Lys, Met, Gln, Arg, Ser, Thr, Val, or Trp. In another aspect, the variant comprises the substitution Y9A,D,F,G,H,I,K,M,Q,R,S,T,V,W of the mature peptide of SEQ ID NO: 2.

In one aspect, the variant comprises a substitution at position 10. In another aspect, the amino acid at position 10 is substituted with Ala, Arg, Asn, Asp, Cys, Gln, Glu, Gly, His, Ile, Leu, Lys, Met, Phe, Pro, Ser, Thr, Trp, Tyr, or Val, preferably with Lys, Pro, Ser, or Thr. In another aspect, the variant comprises the substitution R10K,P,S,T of the mature peptide of SEQ ID NO: 2.

In one aspect, the variant comprises a substitution at position 11. In another aspect, the amino acid at position 11 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Gly, His, Gln, Arg, Ser, or Tyr. In another aspect, the variant comprises the substitution N11A,G,H,Q,R,S,Y of the mature peptide of SEQ ID NO: 2.

In another aspect, the variant comprises a substitution at position 12. In another aspect, the amino acid at position 12 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Asp, Glu, Phe, His, Lys, Asn, Arg, Ser, or Tyr. In another aspect, the variant comprises the substitution G12A,D,E,F,H,K,N,R,S,Y of the mature peptide of SEQ ID NO: 2.

In one aspect, the variant comprises a substitution at position 13. In another aspect, the amino acid at position 13 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Cys, Phe, Gly, His, Lys, Leu, Pro, Gln, Arg, Ser, Thr, Trp, or Tyr. In another aspect, the variant comprises the substitution V13A,C,F,G,H,K,L,P,Q,R,S,T,W,Y of the mature peptide of SEQ ID NO: 2.

In another aspect, the variant comprises a substitution at position 15. In another aspect, the amino acid at position 15 is substituted with Ala, Arg, Asn, Asp, Cys, Glu, Gly, His, Ile, Leu, Lys, Met, Phe, Pro, Ser, Thr, Trp, Tyr, or Val, preferably with Ala, Cys, Phe, Gly, His, Ile, Lys, Leu, Met, Asn, Pro, Gln, Arg, Ser, Thr, Trp, or Tyr. In another aspect, the variant comprises the substitution V15A,C,F,G,H,I,K,L,M,N,P,Q,R,S,T,W,Y of the mature peptide of SEQ ID NO: 2.

In one aspect, the variant comprises a substitution at position 17. In another aspect, the amino acid at position 17 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys, Phe, Gly, His, Ile, Lys, Leu, Met, Asn, Gln, Arg, Ser, Thr, Val, or Trp. In another aspect, the variant comprises the substitution Y17C,F,G,H,I,K,L,M,N,Q,R,S,T,V,W of the mature peptide of SEQ ID NO: 2.

In one aspect, the variant comprises a substitution at position 19. In another aspect, the amino acid at position 19 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp, His, Lys, Met, Thr, or Tyr. In another aspect, the variant comprises the substitution R19D,H,K,M,T,Y of the mature peptide of SEQ ID NO: 2.

In one aspect, the variant comprises a substitution at position 21. In another aspect, the amino acid at position 21 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Cys, Phe, Gly, His, Ile, Lys, Leu, Met, Pro, Gln, Arg, Ser, Thr, Trp, or Tyr. In another aspect, the variant comprises the substitution N21A,C,F,G,H,I,K,L,M,P,Q,R,S,T,W,Y of the mature peptide of SEQ ID NO: 2.

In another aspect, the variant comprises a substitution at positions corresponding to positions 5 and 17, such as those described above.

In another aspect, the variant comprises substitutions at positions corresponding to positions 5 and 9, such as those described above.

In another aspect, the variant comprises substitutions at positions corresponding to positions 5 and 15, such as those described above.

In another aspect, the variant comprises substitutions at positions corresponding to positions 17 and 9, such as those described above.

In another aspect, the variant comprises substitutions at positions corresponding to positions 17 and 15, such as those described above.

In another aspect, the variant comprises substitutions at positions corresponding to positions 9 and 15, such as those described above.

In another aspect, the variant comprises substitutions at positions corresponding to positions 5, 17, and 9, such as those described above.

In another aspect, the variant comprises substitutions at positions corresponding to positions 5, 17, and 15, such as those described above.

In another aspect, the variant comprises substitutions at positions corresponding to positions 5, 9, and 15, such as those described above.

In another aspect, the variant comprises substitutions at positions corresponding to positions 17, 9, and 15, such as those described above.

In another aspect, the variant comprises substitutions at positions corresponding to positions 5, 17, 9, and 15, such as those described above.

In another aspect, the variant comprises one or more (several) substitutions selected from the group consisting of
G1D, G1F, G1H, G1I, G1K, G1M, G1Q, G1R, G1S, G1T, G1V, G1W, G1Y,
F2A, F2G, F2H, F2I, F2L, F2M, F2P, F2S, F2V, F2W, F2Y, C3L,
W4A, W4E, W4F, W4G, W4I, W4L, W4M, W4N, W4Q, W4S, W4T, W4V, W4Y,
Y5E, Y5F, Y5G, Y5H, Y5K, Y5N, Y5R, Y5S, Y5W,
V6A, V6C, V6E, V6F, V6G, V6H, V6I, V6L, V6M, V6N, V6Q, V6R, V6S, V6T, V6W, V6Y,
C7V,
V8A, V8F, V8G, V8H, V8I, V8L, V8N, V8S, V8T, V8W, V8Y,
Y9A, Y9D, Y9F, Y9G, Y9H, Y9I, Y9K, Y9M, Y9Q, Y9R, Y9S, Y9T, Y9V, Y9W,
R19K, R10P, R10S, R10T,
N11A, N11G, N11H, N11O, N11R, N11S, N11Y,
G12A, G12D, G12E, G12F, G12H, G12K, G12N, G12R, G12S, G12Y,
V13A, V13C, V13F, V13G, V13H, V13K, V13L, V13P, V13Q, V13R, V13S, V13T, V13W, V13Y,
V15A, V15C, V15F, V15G, V15H, V15I, V15K, V15L, V15M, V15N, V15P, V15Q, V15R, V15S, V15T, V15W, V15Y,
Y17C, Y17F, Y17G, Y17H, Y17I, Y17K, Y17L, Y17M, Y17N, Y17Q, Y17R, Y17S, Y17T, Y17V, Y17W,
R19D, R19H, R19K, R19M, R19T, R19Y,
N21A, N21C, N21F, N21G, N21H, N21I, N21K, N21L, N21M, N21P, N21Q, N21R, N21S, N21T, N21W, and N21Y; preferably
W4A, Y5H, Y5N, Y5R, V6A, V6F, V8A, Y9K, Y9R, G12R, G12K, V13A V15I, V15S, and Y17H.

In another aspect, the variant comprises the substitutions Y5N+Y17H of the mature peptide of SEQ ID NO: 2.

In another aspect, the variant comprises the substitutions Y5N+Y9R of the mature peptide of SEQ ID NO: 2.

In another aspect, the variant comprises the substitutions Y5N+Y9K of the mature peptide of SEQ ID NO: 2.

In another aspect, the variant comprises the substitutions Y17H+Y9R of the mature peptide of SEQ ID NO: 2.

In another aspect, the variant comprises the substitutions Y17H+Y9K of the mature peptide of SEQ ID NO: 2.

In another aspect, the variant comprises the substitutions Y5N+Y17H+Y9R of the mature peptide of SEQ ID NO: 2.

In another aspect, the variant comprises the substitutions Y5N+Y17H+Y9K of the mature peptide of SEQ ID NO: 2.

In another aspect, the variant comprises the substitutions Y5N+V6A+Y9K or V8A+Y9R+V13A or Y5N+Y9R+Y17H or Y9K+V15S or W4A+Y5R+Y9K or Y5N+G12R+Y17H or Y5N+V6F+Y17H or Y5N+V15I+Y17H or Y5H+V8A+Y9R or Y5N+G12K+Y17H of the mature peptide of SEQ ID NO: 2.

Essential amino acids in a parent can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for antimicrobial activity to identify amino acid residues that are critical to the activity of the molecule. See also, Hilton et al., 1996, *J. Biol. Chem.* 271: 4699-4708. The identities of essential amino acids can also be inferred from analysis of identities with peptides that are related to the parent.

Polynucleotides

The present invention also relates to isolated polynucleotides that encode any of the variants of the present invention.

Nucleic Acid Constructs

The present invention also relates to nucleic acid constructs comprising a polynucleotide encoding a variant of the present invention operably linked to one or more (several) control sequences that direct the expression of the coding sequence in a suitable host cell under conditions compatible with the control sequences.

A polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, which is recognized by a host cell for expression of the polynucleotide. The promoter sequence contains transcriptional control sequences that mediate the expression of the variant. The promoter may be any nucleic acid sequence that shows transcriptional activity in the host cell including mutant, truncated, and hybrid promoters, and may be obtained from genes encoding extracellular or intracellular peptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (Villa-Kamaroff at al., 1978, *Proc. Natl. Acad. Sci. USA* 75: 3727-3731), as well as the tac promoter (DeBoer at al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra.

Examples of suitable promoters for directing the transcription of the nucleic acid constructs of the present invention in a filamentous fungal host cell are the promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dada (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in *Aspergilli* in which the untranslated leader has been replaced by an untranslated leader from a gene encoding triose phosphate isomerase in *Aspergilli*; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate, kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the variant. Any terminator that is functional in the host cell may be used.

Preferred terminators for filamentous fungal host cells are obtained from the genes for *Aspergillus nidulans* anthraniiate synthase, *Aspergillus niger* alpha-glucosidase, *Aspergillus niger* glucoamylase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5-terminus of the polynucleotide encoding the variant. Any leader sequence that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1). *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH21GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding region naturally linked in translation reading frame with the segment of the coding region that encodes the variant. Alternatively, the 5'-end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the variant. However, any signal peptide coding region that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding region that encodes a propeptide positioned at the N-terminus of a variant. The resultant peptide is known as a proenzyme or propeptide (or a zymogen in some cases). A propeptide is generally inactive and can be converted to an active peptide by catalytic or autocatalytic cleavage of the propeptide from the propeptide. The propeptide coding region may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide regions are present at the N-terminus of a variant, the propeptide region is positioned next to the N-terminus of the variant and the signal peptide region is positioned next to the N-terminus of the propeptide region.

It may also be desirable to add regulatory sequences that allow the regulation of the expression of the variant relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about the expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus licheniformis* or *Bacillus subtilis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook at al., 1989, supra) to obtain substantially pure variants.

Host Cells

The present invention also relates to recombinant host cells, comprising a polynucleotide of the present invention operably linked to one or more (several) control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any gram-positive or gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma*.

The bacterial host cell may be any *Bacillus* cell, including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell, including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-2070, by electroporation (see, e.g., Buckley et al., 1999, *Appl. Environ. Microbiol,* 65: 3800-3804) or by conjugation (see, e.g., Clewell, 1981, *Microbiol. Rev,* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi,* 8th edition, 1995, CAB International, University Press, Cambridge, UK).

The fungal host cell may be a yeast cell, "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series No. 9,* 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergilius, Aureobasidium, Bjerkandera, Ceriporlopsis, Chrysosporium, Coprinus, Coriolus, Cryptococcus, Filibasidium, Fusarium, Humicola, Magnaporthe, Mucor, Myceliophthora, Neocallimastlx, Neurospora, Paecilomyces, Penicillium, Phanerochaete, Phiebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bierkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophile, Neurospora crassa, Penicillium purpurogenum, Phanerochaete chrysosporium, Phlebia radiate, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc, Natl. Acad. Sci. USA* 81: 1470-1474. Suitable methods for transforming *Fusarium* species are described by Malardier et al., 1989. *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for the expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermenters performed in a suitable medium and under conditions allowing the peptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods may include use of specific antibodies, formation of an enzyme product, or disappearance of an enzyme substrate. For example, an enzyme assay may be used to determine the activity of the variant.

The variant may be recovered by methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J. C. Janson and Lars Ryden, editors, VCH Publishers, New York, 1989) to obtain substantially pure variants.

In an alternative aspect, the variant is not recovered, but rather a host cell of the present invention expressing a variant is used as a source of the variant.

In Vitro Synthesis

The polypeptides of the invention may also be prepared by in vitro synthesis, using conventional methods as known in the art. Various commercial synthetic apparatuses are available, for example automated synthesizers by Applied Biosystems Inc., Beckman, etc. By using synthesizers, naturally occurring amino acids may be substituted with unnatural amino acids, particularly D-isomers (or D-forms) e.g. D-alanine and D-isoleucine, diastereoisomers, side chains having different lengths or functionalities, and the like. The particular sequence and the manner of preparation will be determined by convenience, economics, purity required, and the like.

Chemical linking may be provided to various peptides or proteins comprising convenient functionalities for bonding, such as amino groups for amide or substituted amine formation, e.g. reductive amination, thiol groups for thioether or disulfide formation, carboxyl groups for amide formation, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Plants

The present invention also relates to plants, e.g., a transgenic plant, plant part, or plant cell, comprising a polynucleotide of the present invention so as to express and produce the variant in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seeds coats.

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more (several) expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiol.* 86: 506.

For constitutive expression, the 35S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* (39: 885-889), a *Vicia faba* promoter from the legumin B4 and the unknown seed protein gene from *Vicia faba* (Conrad et al., 1998, *J. Plant Physiol,* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248:

668-674), or a wound inducible promoter such as the potato pin2 promoter (Xu et al., 1993, *Plant Mol. Biol.* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Mol. Biol.* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, cotransformation with two separate T-DNA constructs or site specific excision of the selection gene by a specific recombinase.

In addition to direct transformation of a particular plant genotype with a construct prepared according to the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. Crossing results in the introduction of a transgene into a plant line by cross pollinating a starting line with a donor plant line. Non-limiting examples of such steps are further articulated in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a variant of the present invention comprising: (a) cultivating a transgenic plant or a plant cell comprising a polynucleotide encoding the variant under conditions conducive for production of the variant; and (b) recovering the variant.

Methods and Uses

The present invention is also directed to methods for using the polypeptides having antimicrobial activity. The antimicrobial polypeptides are typically useful at any locus subject to contamination by microorganisms. Typically, loci are in aqueous systems such as cooling water systems, where microorganisms need to be killed or where their growth needs to be controlled. However, the present invention may also be used in all applications for which known antimicrobial compositions are useful, such as protection of wood, latex, adhesive, glue, paper, cardboard, textile, leather and feed.

Other uses include preservation of foods, beverages, cosmetics such as lotions, creams, gels, ointments, soaps, shampoos, conditioners, antiperspirants, deodorants, mouth wash, contact lens products or food ingredients.

In general it is contemplated that the antimicrobial polypeptides of the present invention are useful for cleaning, disinfecting or inhibiting microbial growth on any surface. Examples of surfaces, which may advantageously be contacted with the antimicrobial polypeptides of the invention, are surfaces of process equipment used e.g. dairies, chemical or pharmaceutical process plants. The antimicrobial polypeptides of the invention should be used in an amount, which is effective for cleaning, disinfecting or inhibiting microbial growth on the surface in question.

The antimicrobial polypeptides of the invention may additionally be used for cleaning surfaces and cooking utensils in food processing plants and in any area in which food is prepared or served such as hospitals, nursing homes and restaurants.

The invention also relates to the use of an antimicrobial polypeptide or composition of the invention as a medicament. Further, an antimicrobial polypeptide or composition of the invention may also be used for the manufacture of a medicament for controlling or combating microorganisms, such as fungal organisms or bacteria, preferably gram negative bacteria.

The composition and antimicrobial polypeptide of the invention may be used as an antimicrobial veterinarian or human therapeutic or prophylactic agent. Thus, the composition and antimicrobial polypeptide of the invention may be used in the preparation of veterinarian or human therapeutic agents or prophylactic agents for the treatment of microbial infections, such as bacterial or fungal infections, preferably gram positive bacterial infections. In particular the microbial infections may be associated with lung diseases including, but not limited to, tuberculosis, pneumonia and cystic fibrosis; skin infections and infections in the eye or the mouth; and sexually transmitted diseases including, but not limited to, gonorrhea and chlamydia.

The invention also relates to wound healing compositions or products such as bandages, medical devices such as, e.g., catheters.

The composition of the invention comprises an effective amount of the antimicrobial polypeptide of the invention.

The term "effective amount" when used herein is intended to mean an amount of the antimicrobial polypeptides of the invention, which is sufficient to inhibit growth of the microorganisms in question.

Formulations of the antimicrobial polypeptides of the invention are administered to a host suffering from or predisposed to a microbial infection. Administration may be topical, localized or systemic, depending on the specific microorganism, preferably it will be localized. Generally the dose of the antimicrobial polypeptides of the invention will be sufficient to decrease the microbial population by at least about 50%, usually by at least 1 log, and may be by 2 or more logs of killing. The compounds of the present invention are administered at a dosage that reduces the microbial population while minimizing any side-effects. It is contemplated that the composition will be obtained and used under the guidance of a physician for in vivo use. The antimicrobial polypeptides of the invention are particularly useful for killing gram negative bacteria, including *Pseudomonas aeruginosa*, and *Chlamydia trachomatis*; and gram-positive bacteria, including streptococci such as *Streptococcus pneumonia*, *S. uberis, S. hyointestinalis, S. pyogenes* and *S. agalactiae*; and staphylococci such as *Staphylococcus aureus, S. epidermidis, S. simulans, S. xylosus* and *S. carnosus*.

Formulations of the antimicrobial polypeptides of the invention may be administered to a host suffering from or predisposed to a microbial lung infection, such as pneumonia; or to a microbial wound infection, such as a bacterial wound infection.

Formulations of the antimicrobial polypeptides of the invention may also be administered to a host suffering from or predisposed to a skin infection, such as acne, atopic dermatitis or seborrheic dermatitis; preferably the skin infection is a bacterial skin infection, e.g. caused by *Staphylococcus epidermidis, Staphylococcus aureus, Propionibacterium acnes, Pityrosporum ovale* or *Malassezia furfur*.

The antimicrobial polypeptides of the invention are also useful for in vitro formulations to kill microbes, particularly where one does not wish to introduce quantities of conventional antibiotics. For example, the antimicrobial polypeptides of the invention may be added to animal and/or human food preparations; or they may be included as an additive for in vitro cultures of cells, to prevent the overgrowth of microbes in tissue culture.

The susceptibility of a particular microbe to killing with the antimicrobial polypeptides of the invention may be determined by in vitro testing, as detailed in the experimental section. Typically a culture of the microbe is combined with the antimicrobial polypeptide at varying concentrations for a period of time sufficient to allow the protein to act, usually between about one hour and one day. The viable microbes are then counted, and the level of killing determined.

Microbes of interest include, but are not limited to, Gram-negative bacteria, for example: *Citrobacter* sp.; *Enterobacter* sp.; *Escherichia* sp., e.g. *E. coli*; *Klebsiella* sp.; *Morganella* sp.; *Proteus* sp.; *Providencia* sp.; *Salmonella* sp., e.g. *S. typhi, S. typhimurium; Serratia* sp.; *Shigella* sp.; *Pseudomonas* sp., e.g. *P. aeruginosa; Yersinia* sp., e.g. *Y. pestis, Y. pseudotuberculosis, Y. enterocolitica; Franciscella* sp.; *Pasturella* sp.; *Vibrio* sp., e.g. *V. cholerae, V. parahemolyticus; Campylobacter* sp., e.g. *C. jejuni; Haemophilus* sp., e.g. *H. influenzae, H. ducreyi; Bordetella* sp., e.g. *B. pertussis, B. bronchiseptica, B. parapertussis; Brucella* sp., *Neisseria* sp., e.g. *N. gonorrhoeae, N. meningitidis*, etc. Other bacteria of interest include *Legionella* sp., e.g. *L. pneumophila; Listeria* sp., e.g. *L. monocytogenes; Mycoplasma* sp., e.g. *M. hominis, M. pneumoniae; Mycobacterium* sp., e.g. *M. tuberculosis, M. leprae; Treponerna* sp., e.g. *T. pallidum; Borrelia* sp., e.g. *B. burgdorferi; Leptospirae* sp.; *Rickettsia* sp., e.g. *R. rickettsii, R. typhi; Chlamydia* sp., e.g. *C. trachomatis, C. pneumoniae, C. psittaci; Helicobacter* sp., e.g. *H. pylori*, etc.

Non-bacterial pathogens of interest include fungal and protozoan pathogens, e.g. *Plasmodia* sp., e.g. *P. falciparum, Trypanosoma* sp., e.g. *T. brucei; shistosomes; Entaernoeba* sp., *Cryptococcus* sp., *Candida* sp., e.g. *C. albicans*; etc.

Various methods for administration may be employed. The polypeptide formulation may be given orally, or may be injected intravascularly, subcutaneously, peritoneally, by aerosol, opthalmically, intra-bladder, topically, etc. For example, methods of administration by inhalation are well-known in the art. The dosage of the therapeutic formulation will vary widely, depending on the specific antimicrobial polypeptide to be administered, the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered once or several times daily, semi-weekly, etc. to maintain an effective dosage level. In many cases, oral administration will require a higher dose than if administered intravenously. The amide bonds, as well as the amino and carboxy termini, may be modified for greater stability on oral administration. For example, the carboxy terminus may be amidated.

Formulations

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, creams, foams, solutions, suppositories, injections, inhalants, gels, microspheres, lotions, and aerosols. As such, administration of the compounds can be achieved in various ways, including oral, buccal, rectal, parenteral, intraperitoneal, intradermal, transdermal, intracheal, etc., administration. The antimicrobial polypeptides of the invention may be systemic after administration or may be localized by the use of an implant or other formulation that acts to retain the active dose at the site of implantation.

The compounds of the present invention can be administered alone, in combination with each other, or they can be used in combination with other known compounds (e.g., perforin, anti-inflammatory agents, antibiotics, etc.). In pharmaceutical dosage forms, the compounds may be administered in the form of their pharmaceutically acceptable salts. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc: with biodegradable or non-biodegradable polymers. For example, polymers of lactic acid and/or glycolic acid form an erodible polymer that is well-tolerated by the host. The implant containing the antimicrobial polypeptides of the invention is placed in proximity to the site of infection, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with the compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 pg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic or zwitterionic lipids, such as phosphatidylcholine. The remaining lipid will be normally be neutral or acidic lipids, such as cholesterol, phosphatidyl serine, phosphatidyl glycerol, and the like.

For preparing the liposomes, the procedure described by Kato et al., 1991, *J. Biol. Chem.* 266:3361 may be used. Briefly, the lipids and lumen composition containing peptides are combined in an appropriate aqueous medium, conveniently a saline medium where the total solids will be in the range of about 1-10 weight percent. After intense agitation for short periods of time, from about 5-60 seconds, the tube is placed in a warm water bath, from about 25-40° C. and this cycle repeated from about 5-10 times. The composition is then sonicated for a convenient period of time, generally from about 1-10 seconds and may be further agitated by vortexing. The volume is then expanded by adding aqueous medium, generally increasing the volume by about from 1-2 fold, followed by shaking and cooling. This method allows for the incorporation into the lumen of high molecular weight molecules.

Formulations with Other Active Agents

For use in the subject methods, the antimicrobial polypeptides of the invention may be formulated with other pharmaceutically active agents, particularly other antimicrobial agents. Other agents of interest include a wide variety of antibiotics, as known in the art. Classes of antibiotics include penicillins, e.g., penicillin G, penicillin V, methicillin, oxacillin, carbenicillin, nafcillin, ampicillin, etc.; penicillins in combination with beta-lactamase inhibitors, cephalosporins, e.g., cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin: trimethoprim: vancomycin; etc.

Anti-mycotic agents are also useful, including polyenes, e.g., amphotericin B, nystatin; 5-flucasyn; and azoles, e.g., miconazol, ketoconazol, itraconazol and fluconazol. Antituberculotic drugs include isoniazid, ethambutol, streptomycin and rifampin. Cytokines may also be included in a formulation of the antimicrobial polypeptides of the invention, e.g. interferon gamma, tumor necrosis factor alpha, interleukin 12, etc.

The present invention is further described by the following examples that should not be construed as limiting the scope of the invention.

EXAMPLES

NZ17074 is the antimicrobial peptide of SEQ ID NO: 70.

Example 1

Isolation of Variants of SEQ ID NO: 2 Having Improved Antimicrobial Activity

The cDNA encoding SEQ ID NO: 2 was fused to the proregion of plectasin (see Mygind et al., 2005, Nature 437: 975-980) and the Mating Factor alpha-leader from Saccharomyces cerevisiae and introduced into the inducible S. cerevisiae expression vector, pYES2, and transformed into S. cerevisiae. This system takes advantage of the GAL1 promoter which is repressed by glucose and activated by galactose.

Several strategies were used for variant generation of the polynucleotide of SEQ ID NO:1. The resulting libraries were cloned and expressed in S. cerevisiae. Transformed clones were screened on a plate assay containing growth media supplemented with 1.5% galactose and 0.5% glucose and either horse blood (2.5-5%) or serum (5%), overlayed with the target organism, E. coli ATCC 10536 (See Raventos at al., 2005, Comb Chem High Throughput Screen 8:219-33).

The plate assay conditions fully inhibited the activity of the antimicrobial peptide of SEQ ID NO: 2 (the parent antimicrobial peptide). Variants exhibiting improved antimicrobial activity (giving rise to clearing zones) in the presence of 2.5% blood, 5% blood or 5% serum were picked and sequenced, and are shown in Table 1.

Plate Assay Screening Procedure

Approximately, 300 Saccharomyces cerevisiae colonies expressing arenicin variants were spread on screening plates containing either horse blood (2.5% or 5%) or 5% horse serum (see composition of the plates below). Plates were incubated 3 hours at 30° C. to allow them to dry. Next, 25 ml overlay temperated at 42° C. was added to the plates. After the media had solidified, the plates were incubated 3 days at 30° C.

On day 4, plates were overlayed with pre-warmed media at 42° C. containing either 2.5% or 5% horse blood or 5% horse serum and the target bacteria, E. coli ATCC 10536 (see below for details on media composition). After the overlay solidified, plates were incubated 16 hours at 37° C. Next day, plates were colored by adding 10 ml of 1.5 mM MTT to the plates and incubated at room temperature for 30 minutes. Clones giving rise to clearing zones were picked and sequenced.

Plate and Media Composition

Three different types of screening plates a), b) and c) were used in the screening:

a) Plates+2.5% Horse Blood

The bottom layer contains 50 ml of 1.5% agarose+¼ SC media+2.5% blood+1.5% galactose+0.5% glucose. The first overlay contains 25 ml of 1% agarose+¼ SC media+2.5% blood+1.5% galactose+0.5% glucose. The top overlay contains 25 ml 0.2% MHB (#212322; BD)+1% agarose (Sigma A-4718)+2.5% horse blood and $1.25 \times 10^6$ colony forming units (cfu) of E. coli ATCC 10536.

b) Plates+5% Horse Blood

The bottom layer contains 50 ml of 1.5% agarose+¼ SC media+5% blood+1.5% galactose+0.5% glucose. The first overlay contains 25 ml of 1% agarose+¼ SC media+5% blood+1.5% galactose+0.5% glucose. The top overlay contains 25 ml 0.2% MHB (#212322; BD)+1% agarose (Sigma A-4718)+5% horse blood and $1.25 \times 10^6$ colony forming units (cfu) of E. coli ATCC 10536.

c) Plates+5% Horse Serum

The bottom layer contains 50 ml of 1.5% agarose+½ SC media+5% serum+1.5% galactose+0.5% glucose. The first overlay contains 25 ml of 1% agarose+½ SC media+5% serum+1.5% galactose+0.5% glucose. The top overlay contains 25 ml 0.2% MHB (#212322; BD)+1% agarose (Sigma A-4718)+5% horse serum and $1.25 \times 10^6$ colony forming units (cfu) of E. coli ATCC 10536.

Composition of SC Media (450 ml)

| | |
|---|---|
| Yeast Nitrogen Base w/o amino acids: | 3.75 g |
| Succinic acid: | 5.65 g |
| Sodium hydroxide: | 3.4 g |
| Casamino acid vitamin assay: | 2.8 g |
| L-Tryptophan: | 0.05 g |
| Water: | 450 ml | pH was adjusted to 6 and the media was autoclaved and diluted ¼ when preparing the blood plates and ½ when preparing the serum plates.

MTT: (3-(4,5-dimethylthiazol-2-yl)-2,5-diphenyl-2H-tetrazolium bromide, Sigma 13, 503-8)

Determination of the Protein Binding

Protein binding assays were performed as follows. The purified peptides were mixed with 90% serum and centrifuged through a 30 kDa filter. The ultra-filtrate and the non filtrated serum samples were quantified by HPLC measurements and the protein binding was subsequently calculated.

The antimicrobial peptide of SEQ ID NO: 2 (the parent antimicrobial peptide) exhibited a protein binding of 99.5% in this assay. As shown in Table 1, all exemplified variants exhibit a lower protein binding than the antimicrobial peptide of SEQ ID NO: 2.

TABLE 1

Variants exhibiting improved antimicrobial activity and reduced protein binding. The symbol "—" means "not analyzed".

| SEQ ID NO | Substitution | Amino acid sequence | Protein binding (%) |
|---|---|---|---|
| 3 | F2A | GACWYVCVYRNGVRVCYRRCN | 86 |
| 4 | W4A | GFCAYVCVYRNGVRVCYRRCN | 89 |

TABLE 1-continued

Variants exhibiting improved antimicrobial activity and reduced protein binding. The symbol "—" means "not analyzed".

| SEQ ID NO | Substitution | Amino acid sequence | Protein binding (%) |
|---|---|---|---|
| 5 | W4E | GFCEYVCVYRNGVRVCYRRCN | — |
| 6 | W4G | GFCGYVCVYRNGVRVCYRRCN | — |
| 7 | W4S | GFCSYVCVYRNGVRVCYRRCN | 68 |
| 8 | W4T | GFCTYVCVYRNGVRVCYRRCN | — |
| 9 | W4Y | GFCYYVCVYRNGVRVCYRRCN | — |
| 10 | Y5K | GFCWKVCVYRNGVRVCYRRCN | 64 |
| 11 | Y5N | GFCWNVCVYRNGVRVCYRRCN | 73 |
| 12 | Y5R | GFCWRVCVYRNGVRVCYRRCN | — |
| 13 | V6A | GFCWYACVYRNGVRVCYRRCN | — |
| 14 | V6E | GFCWYECVYRNGVRVCYRRCN | — |
| 15 | V6G | GFCWYGCVYRNGVRVCYRRCN | 96 |
| 16 | V6L | GFCWYLCVYRNGVRVCYRRCN | — |
| 17 | V6N | GFCWYNCVYRNGVRVCYRRCN | — |
| 18 | V6R | GFCWYRCVYRNGVRVCYRRCN | — |
| 19 | V6S | GFCWYSCVYRNGVRVCYRRCN | 89 |
| 20 | V6W | GFCWYWCVYRNGVRVCYRRCN | 99 |
| 21 | V8A | GFCWYVCAYRNGVRVCYRRCN | 98.5 |
| 22 | V8G | GFCWYVCGYRNGVRVCYRRCN | — |
| 23 | V8H | GFCWYVCHYRNGVRVCYRRCN | 98 |
| 24 | V8S | GFCWYVCSYRNGVRVCYRRCN | 85 |
| 25 | V8Y | GFCWYVCYYRNGVRVCYRRCN | 98 |
| 26 | Y9I | GFCWYVCVIRNGVRVCYRRCN | — |
| 27 | Y9K | GFCWYVCVKRNGVRVCYRRCN | — |
| 28 | Y9R | GFCWYVCVRRNGVRVCYRRCN | 92 |
| 29 | V13A | GFCWYVCVYRNGARVCYRRCN | 99 |
| 30 | V13G | GFCWYVCVYRNGGRVCYRRCN | 99 |
| 31 | v13K | GFCWYVCVYRNGKRVCYRRCN | — |
| 32 | V13L | GFCWYVCVYRNGLRVCYRRCN | — |
| 33 | V13P | GFCWYVCVYRNGPRVCYRRCN | 99 |
| 34 | V13Q | GFCWYVCVYRNGQRVCYRRCN | — |
| 35 | V13R | GFCWYVCVYRNGRRVCYRRCN | — |
| 36 | V13S | GFCWYVCVYRNGSRVCYRRCN | 60 |
| 37 | V15A | GFCWYVCVYRNGVRACYRRCN | — |
| 38 | v15G | GFCWYVCVYRNGVRGCYRRCN | 93 |
| 39 | V15H | GFCWYVCVYRNGVRHCYRRCN | 98 |
| 40 | V15K | GFCWYVCVYRNGVRKCYRRCN | — |
| 41 | V15N | GFCWYVCVYRNGVRNCYRRCN | 97 |

TABLE 1-continued

Variants exhibiting improved antimicrobial activity and reduced protein binding.
The symbol "—" means "not analyzed".

| SEQ ID NO | Substitution | Amino acid sequence | Protein binding (%) |
|---|---|---|---|
| 42 | V15Q | GFCWYVCVYRNGVRQCYRRCN | 96 |
| 43 | V15R | GFCWYVCVYRNGVRRCYRRCN | — |
| 44 | V15S | GFCWYVCVYRNGVRSCYRRCN | 85 |
| 45 | V15T | GFCWYVCVYRNGVRTCYRRCN | 98 |
| 46 | Y17H | GFCWYVCVYRNGVRVCHRRCN | 88 |
| 47 | Y17K | GFCWYVCVYRNGVRVCKRRCN | 89 |
| 48 | Y17N | GFCWYVCVYRNGVRVCNRRCN | 68 |
| 49 | Y17R | GFCWYVCVYRNGVRVCRRRCN | — |
| 50 | N21H | GFCWYVCVYRNGVRVCYRRCH | — |
| 51 | N21K | GFCWYVCVYRNGVRVCYRRCK | — |
| 52 | N21R | GFCWYVCVYRNGVRVCYRRCR | — |
| 53 | N21S | GFCWYVCVYRNGVRVCYRRCS | 99 |
| 54 | N21T | GFCWYVCVYRNGVRVCYRRCT | 99 |
| 55 | G1R + N21R | RFCWYVCVYRNGVRVCYRRCR | — |
| 56 | W4F + Y17R | GFCFYVCVYRNGVRVCRRRCN | 94 |
| 57 | W4A + Y5H | GFCAHVCVYRNGVRVCYRRCN | — |
| 58 | W4A + Y5R | GFCARVCVYRNGVRVCYRRCN | — |
| 59 | W4F + Y9R | GFCFYVCVRRNGVRVCYRRCN | — |
| 60 | W4G + Y5H | GFCGHVCVYRNGVRVCYRRCN | 64 |
| 61 | W4G + Y5R | GFCGRVCVYRNGVRVCYRRCN | 72 |
| 62 | W4S + V15A | GFCSYVCVYRNGVRACYRRCN | — |
| 63 | W4S + Y5R | GFCSRVCVYRNGVRVCYRRCN | — |
| 64 | W4Y + Y5R | GFGYRVCVYRNGVRVCYRRCN | — |
| 65 | Y5F + V15Q | GFCWFVCVYRNGVRQCYRRCN | — |
| 66 | Y5H + V15S | GFCWHVCVYRNGVRSCYRRCN | — |
| 67 | Y5H + Y17R | GFCWHVCVYRNGVRVCRRRCN | — |
| 68 | Y5K + Y17S | GFCWKVCVYRNGVRVCSRRCN | 87 |
| 69 | Y5N + V15S | GFCWNVCVYRNGVRSCYRRCN | — |
| 70 | Y5N + Y17H | GFCWNVCVYRNGVRVCHRRCN | 79 |
| 71 | Y5R + V15P | GFCWRVCVYRNGVRPCYRRCN | — |
| 72 | Y5R + V6A | GFCWRACVYRNGVRVCYRRCN | 97 |
| 73 | Y5R + V8G | GFCWRVCGYRNGVRVCYRRCN | — |
| 74 | Y5R + V8H | GFCWRVCHYRNGVRVCYRRCN | 99 |
| 75 | Y5R + V8S | GFCWRVCSYRNGVRVCYRRCN | — |
| 76 | Y5R + Y17H | GFCWRVCVYRNGVRVCHRRCN | 92 |
| 77 | Y5R + Y17N | GFCWRVCVYRNGVRVCNRRCN | — |

TABLE 1-continued

Variants exhibiting improved antimicrobial activity and reduced protein binding. The symbol "—" means "not analyzed".

| SEQ ID NO | Substitution | Amino acid sequence | Protein binding (%) |
|---|---|---|---|
| 78 | Y5S + V15S | GFCWSVCVYRNGVRSCYRRCN | — |
| 79 | V6A + V13A | GFCWYACVYRNGARVCYRRCN | — |
| 80 | V6A + V13K | GFCWYACVYRNGKRVCYRRCN | 96 |
| 81 | V6A + V15A | GFCWYACVYRNGVRACYRRCN | — |
| 82 | V6A + Y17H | GFCWYACVYRNGVRVCHRRCN | — |
| 83 | V6M + V8G | GFCWYMCGYPNGVRVCYRRCN | — |
| 84 | V8A + V15A | GFCWYVCAYRNGVRACYRRCN | — |
| 85 | V8S + V13K | GFGWYVCSYRNGKRVCYRRCN | — |
| 86 | Y9K + V13A | GFCWYVCVKRNGARVCYRRCN | — |
| 87 | Y9K + V15S | GFCWYVCVKRNGVRSCYRRCN | 93 |
| 88 | R10K + V15S | GFCWYVCVYKNGVRSCYRRCN | — |
| 89 | R10K + Y17H | GFCWYVCVYKNGVRVCHRRCN | 90 |
| 90 | R10P + V13G | GFCWYVCVYPNGGRVCYRRCN | — |
| 91 | N11R + V15Q | GFCWYVCVYRRGVRQCYRRCN | — |
| 92 | V13A + Y17C | GFCWYVCVYRNGARVCCRRCN | — |
| 93 | V13G + V15K | GFCWYVCVYRNGGRKCYRRCN | — |
| 94 | V15L + Y17H | GFCWYVCVYRNGVRLCHRRCN | — |
| 95 | G1A + Y5N + Y17H | AFCWNVCVYRNGVRVCHRRCN | — |
| 96 | G1D + Y5N + Y17H | DFCWNVCVYRNGVRVCHRRCN | — |
| 97 | G1F + Y5N + Y17H | FFCWNVCVYRNGVRVCHRRCN | — |
| 98 | G1H + Y5N + Y17H | HFCWNVCVYRNGVRVCHRRCN | 77 |
| 99 | G1I + Y5N + Y17H | IFCWNVCVYRNGVRVCHRRCN | — |
| 100 | G1K + Y5N + Y17H | KFCWNVCVYRNGVRVCHRRCN | 78 |
| 101 | G1M + Y5N + Y17H | MFCWNVCVYRNGVRVCHRRCN | 81 |
| 102 | G1Q + Y5N + Y17H | QFCWNVCVYRNGVRVCHRRCN | — |
| 103 | G1R + Y5N + Y17H | RFCWNVCVYRNGVRVCHRRCN | — |
| 104 | G1S + Y5N + Y17H | SFCWNVCVYRNGVRVCHRRCN | — |
| 105 | G1T + Y5N + Y17H | TFCWNVCVYRNGVRVCHRRCN | — |
| 106 | G1V + Y5N + Y17H | VFCWNVCVYRNGVRVCHRRCN | — |
| 107 | G1W + Y5N + Y17H | WFCWNVCVYRNGVRVCHRRCN | — |
| 108 | G1Y + Y5N + Y17H | YFCWNVCVYRNGVRVCHRRCN | — |
| 109 | F2G + Y5N + Y17H | GGCWNVCVYRNGVRVCHRRCN | — |
| 110 | F2H + Y5N + Y17H | GHCWNVCVYRNGVRVCHRRCN | — |
| 111 | F2I + Y5N + Y17H | GICWNVCVYRNGVRVCHRRCN | — |
| 112 | F2L + Y5N + Y17H | GLCWNVCVYRNGVRVCHRRCN | — |
| 113 | F2M + Y5N + Y17H | GMCWNVCVYRNGVRVCHRRCN | — |
| 114 | F2P + Y5N + Y17H | GPCWNVCVYRNGVRVCHRRCN | — |

TABLE 1-continued

Variants exhibiting improved antimicrobial activity and reduced protein binding. The symbol "—" means "not analyzed".

| SEQ ID NO | Substitution | Amino acid sequence | Protein binding (%) |
|---|---|---|---|
| 115 | F2V + Y5N + Y17H | GVCWNVCVYRNGVRVCHRRCN | — |
| 116 | F2W + Y5N + Y17H | GWCWNVCVYRNGVRVCHRRCN | — |
| 117 | F2Y + Y5N + Y17H | GYCWNVCVYRNGVRVCHRRCN | — |
| 118 | C3L + W4Q + Y17H | GFLQYVCVYRNGVRVCHRRCN | — |
| 119 | W4A + V6A + Y9K | GFCAYACVKRNGVRVCYRRCN | — |
| 120 | W4A + Y5K + V15S | GFCAKVCVYRNGVRSCYRRCN | 69 |
| 121 | W4A + Y5R + V15A | GFCARVCVYRNGVRACYRRCN | — |
| 122 | W4A + Y5R + V15S | GFCARVCVYRNGVRSCYRRCN | 81 |
| 123 | W4A + Y5R + V15T | GFCARVCVYRNGVRTCYRRCN | — |
| 124 | W4A + Y5R + V8S | GFCARVCSYRNGVRVCYRRCN | — |
| 125 | W4A + Y5R + Y9K | GFCARVCVKRNGVRVCYRRCN | 90 |
| 126 | W4A + Y5W + V15Q | GFCAWVCVYRNGVRQCYRRCN | — |
| 127 | W4A + Y9R + V15S | GFCAYVCVRRNGVRSCYRRCN | — |
| 128 | W4F + V8A + V15S | GFCFYVCAYRNGVRSCYRRCN | — |
| 129 | W4F + Y5H + V15S | GFCFHVCVYRNGVRSCYRRCN | — |
| 130 | W4F + Y5N + V15S | GFCFNVCVYRNGVRSCYRRCN | — |
| 131 | W4F + Y5N + Y17H | GFCFNVCVYRNGVRVCHRRCN | — |
| 132 | W4F + Y5R + V15K | GFCFRVCVYRNGVRKCYRRCN | — |
| 133 | W4F + Y5R + V15Q | GFCFRVCVYRNGVRQCYRRCN | — |
| 134 | W4F + Y5R + V15S | GFCFRVCVYRNGVRSCYRRCN | — |
| 135 | W4F + Y5R + Y17H | GFCFRVCVYRNGVRVCHRRCN | — |
| 136 | W4F + Y5R + Y17Q | GFCFRVCVYRNGVRVCQRRCN | — |
| 137 | W4F + Y9K + Y17H | GFCFYVCVKRNGVRVCHRRCN | 86 |
| 138 | W4G + Y5H + N21A | GFCGHVCVYRNGVRVCYRRCA | — |
| 139 | W4G + Y5H + N21K | GFCGHVCVYRNGVRVCYRRCK | — |
| 140 | W4G + Y5H + N21L | GFCGHVCVYRNGVRVCYRRCL | — |
| 141 | W4G + Y5H + N21M | GFCGHVCVYRNGVRVCYRRCM | — |
| 142 | W4G + Y5H + N21P | GFCGHVCVYRNGVRVCYRRCP | — |
| 143 | W4G + Y5H + N21R | GFCGHVCVYRNGVRVCYRRCR | — |
| 144 | W4G + Y5H + N21S | GFCGHVCVYRNGVRVCYRRCS | 68 |
| 145 | W4G + Y5H + N21Y | GFCGHVCVYRNGVRVCYRRCY | — |
| 146 | W4G + Y5H + V15A | GFCGHVCVYRNGVRACYRRCN | — |
| 147 | W4G + Y5H + V15F | GFCGHVCVYRNGVRECYRRCN | — |
| 148 | W4G + Y5H + V15G | GFCGHVCVYRNGVRGCYRRCN | — |
| 149 | W4G + Y5H + V15H | GFCGHVCVYRNGVRHCYRRCN | — |
| 150 | W4G + Y5H + V15I | GFCGHVCVYRNGVRICYRRCN | — |

TABLE 1-continued

Variants exhibiting improved antimicrobial activity and reduced protein binding.
The symbol "—" means "not analyzed".

| SEQ ID NO | Substitution | Amino acid sequence | Protein binding (%) |
|---|---|---|---|
| 151 | W4G + Y5H + V15L | GFCGHVCVYRNGVRLCYRRCN | — |
| 152 | W4G + Y5H + V15M | GFCGHVCVYRNGVRMCYRRCN | — |
| 153 | W4G + Y5H + V15N | GFCGHVCVYRNGVRNCYRRCN | — |
| 154 | W4G + Y5H + V15Q | GFCGHVCVYRNGVRQCYRRCN | — |
| 155 | W4G + Y5H + V15R | GFCGHVCVYRNGVRRCYRRCN | 83 |
| 156 | W4G + Y5H + V15S | GFCGHVCVYRNGVRSCYRRCN | — |
| 157 | W4G + Y5H + V15T | GFCGHVCVYRNGVRTCYRRCN | — |
| 158 | W4G + Y5H + V15W | GFCGHVCVYRNGVRWCYRRCN | — |
| 159 | W4G + Y5H + V15Y | GFCGHVCVYRNGVRYCYRRCN | — |
| 160 | W4G + Y5H + Y17F | GFCGRVCVYRNGVRVCFRRCN | — |
| 161 | W4G + Y5H + Y17G | GFCGHVCVYRNGVRVCGRRCN | — |
| 162 | W4G + Y5H + Y17I | GFCGHVCVYRNGVRVCIRRCN | — |
| 163 | W4G + Y5H + Y17L | GFCGHVCVYRNGVRVCLRRCN | — |
| 164 | W4G + Y5H + Y17M | GFCGHVCVYRNGVRVCMRRCN | — |
| 165 | W4G + Y5H + Y17T | GFCGHVCVYRNGVRVCTRRCN | — |
| 166 | W4G + Y5H + Y17V | GFCGHVCVYRNGVRVCVRRCN | — |
| 167 | W4G + Y5H + Y17W | GFCGHVCVYRNGVRVCWRRCN | — |
| 168 | W4G + Y5K + V15H | GFCGKVCVYRNGVRHCYRRCN | — |
| 169 | W4G + Y5R + V15L | GFCGRVCVYRNGVRLCYRRCN | — |
| 170 | W4G + Y5R + V15R | GFCGRVCVYRNGVRRCYRRCN | 87 |
| 171 | W4G + Y5R + V15T | GFCGRVCVYRNGVRTCYRRCN | 84 |
| 172 | W4G + Y5R + Y9R | GFCGRVCVRRNGVRVCYRRCN | 88 |
| 173 | W4G + Y5S + V15A | GFCGSVCVYRNGVRACYRRCN | — |
| 174 | W4G + Y5S + V15K | GFCGSVCVYRNGVRKCYRRCN | — |
| 175 | W4G + Y5S + V15R | GFCGSVCVYRNGVRRCYRRCN | — |
| 176 | W4G + Y9R + V15S | GFCGYVCVRRNGVRSCYRRCN | — |
| 177 | W4I + Y5N + Y17H | GFCINVCVYRNGVRVCHRRCN | — |
| 178 | W4L + Y5H + V15Q | GFCLHVCVYRNGVRQCYRRCN | — |
| 179 | W4L + Y5K + V15K | GFCLKVCVYRNGVRKCYRRCN | — |
| 180 | W4L + Y5R + V15Q | GFCLRVCVYRNGVRQCYRRCN | — |
| 181 | W4L + Y5R + V15S | GFCLRVCVYRNGVRSCYRRCN | — |
| 182 | W4M + Y5E + Y17T | GFCMEVCVYRNGVRVCTRRCN | — |
| 183 | W4M + Y5H + V15S | GFCMHVCVYRNGVRSCYRRCN | — |
| 184 | W4M + Y5N + Y17H | GFCMNVCVYRNGVRVCHRRCN | — |
| 185 | W4M + Y5R + V15T | GFCMRVCVYRNGVRTCYRRCN | — |
| 186 | W4M + Y5S + V15Q | GFCMSVCVYRNGVRQCYRRCN | — |
| 187 | W4M + Y5S + V15R | GFCMSVCVYRNGVRRCYRRCN | — |

TABLE 1-continued

Variants exhibiting improved antimicrobial activity and reduced protein binding.
The symbol "—" means "not analyzed".

| SEQ ID NO | Substitution | Amino acid sequence | Protein binding (%) |
|---|---|---|---|
| 188 | W4N + Y5R + V15I | GFCNRVCVYRNGVRICYRRCN | — |
| 189 | W4S + Y5K + V15R | GFCSKVCVYRNGVRRCYRRCN | — |
| 190 | W4S + Y5R + V15I | GFCSRVCVYRNGVRICYRRCN | — |
| 191 | W4T + Y5N + V15A | GFCTNVCVYRNGVRACYRRCN | — |
| 192 | W4T + Y5R + V15R | GFCTRVCVYRNGVRRCYRRCN | — |
| 193 | W4T + Y5R + V15T | GFCTRVCVYRNGVRTCYRRCN | — |
| 194 | W4T + Y5S + V15H | GFCTSVCVYRNGVRHCYRRCN | — |
| 195 | W4T + Y9K + V15K | GFCTYVCVKRNGVRKCYRRCN | 95 |
| 196 | W4V + Y5H + V15P | GFCVHVCVYRNGVRPCYRRCN | — |
| 197 | W4V + Y5H + Y17H | GFCVHVCVYRNGVRVCHRRCN | — |
| 198 | W4V + Y5K + V15Q | GFCVKVCVYRNGVRQCYRRCN | — |
| 199 | W4V + Y5N + Y17H | GFCVNVCVYRNGVRVCHRRCN | — |
| 200 | W4V + Y5R + V15G | GFCVRVCVYRNGVRGCYRRCN | — |
| 201 | W4V + Y5R + V15P | GFCVRVCVYRNGVRPCYRRCN | — |
| 202 | W4V + Y5R + V15Q | GFCVRVCVYRNGVRQCYRRCN | — |
| 203 | W4V + Y5R + V15R | GFCVRVCVYRNGVRRCYRRCN | — |
| 204 | W4V + Y5R + V15T | GFCVRVCVYRNGVRTCYRRCN | — |
| 205 | W4Y + Y5H + V15Y | GFCYHVCVYRNGVRYCYRRCN | — |
| 206 | W4Y + Y5K + V15S | GFCYKVCVYRNGVRSCYRRCN | 86 |
| 207 | W4Y + Y5N + V15R | GFCYNVCVYRNGVRRCYRRCN | 91 |
| 208 | W4Y + Y5N + Y17H | GFCYNVCVYRNGVRVCHRRCN | — |
| 209 | W4Y + Y5R + V15T | GFCYRVCVYRNGVRTCYRRCN | 89 |
| 210 | W4Y + Y5R + Y17H | GFCYRVCVYRNGVRVCHRRCN | 89 |
| 211 | W4Y + Y5R + Y17S | GFCYRVCVYRNGVRVCSRRCN | 96 |
| 212 | W4Y + Y5W + V15S | GFCYWVCVYRNGVRSCYRRCN | — |
| 213 | Y5H + V13A + V15S | GFCWHVCVYRNGARSCYRRCN | 95 |
| 214 | Y5H + V13S + V15S | GFCWHVCVYRNGSRSCYRRCN | — |
| 215 | Y5H + V15S + Y17S | GFCMHVCVYRNGVRSCSRRCN | — |
| 216 | Y5H + V8A + V13K | GFCWHVCAYRNGKRVCYRRCN | — |
| 217 | Y5H + V8A + V15S | GFCWHVCAYRNGVRSCYRRCN | — |
| 218 | Y5H + V8A + Y9R | GFCWHVCARRNGCRVCYRRCN | 99 |
| 219 | Y5H + V8H + G12S | GFCWHVCHYRNSVRVCYRRCN | 99 |
| 220 | Y5H + Y9S + V15K | GFCWHVCVSRNGVRKCYRRCN | — |
| 221 | Y5K + Y9S + Y17S | GFCWKVCVSRNGVRVCSRRCN | — |
| 222 | Y5N + G12A + Y17H | GFCMNVCVYRNAVRVCHRRCN | — |
| 223 | Y5N + G12D + Y17H | GFCWNVCVYRNDVRVCHRRCN | — |

TABLE 1-continued

Variants exhibiting improved antimicrobial activity and reduced protein binding.
The symbol "—" means "not analyzed".

| SEQ ID NO | Substitution | Amino acid sequence | Protein binding (%) |
|---|---|---|---|
| 224 | Y5N + G12E + Y17H | GFCWNVCVYRNEVRVCHRRCN | — |
| 225 | Y5N + G12F + Y17H | GFCWNVCVYRNFVRVCHRRCN | — |
| 226 | Y5N + G12H + Y17H | GFCWNVCVYRNHVRVCHRRCN | — |
| 227 | Y5N + G12K + Y17H | GFCWNVCVYRNKVRVCHRRCN | 80 |
| 228 | Y5N + G12R + Y17H | GFCWNVCVYRNRVRVCHRRCN | 86 |
| 229 | Y5N + G12Y + Y17H | GFCWNVCVYRNYVRVCHRRCN | 91 |
| 230 | Y5N + N11A + Y17H | GFCWNVCVYRAGVRVCHRRCN | 71 |
| 231 | Y5N + N11G + Y17H | GFCWNVCVYRGGVRVCHRRCN | 66 |
| 232 | Y5N + N11H + Y17H | GFCWNVCVYRHGVRVCHRRCN | 85 |
| 233 | Y5N + N11Q + Y17H | GFCWNVCVYRQGVRVCHRRCN | 78 |
| 234 | Y5N + N11R + Y17H | GFCWNVCVYRRGVRVCHRRCN | 86 |
| 235 | Y5N + V13A + Y17H | GFCWNVCVYRNGARVCHRRCN | 64 |
| 236 | Y5N + V13F + Y17H | GFCWNVCVYRNGFRVCHRRCN | — |
| 237 | Y5N + V13H + Y17H | GFCWNVCVYRNGHRVCHRRCN | 40 |
| 238 | Y5N + V13Q + Y17H | GFCWNVCVYRNGQRVCHRRCN | — |
| 239 | Y5N + V13R + Y17H | GFCWNVCVYRNGRRVCHRRCN | 65 |
| 240 | Y5N + V13T + Y17H | GFCWNVCVYRNGTRVCHRRCN | — |
| 241 | Y5N + V13W + Y17H | GFCWNVCVYRNGWRVCHRRCN | — |
| 242 | Y5N + V13Y + Y17H | GFCWNVCVYRNGYRVCHRRCN | 83 |
| 243 | Y5N + V15A + Y17H | GFCWNVCVYRNGVRACHRRCN | — |
| 244 | Y5N + V15C + Y17H | GFCWNVCVYRNGVRCCHRRCN | — |
| 245 | Y5N + V15F + Y17H | GFCWNVCVYRNGVRFCHRRCN | 85 |
| 246 | Y5N + V15G + Y17H | GFCWNVCVYRNGVRGCHRRCN | 79 |
| 247 | Y5N + V15H + Y17H | GFCWNVCVYRNGVRHCHRRCN | — |
| 248 | Y5N + V15I + Y17H | GFCWNVCVYRNGVRICHRRCN | 58 |
| 249 | Y5N + V15L + Y17H | GFCWNVCVYRNGVRLCHRRCN | 83 |
| 250 | Y5N + V15M + Y17H | GFCWNVCVYRNGVRMCHRRCN | — |
| 251 | Y5N + V15N + Y17H | GFCWNVCVYRNGVRNCHRRCN | 71 |
| 252 | Y5N + V15R + Y17H | GFCWNVCVYRNGVRRCHRRCN | 76 |
| 253 | Y5N + V15W + Y17H | GFCWNVCVYRNGVRWCHRRCN | 94 |
| 254 | Y5N + V15Y + Y17H | GFCWNVCVYRNGVRYCHRRCN | 77 |
| 255 | Y5N + V6A + V15N | GFCWNACVYRNGVRNCYRRCN | — |
| 256 | Y5N + V6A + V15S | GFCWNACVYRNGVRSCYRRCN | — |
| 257 | Y5N + V6A + Y17H | GFCWNACVYRNGVRVCHRRCN | — |
| 258 | Y5N + V6A + Y9K | GFCWNACVKRNGVRVCYRRCN | 89 |
| 259 | Y5N + V6C + Y17H | GFCWNCCVYRNGVRVCHPRCN | — |
| 260 | Y5N + V6F + Y17H | GFCWNFCVYRNGVRVCHRRCN | 84 |

TABLE 1-continued

Variants exhibiting improved antimicrobial activity and reduced protein binding. The symbol "—" means "not analyzed".

| SEQ ID NO | Substitution | Amino acid sequence | Protein binding (%) |
|---|---|---|---|
| 261 | Y5N + V6H + Y17H | GFCWNHCVYRNGVRVCHRRCN | — |
| 262 | Y5N + V6I + Y17H | GFCWNICVYRNGVRVCHRRCN | 88 |
| 263 | Y5N + V6L + Y17H | GFCWNLCVYRNGVRVCHRRCN | 80 |
| 264 | Y5N + V6M + Y17H | GFCWNMCVYRNGVRVCHRRCN | — |
| 265 | Y5N + V6Q + Y17H | GFCWNQCVYRNGVRVCHRRCN | — |
| 266 | Y5N + V6T + Y17H | GFCWNTCVYRNGVRVCHRRCN | — |
| 267 | Y5N + V6W + Y17H | GFCWNWCVYRNGVRVCHRRCN | 85 |
| 268 | Y5N + V6Y-i-Y17H | GFCWNYCVYRNGVRVCHRRCN | — |
| 269 | Y5N + V8A + V13A | GFCWNVCAYRNGARVCYRRCN | — |
| 270 | Y5N + V8A + V15S | GFCWNVCAYRNGVRSCYRRCN | — |
| 271 | Y5N + V8A + Y17H | GFCWNVCAYRNGVRVCHRRCN | — |
| 272 | Y5N + V8F + Y17H | GFCWNVCFYRNGVRVCHRRCN | 74 |
| 273 | Y5N + V8G + Y17H | GFCWNVCGYRNGVRVCHRRCN | — |
| 274 | Y5N-1-V8I + Y17H | GFCMNVCIYRNGVRVCHRRCN | — |
| 275 | Y5N + V8L + Y17H | GFCWNVCLYRNGVRVCHRRCN | 80 |
| 276 | Y5N + V8W + Y17H | GFCWNVCWYRNGVRVCHRRCN | — |
| 277 | Y5N + V8Y + Y17H | GFCWNVCYYRNGVRVCHRRCN | — |
| 278 | Y5N + Y17H + N21A | GFCWNVCVYRNGVRVCHRRCA | — |
| 279 | Y5N + Y17H + N21C | GFCWNVCVYRNGVRVCHRRCC | — |
| 280 | Y5N + Y17H + N21F | GFCWNVCVYRNGVRVCHRRCF | — |
| 281 | Y5N + Y17H + N21G | GFCWNVCVYRNGVRVCHRRCG | 66 |
| 282 | Y5N + Y17H + N21H | GFCWNVCVYRNGVRVCHRRCH | 82 |
| 283 | Y5N + Y17H + N21I | GFCWNVCVYRNGVRVCHRRCI | — |
| 284 | Y5N + Y17H + N21K | GFCWNVCVYRNGVRVCHRRCK | 72 |
| 285 | Y5N + Y17H + N21L | GFCWNVCVYRNGVRVCHRRCL | — |
| 286 | Y5N + Y17H + N21M | GFCWNVCVYRNGVRVCHRRCM | — |
| 287 | Y5N + Y17H + N21P | GFCWNVCVYRNGVRVCHRRCP | — |
| 288 | Y5N + Y17H + N21Q | GFCWNVCVYRNGVRVCHRRCQ | — |
| 289 | Y5N + Y17H + N21R | GFCWNVCVYRNGVRVCHRRCR | 83 |
| 290 | Y5N + Y17H + N21S | GFCWNVCVYRNGVRVCHRRCS | — |
| 291 | Y5N + Y17H + N21W | GFCWNVCVYRNGVRVCHRRCW | 99 |
| 292 | Y5N + Y17H + N21Y | GFCWNVCVYRNGVRVCHRRCY | — |
| 293 | Y5N + Y17H + R19D | GFCWNVCVYRNGVRVCHDCN | — |
| 294 | Y5N + Y17H + R19H | GFCWNVCVYRNGVRVCHRHCN | — |
| 295 | Y5N + Y17H + R19K | GFCWNVCVYRNGVRVCHRKCN | — |
| 296 | Y5N + Y17H + R19M | GFCWNVCVYRNGVRVCHRMCN | — |

TABLE 1-continued

Variants exhibiting improved antimicrobial activity and reduced protein binding.
The symbol "—" means "not analyzed".

| SEQ ID NO | Substitution | Amino acid sequence | Protein binding (%) |
|---|---|---|---|
| 297 | Y5N + Y17H + R19T | GFCWNVCVYRNGVRVCHRTCN | — |
| 298 | Y5N + Y17H + R19Y | GFCWNVCVYRNGVRVCHRYCN | — |
| 299 | Y5N + Y9A + Y17H | GFCWNVCVARNGVRVCHRRCN | 74 |
| 300 | Y5N + Y9D + Y17H | GFCWNVCVDRNGVRVCHRRCN | — |
| 301 | Y5N + Y9F + Y17H | GFCWNVCVERNGVRVCHRRCN | — |
| 302 | Y5N + Y9G + Y17H | GFCWNVCVGRNGVRVCHRRCN | — |
| 303 | Y5N + Y9H + Y17H | GFCWNVCVHRNGVRVCHRRCN | 43 |
| 304 | Y5N + Y9I + Y17H | GFCWNVCVIRNGVRVCHRRCN | — |
| 305 | Y5N + Y9K + Y17H | GFCWNVCVKRNGVRVCHRRCN | 76 |
| 306 | Y5N + Y9M + Y17H | GFCWNVCVMRNGVRVCHRRCN | — |
| 307 | Y5N + Y9Q + Y17H | GFCWNVCVQRNGVRVCHRRCN | — |
| 308 | Y5N + Y9R + Y17H | GFCWNVCVRRNGVRVCHRRCN | 94 |
| 309 | Y5N + Y9S + Y17H | GFCWNVCVSRNGVRVCHRRCN | — |
| 310 | Y5N + Y9T + Y17H | GFCWNVCVTRNGVRVCHRRCN | — |
| 311 | Y5N + Y9V + Y17H | GFCWNVCVVRNGVRVCHRRCN | — |
| 312 | Y5N + Y9W + Y17HI | GFCWNVCVWRNGVRVCHRRCN | — |
| 313 | Y5R + V13A + V15K | GFCWRVCVYRNGARKCYRRCN | 98 |
| 314 | Y5R + V13A + Y17S | GFCWRVCVYRNGARVCSRRCN | — |
| 315 | Y5R + V15K + Y17H | GFCWRVCVYRNGVRKCHRRCN | 93 |
| 316 | Y5R + V15S + YI7H | GFCWRVCVYRNGVRSCHRRCN | 90 |
| 317 | Y5R + V15S + Y17S | GFCWRVCVYRNGVRSCSRRCN | — |
| 318 | Y5R + V6A + G12S | GFCWRACVYRNSVRVCYRRCN | — |
| 319 | Y5R + V6A + V15A | GFCWRACVYRNGVRACYRRCN | 40 |
| 320 | Y5R + V6A + V15S | GFCWRACVYRNGVRSCYRRCN | 88 |
| 321 | Y5R + V6A + Y17H | GFCWRACVYRNGVRVCHRRCN | — |
| 322 | Y5R + V6A + Y9K | GFCWRACVKRNGVRVCYRRCN | — |
| 323 | Y5R + V6C + V15S | GFCWRCCVYRNGVRSCYRRCN | — |
| 324 | Y5R + V6S + YI7H | GFCWRSCVYRNGVRVCHRRCN | — |
| 325 | Y5R + V8A + V15S | GFCWRVCAYRNGVRSCYRRCN | — |
| 326 | Y5R + V8G + Y17H | GFCWRVCGYRNGVRVCHRRCN | — |
| 327 | Y5R + V8H + G12S | GFCWRVCHYRNSVRVCYRRCN | 98 |
| 328 | Y5R + V8H + V13K | GFCWRVCHYRNGKRVCYRRCN | — |
| 329 | Y5R + V8S + V13A | GFCWVRVCSRNGARVCYRRCN | — |
| 330 | Y5R + V8S + V13S | GFCWRVCSYRNGSRVCYRRCN | — |
| 331 | Y5R + V8S + V15K | GFCWRVCSYRNGVRKCYRRCN | 95 |
| 332 | Y5R + V8S + Y9R | GFCWRVCSRENGVRVCYRRCN | — |
| 333 | Y5R + V8S + Y9S | GFCWRVCSSRNGVRVCYRRCN | — |

TABLE 1-continued

Variants exhibiting improved antimicrobial activity and reduced protein binding.
The symbol "—" means "not analyzed".

| SEQ ID NO | Substitution | Amino acid sequence | Protein binding (%) |
|---|---|---|---|
| 334 | Y5R + Y9R + V13A | GFCWRVCVRRNGARVCYRRCN | — |
| 335 | Y5R + Y9R + Y17H | GFCWRVCVRRNGVRVCHRRCN | 95 |
| 336 | Y5R + Y9S + Y17H | GFCWRVCVSRNGVRVCHRRCN | — |
| 337 | Y5R + Y9S + Y17S | GFCWRVCVSRNGVRVCSRRCN | — |
| 338 | V6A + G12S + V13K | GFCWYACVYRNSKRVCYRRCN | — |
| 339 | V6A + V13A + V15S | GFCWYACVYRNGARSCYRRCN | — |
| 340 | V6A + V13K + V15A | GFCWYACVYRNGKRACYRRCN | 98 |
| 341 | V6A + V13K + Y17H | GFCWYACVYRNGKRVCHRRCN | — |
| 342 | V6A + V15K + Y17H | GFCWYACVYRNGVRKCHRRCN | — |
| 343 | V6A + V8A + V15A | GFCWYACAYRNGVRACYRRCN | 74 |
| 344 | V6R + V8H + R10S | GFCWYRCHYSNGVRVCYRRCN | — |
| 345 | V6S + Y9R + V15S | GFCWYSCVRRNGVRSCYRRCN | — |
| 346 | V6T + Y9K + V13L | GFCWYTCVKRNGLRVCYRRCN | 86 |
| 347 | V8A + R10K + Y17H | GFCWYVCAYKNGVRVCHRRCN | — |
| 348 | V8A + V15A + Y17H | GFCWYVCAYRNGVRACHRRCN | — |
| 349 | V8A + V15S + Y17H | GFCWYVCAYRNGVRSCHRRCN | — |
| 350 | V8A + Y9R + V13A | GFCWYVCARRNGARVCYRRCN | — |
| 351 | V8A + Y9R + V15S | GFCWYVCARRNGVRSCYRRCN | — |
| 352 | V8F + G12H + Y17H | GFCWYVCFYRNHVRVCHRRCN | — |
| 353 | Y9F + V15A + Y17H | GFCWYVCVFRNGVRACHRRCN | — |
| 354 | Y9K + V13A + Y17S | GFCWYVCVKRNGARVCSRRCN | — |
| 355 | Y9R + V15S + Y17S | GFCWYVCVRRNGVRSCSRRCN | — |
| 356 | R10K + V13K + V15S | GFCWYVCVYKNGKRSCYRRCN | — |
| 357 | V13K + V15A + Y17H | GFCWYVCVYRNGKRACHRRCN | — |
| 358 | G1R + Y5N + N11H + Y17H | RFCWNVCVYRHGVRVCHRRCN | — |
| 359 | G1R + Y5N + Y17H + R19H | RFCWNVCVYRNGVRVCHRHCN | 80 |
| 360 | W4A + V6A + Y9K + V13A | GFCAYACVKRNGARVCYRRCN | — |
| 361 | W4A + Y5H + V13A + V15K | GFCAHVCVYRNGARKCYRRCN | — |
| 362 | W4A + Y5H + Y9K + V13A | GFCAHVCVKRNGARVCYRRCN | 76 |
| 363 | W4A + Y5R + V8A + Y9K | GFCARVCAKRNGVRVCYRRCN | 80 |
| 364 | W4A + Y5R + Y9K + V15S | GFCARVCVKRNGVRSCYRRCN | — |
| 365 | W4A + Y5R + Y9R + V15K | GFCARVCVRRNGVRKCYRRCN | — |
| 366 | W4A + Y5R + Y9R + V15S | GFCARVCVRRNGVRSCYRRCN | — |
| 367 | W4F + V6A + Y9R + V15S | GFCFYACVRRNGVRSCYRRCN | — |
| 368 | W4F + V8A + Y9S + V15S | GFCFYVCASRNGVRSCYRRCN | — |
| 369 | W4F + Y5H + V8A + Y17H | GFCFHVCAYRNGVRVCHRRCN | — |

TABLE 1-continued

Variants exhibiting improved antimicrobial activity and reduced protein binding.
The symbol "—" means "not analyzed".

| SEQ ID NO | Substitution | Amino acid sequence | Protein binding (%) |
|---|---|---|---|
| 370 | W4F + Y5H + V8S + V15K | GFCFHVCSYRNGVRKCYRRCN | — |
| 371 | W4F + Y5N + V6A + V15S | GFCFNACVYRNGVRSCYRRCN | — |
| 372 | W4F + Y5N + V8A + Y9R | GFCFNVCARRNGVRVCYRRCN | — |
| 373 | W4F + Y5R + V15K + Y17H | GFCFRVCVYRNGVRKCHRRCN | — |
| 374 | W4F + Y5R + V15S + Y17S | GFCFRVCVYRNGVRSCSRRCN | — |
| 375 | W4F + Y5R + V6A + Y9K | GFCFRACVKRNGVRVCYRRCN | — |
| 376 | W4F + Y5R + V6S + V13A | GFCFRSCVYRNGARVCYRRCN | — |
| 377 | W4F + Y5R + V6S + Y9R | GFCFRSCVRRNGVRVCYRRCN | 65 |
| 378 | W4F + Y5R + V8A + V15K | GFCFRVCAYRNGVRKCYRRCN | — |
| 379 | W4F + Y5R + V8A + Y17H | GFCFRVCAYRNGVRVCHRRCN | — |
| 380 | W4F + Y5R + V8A + Y9S | GFCFRVCASRNGVRVCYRRCN | — |
| 381 | W4F + Y5R + Y9K + V15K | GFCFRVCVKRNGVRKCYRRCN | 98 |
| 382 | W4F + Y9R + V15S + Y17H | GFCFYVCVRRNGVRSCHRRCN | — |
| 383 | W4G + Y5H + V15M + N21H | GFCGHVCVYRNGVRMCYRRCH | — |
| 384 | W4G + Y5K + Y9R + V13L | GFCGKVCVRRNGLRVCYRRCN | — |
| 385 | W4G + Y5R + V13K + V15A | GFCGRVCVYRNGKRACYRRCN | — |
| 386 | W4G + Y5R + V13K + V15A | GFCGRVCVYRNGKRACYRRCN | 81 |
| 387 | W4G + Y5R + V13K + V15S | GFCGRVCVYRNGKRSCYRRCN | — |
| 388 | W4G + Y5R + Y9R + V15K | GFCGRVCVRRNGVRKCYRRCN | — |
| 389 | W4T + Y5R + Y9R + V13L | GFCTRVCVRRNGLRVCYRRCN | — |
| 390 | Y5H + R10K + V13K + V15S | GFCWHVCVYKNGKRSCYRRCN | 87 |
| 391 | Y5H + V6A + Y9R + V15S | GFCWHACVRRNGVRSCYRRCN | — |
| 392 | Y5H + V8A + V13K + V15A | GFCWHVCAYRNGKRACYRRCN | — |
| 393 | Y5H + V8A + Y9K + V13L | GFCWHVCAKRNGLRVCYRRCN | — |
| 394 | Y5H + V8A + Y9R + V13A | GFCWHVCARRNGARVCYRRCN | 80 |
| 395 | Y5H + V8A + Y9R + Y17H | GFCWHVCARRNGVRVCHRRCN | — |
| 396 | Y5H + V8S + Y9K + V13L | GFCWHVCSKRNGLRVCYRRCN | 92 |
| 397 | Y5H + Y9R + V13A + V15K | GFCWHVCVRRNGARKCYRRCN | — |
| 398 | Y5H + Y9R + V13A + V15S | GFCWHVCVRRNGARSCYRRCN | — |
| 399 | Y5H + Y9R + V13A + Y17S | GFCWHVCVRRNGARVCSRRCN | — |
| 400 | Y5H + Y9S + V13L + V15K | GFCWHVCVSRNGLRKCYRRCN | — |
| 401 | Y5K + V6A + R10K + Y17H | GFCWKACVYKNGVRVCHRRCN | — |
| 402 | Y5K + V6A + V13A + V15S | GFCWKACVYRNGARSCYRRCN | — |
| 403 | Y5K + V6A + V8A + V13A | GFCWKACAYRNGARVCYRRCN | — |
| 404 | Y5K + Y9K + V13A + V15K | GFCWKVCVKRNGARKCYRRCN | — |
| 405 | Y5K + Y9R + V13A + Y17S | GFCWKVCVRRNGARVCSRRCN | — |
| 406 | Y5N + V6A + V8A + V13K | GFCWNACAYRNGKRVCYRRCN | — |

TABLE 1-continued

Variants exhibiting improved antimicrobial activity and reduced protein binding.
The symbol "—" means "not analyzed".

| SEQ ID NO | Substitution | Amino acid sequence | Protein binding (%) |
|---|---|---|---|
| 407 | Y5N + V6A + V8A + Y9R | GFCWNACARRNGVRVCYRRCN | 88 |
| 408 | Y5N + V6A + Y9R + V15S | GFCWNACVRRNGVRSCYRRCN | — |
| 409 | Y5N + V6F + N11Y + Y17H | GFCWNFCVYRYGVRVCHRRCN | — |
| 410 | Y5N + V8A + N11Q + Y17H | GFCWNVCAYRQGVRVCHRRCN | — |
| 411 | Y5N + V8A + V13K + V15A | GFCWNVCAYRNGKRACYRRCN | 86 |
| 412 | Y5N + Y9R + V13A + V15S | GFCWNVCVRRNGARSCYRRCN | — |
| 413 | Y5R + G12S + V13K + Y17H | GFCWRVCVYRNSKRVCHRRCN | — |
| 414 | Y5R + R10K + V13K + Y17H | GFCWRVCVYKNGKRVCHRRCN | — |
| 415 | Y5R + V6A + V13K + V15S | GFCWRACVYRNGKRSCYRRCN | — |
| 416 | Y5R + V6A + N15A + Y17H | GFCWRACVYRNGVRACHRRCN | — |
| 417 | Y5R + V6A + V8A + V13K | GFCWRACAYRNGKRVCYRRCN | 95 |
| 418 | Y5R + V6A + V8A + V15A | GFCWRACAYRNGVRACYRRCN | 92 |
| 419 | Y5R + V6A + V8A + Y17H | GFCWRACAYRNGVRVCHRRCN | — |
| 420 | Y5R + V6A + V8A + Y9R | GFCWRACARRNGVRVCYRRCN | — |
| 421 | Y5R + V6A + V8H + V15S | GFCWRACHYRNGVRSCYRRCN | — |
| 422 | Y5R + V6A + Y9R + V15K | GFCWRACVRRNGVRKCYRRCN | — |
| 423 | Y5R + V6S + V13A + V15S | GFCWRSCVYRNGARSCYRRCN | — |
| 424 | Y5R + V8A + G12S + V15S | GFCWRVCAYRNSVRSCYRRCN | — |
| 425 | Y5R + V8A + R10S + V13K | GFCWRVCAYSNGKRVCYRRCN | 69 |
| 426 | Y5R + V8A + V13A + Y17H | GFCWRVCAYRNGARVCHRRCN | — |
| 427 | Y5R + V8A + V13K + V15A | GFCWRVCAYRNGKRACYRRCN | — |
| 428 | Y5R + V8A + V13K + Y17H | GFCWRVCAYRNGKRVCHRRCN | — |
| 429 | Y5R + V8A + V15A + Y17H | GFCWRVCAYRNGVRACHRRCN | — |
| 430 | Y5R + V8A + V15S + Y17H | GFCWRVCAYRNGVRSCHRRCN | — |
| 431 | Y5R + V8A + Y9K + V15K | GFCWRVCAKRNGVRKCYRRCN | — |
| 432 | Y5R + V8A + Y9K + V15S | GFCWRVCAKRNGVRSCYRRCN | — |
| 433 | Y5R + V8A + Y9K + Y17H | GFCWRVCAKRNGVRVCHRRCN | — |
| 434 | Y5R + V8A + Y9R + V15S | GFCWRVCARRNGVRSCYRRCN | — |
| 435 | Y5R + V8A + Y9S + V13L | GFCWRVCASRNGLRVCYRRCN | 85 |
| 436 | Y5R + V8G + G12S + V13K | GFCWRVCGYRNSKRVCYRRCN | — |
| 437 | Y5R + V8H + G12S + V13K | GFCWRVCHYRNSKRVCYRRCN | — |
| 438 | Y5R + V8H + R10K + V13K | GFCWRVCHYKNGKRVCYRRCN | — |
| 439 | Y5R + V8H + R10S + V13K | GFCWRVCHYSNGKRVCYRRCN | 92 |
| 440 | Y5R + V8S + Y9K + V15K | GFCWRVCSKRNGVRKCYRRCN | — |
| 441 | Y5R + Y9K + V13A + V15K | GFCWRVCVKRNGARKCYRRCN | — |
| 442 | Y5R + Y9K + V15 + Y17S | GFCWRVCVKRNGVRSCSRRCN | — |

TABLE 1-continued

Variants exhibiting improved antimicrobial activity and reduced protein binding. The symbol "—" means "not analyzed".

| SEQ ID NO | Substitution | Amino acid sequence | Protein binding (%) |
|---|---|---|---|
| 443 | Y5R + Y9R + V13A + V15K | GFCWRVCVRRNGARKCYRRCN | — |
| 444 | Y5R + Y9R + V13A + V15S | GFCWRVCVRRNGARSCYRRCN | — |
| 445 | Y5R + Y9R + V13L + V15K | GFCWRVCVRRNGLRKCYRRCN | — |
| 446 | Y5R + Y9R + V13L + Y17H | GFCWRVCVRRNGLRVCHRRCN | — |
| 447 | Y5R + Y9R + V15S + Y17S | GFCWRVCVRRNGVRSCSRRCN | — |
| 448 | Y5R + Y9R + Y17S + R19H | GFCWRVCVRRNGVRVCSRHCN | — |
| 449 | Y5R + Y9S + V13A + Y17S | GFCWRVCVSRNGARVCSRRCN | — |
| 450 | V6A + V8A + Y9K + V13L | GFCWYACAKRNGLRVCYRRCN | 98 |
| 451 | V6A + Y9S + V13L + V15S | GFCWYACVSRNGLRSCYRRCN | — |
| 452 | V8A + R10S + V15S + Y17H | GFCWYVCAYSNGVRSCHRRCN | — |
| 453 | V8A + Y9R + V13L + V15S | GFCWYVCARRNGLRSCYRRCN | 92 |
| 454 | Y9K + V13A + V15K + Y17H | GFCWYVCVKRNGARKCHRRCN | 90 |
| 455 | W4A + Y5R + Y9K + V13A + V15K | GFCARVCVKRNGARKCYRRCN | — |
| 456 | W4A + Y5R + Y9K + V13A + Y17H | GFCARVCVKRNGARVCHRRCN | — |
| 457 | W4A + Y5R + Y9S + V13L + V15K | GFCARVCVSRNGLRKCYRRCN | — |
| 458 | W4A + Y9S + V13A + V15S + Y17H | GFCAYVCVSRNGARSCHRRCN | — |
| 459 | WRF + Y5H + V8A + Y94 + V15K | GFCFHVCARRNGVRKCYRRCN | — |
| 460 | W4F + Y5H + V8A + Y9R + Y17H | GFCFHVCARRNGVRVCHRRCN | — |
| 461 | W4F + Y5H + Y9K + V15K + Y17S | GFCFHVCVKRNGVRKCSRRCN | — |
| 462 | W4F + Y5K + V8S + V13L + V15K | GFCFKVCSYRNGLRKCYRRCN | — |
| 463 | W4F + Y5K + V8S + Y9K + V15K | GFCFKVCSKRNGVRKCYRRCN | — |
| 464 | W4F + Y5N + V8A + Y9R + Y17S | GFCFNVCARRNGVRVCSRRCN | — |
| 465 | W4F + Y5R + V13A + V15K + Y17S | GFCFRVCVYRNGARKCSRRCN | — |
| 466 | W4F + Y5R + V6A + V8A + Y17H | GFCFRACAYRNGVRVCHRRCN | — |
| 467 | W4F + Y5R + V6A + V8T + Y9S | GFCFRACTSRNGVRVCYRRCN | — |
| 468 | W4F + Y5R + V6A + Y9K + V13A | GFCFRACVKRNGARVCYRRCN | — |
| 469 | W4F + Y5R + V6A + Y9R + Y17H | GFCFRACVRRNGVRVCHRRCN | — |
| 470 | W4F + Y5R + V6A + Y9S + V15S | GFCFRACVSRNGVRSCYRRCN | — |
| 471 | W4F + Y5R + V6S + V8A + Y9R | GFCFRSCARRNGVRVCYRRCN | — |
| 472 | W4F + Y5R + V6S + V8A + Y9S | GFCFRSCASRNGVRVCYRRCN | — |
| 473 | W4F + Y5R + V8A + V13A + V15S | GFCFRVCAYRNGARSCYRRCN | — |
| 474 | W4F + Y5R + V8A + V13A + Y17H | GFCFRVCAYRNGARVCHRRCN | — |
| 475 | W4F + Y5R + V8A + V13A + Y17S | GFCFRVCAYRNGARVCSRRCN | — |
| 476 | W4F + Y5R + V8A + V15K + Y17H | GFCFRVCAYRNGVRKCHRRCN | — |
| 477 | W4F + Y5R + V8A + Y9K + V13A | GFCFRVCAKRNGARVCYRRCN | — |
| 478 | W4F + Y5R + V8A + Y9K + V15K | GFCFRVCAKRNGVRKCYRRCN | — |
| 479 | W4F + Y5R + V8A + Y9K + Y17H | GFCFRVCAKRNGVRVCHRRCN | — |

TABLE 1-continued

Variants exhibiting improved antimicrobial activity and reduced protein binding.
The symbol "—" means "not analyzed".

| SEQ ID NO | Substitution | Amino acid sequence | Protein binding (%) |
|---|---|---|---|
| 480 | W4F + Y5R + V8A + Y9S + V15K | GFCFRVCASRNGVRKCYRRCN | — |
| 481 | W4F + Y5R + V8S + V13A + V15S | GFCFRVCSYRNGARSCYRRCN | — |
| 482 | W4F + Y5R + V8S + V13L + V15K | GFCFRVCSYRNGLRKCYRRCN | — |
| 483 | W4F + Y5R + V8S + Y9K + V13A | GFCFRVCSKRNGARVCYRRCN | — |
| 484 | W4F + Y5R + V8S + Y9K + Y17H | GFCFRVCSKRNGVRVCHRRCN | — |
| 485 | W4F + Y5R + V8S + Y9R + V13L | GFCFRVCSRRNGLRVCYRRCN | — |
| 486 | W4F + Y5R + V8S + Y9S + V13A | GFCFRVCSSRNGARVCYRRCN | — |
| 487 | W4F + Y5R + V8S + Y9S + V15K | GFCFRVCSSRNGVRKCYRRCN | — |
| 488 | W4F + Y5R + Y9K + V13A + V15S | GFCFRVCKRNGARSCYRRCN | — |
| 489 | W4F + Y5R + Y9R + V15 + V17S | GFCFRVCVRRNGVRKCSRRCN | — |
| 490 | W4F + Y9S + V13A + V15K + Y17H | GFCFYVCVSRNGARKCHRRCN | — |
| 491 | W4G + Y5K + Y9K + V13L + V15K | GFCGKVCVKRNGLRKCYRRCN | — |
| 492 | W4G + Y5R + G12S + V13K + V15S | GFCGRVCVYRNSKRSCYRRCN | — |
| 493 | W4G + Y5R + R10K + V13K + V15A | GFCGRVCVYKNGKRACYRRCN | 77 |
| 494 | W4S + V6S + V8A + V13S + V15S | GFCSYSCAYRNGSRSCYRRCN | — |
| 495 | W4S + Y5N + V6S + Y9K + Y17S | GFCSNSCVKRNGVRVCSRRCN | — |
| 496 | W4T + Y5N + V8A + Y9K + V13A | GFCTNVCAKRNGVRVCYRRCN | — |
| 497 | Y5H + V6A + Y9R + V13A + V15S | GFCWHACVRRNGARSCYRRCN | — |
| 498 | Y5H + V6A + Y9R + V13L + V15K | GFCWHACVRRNGLRKCYRRCN | — |
| 499 | Y5H + V6A + Y9R + V13L + Y17H | GFCWHACVRRNGLRVCHRRCN | — |
| 500 | Y5H + V8A + R10K + V15A + Y17H | GFCWHVCAYKNGVRACHRRCN | — |
| 501 | Y5H + V8A + Y9R + V13L + Y17S | GFCWHVCARRNGLRVCSRRCN | — |
| 502 | Y5K + V6R + V13L + V15K + Y17H | GFCWKRCVYRNGLRKCHRRCN | — |
| 503 | Y5K + V6S + Y9R + V13L + V15S | GFCWKSCVRRNGLRSCYRRCN | — |
| 504 | Y5K + V8A + Y9R + V13A + V15S | GFCWKVCARRNGARSCYRRCN | 95 |
| 505 | Y5K + V8S + Y9S + V13L + V15S | GFCWKVCSSRNGLRSCYRRCN | — |
| 506 | Y5K + Y9S + V13A + V15K + Y17S | GFCWKVCVSRNGARKCSRRCN | — |
| 507 | Y5N + V8A + Y9R + V13L + Y17H | GFCWNVCARRNGLRVCHRRCN | — |
| 508 | Y5N + Y9R + V13L + V15K + Y17H | GFCWNVCVRRNGLRKCHRRCN | — |
| 509 | Y5R + R10S + V13K + V15S + Y17H | GFCWRVCVYSNGKRSCHRRCN | 87 |
| 510 | Y5R + V6A + R10K + G12S + V13K | GFCWRACVYKNSKRVCYRRCN | — |
| 511 | Y5R + V6A + R10K + V15A + Y17H | GFCWRACVYKNGVRACHRRCN | — |
| 512 | Y5R + V6A + V8A + V13K + V15A | GFCWRACAYRNGKRACYRRCN | — |
| 513 | Y5R + V6A + V8A + V13K + V15S | GFCWRACAYRNGKRSCYRRCN | — |
| 514 | Y5R + V6A + V8A + Y9S + Y17H | GFCWRACASRNGVRVCHRRCN | — |
| 515 | Y5R + V6A + V8S + Y9R + V13L | GFCWRACSRRNGLRVCYRRCN | — |

TABLE 1-continued

Variants exhibiting improved antimicrobial activity and reduced protein binding.
The symbol "—" means "not analyzed".

| SEQ ID NO | Substitution | Amino acid sequence | Protein binding (%) |
|---|---|---|---|
| 516 | Y5R + V6A + Y9K + V13A + Y17S | GFCWRACVKRNGARVCSRRCN | — |
| 517 | Y5R + V6A + Y9K + V13L + V15S | GFCWRACVKRNGLRSCYRRCN | — |
| 518 | Y5R + V6A + Y9R + V13A + V15S | GFCWRACVRRNGARSCYRRCN | — |
| 519 | Y5R + V6A + Y9R + V13L + V15S | GFCWRACVRRNGLRSCYRRCN | — |
| 520 | Y5R + V6A + Y9S + V13A + V15S | GFCWRACVSRNGARSCYRRCN | — |
| 521 | Y5R + V6A + Y9S + V13L + Y17S | GFCWRACVSRNGLRVCSRRCN | — |
| 522 | Y5R + V6R + Y9R + V13A + V15S | GFCWRRCVRRNGARSCYRRCN | — |
| 523 | Y5R + V8A + R10K + V13K + V15S | GFCWRVCAYKNGKRSCYRRCN | 90 |
| 524 | Y5R + V8A + Y9R + V13L + Y17H | GFCWRVCARRNGLRVCHRRCN | — |
| 525 | Y5R + V8A + Y9S + V13A + Y17S | GFCWRVCASRNGARVCSRRCN | — |
| 526 | Y5R + V8G + R10K + V15A + Y17H | GFCWRVCGYKNGVRACHRRCN | — |
| 527 | Y5R + V8G + V13K + V15A + Y17H | GFCWRVCGYRNGKRACHRRCN | — |
| 528 | Y5R + V8S + R10S + G12S + V13K | GFCWRVCSYSNSKRVCYRRCN | — |
| 529 | Y5R + V8S + Y9R + V13L + V15S | GFCWRVCSRRNGLRSCYRRCN | — |
| 530 | Y5R + Y9R + V13L + V15S + Y17S | GFCWRVCVRRNGLRSCSRRCN | — |
| 531 | Y5R + Y9S + V13A + V15K + Y17S | GFCWRVCVSRNGARKCSRRCN | — |
| 532 | Y5R + Y9S + V13L + V15S + Y17S | GFCWRVCVSRNGLRSCSRRCN | — |
| 533 | F2L + Y5R + V8A + R10S + V13K + V15A | GLCWRVCAYSNGKRACYRRCN | — |
| 534 | W4F + Y5N + Y9S + V13A + V15K + Y17H | GFCFNVCVSRNGARKCHRRCN | — |
| 535 | W4F + Y5R + V6A + V8A + Y9R + V15S | GFCFRACARRNGVRSCYRRCN | — |
| 536 | W4F + Y5R + V6A + V8S + Y9K + V13L | GFCFRACSKRNGLRVCYRRCN | — |
| 537 | W4F + Y5R + V6A + Y9K + V13L + V15K | GFCFRACVKRNGLRKCYRRCN | — |
| 538 | W4F + Y5R + V6A + Y9K + V13L + Y17H | GFCFRACVKRNGLRVCHRRCN | — |
| 539 | W4F + Y5R + V8A + Y9K + V13A + V15S | GFCFRVCAKRNGARSCYRRCN | — |
| 540 | W4F + Y5R + V8A + Y9S + V15K + Y17H | GFCFRVCASRNGVRKCHRRCN | — |
| 541 | W4F + Y5R + V8S + Y9K + V13A + V15K | GFCERVCSKRNGARKCYRRCN | — |
| 542 | W4G + Y5H + V6R + V8S + Y9R + V15K | GFCGHRCSRRNGVRKCYRRCN | — |
| 543 | W4S + Y5H + V6R + V8S + G12S + V15A | GFCSHRCSYRNSVRACYRRCN | — |
| 544 | W4S + Y5R + V8S + V13S + V15A + Y17H | GFCSRVCSYRNGSRACHRRCN | — |
| 545 | Y5R + V6A + V8A + Y9S + V13L + Y17S | GFCWRACASRNGLRVCSRRCN | — |
| 546 | W4S + Y5N + V6R + V8H + R10S + V13S + V15A + Y17H | GFCSNRCHYSNGSRACHRRCN | — |
| 547 | Y5G + V6A + C7V + V8N + R10T + N11S + G12N + V13C + V15A + Y17K | GFCWGAVNYTSNCRACKRRCN | — |
| 548 | F2S + Y56 + V6A + C7V + V8N + R10T + N11S + G12N + V13C + V15A + Y17K | GSCWGAVNYTSNCRACKRRCN | — |

Example 2

Efficacy of NZ17074 Against *Escherichia coli* AID#172 in the Neutropenic Murine Peritonitis/Sepsis Model and Estimation of ED50

Introduction

The purpose of this study was to investigate the dose-response relationship following intravenous (i.v.) administration of a single dose of NZ17074 ranging from 0.16-12 mg/kg. The effect was tested against *E. coli* AID#172 in the neutropenic peritonitis model Treatment with 40 mg/kg meropenem was included as a positive control group. The colony counts in blood and peritoneal fluid were determined at 5 hours after treatment.

The murine peritonitis/sepsis model is a well-recognized model for studies of antimicrobial activity as described by N. Frimodt-Møller and J. D. Knudsen in Handbook of Animal Models of Infection (1999), ed. by O. Zak & M. A. Sande, Academic Press, San Diego, US.

Materials and Methods
- 30 outbred, NMRI female mice, 25-30 grams (Harlan Scandinavia)
- *E. coli* AID#172 from Statens Serum Instute, Copenhagen, Denmark. Clinical isolate from a human wound from 2003. Multiresistant (Ampicillin, Ceftazidime, Aztreonam, Gentamicin, Ciprofloxacin)
- NZ17074 in Ringer Acetate, pH 6: 1.2 mg/ml, 6.0 ml. The solution was stored at 4° C. until use. Analyses of the dose formulations used were performed after completion of the in-life phase of the study and gave the following results:

| Intended concentration | Measured concentration |
|---|---|
| 1.2 mg/ml | 1.11 mg/ml |
| 0.6 mg/ml | 0.51 mg/ml |
| 0.3 mg/ml | 0.24 mg/ml |
| 0.15 mg/ml | 0.14 mg/ml |
| 0.075 mg/ml | 0.043 mg/ml |
| 0.03 mg/ml | 0.010 mg/ml |
| 0.016 mg/ml | 0.002 mg/ml |

- Vehicle (Ringer Acetate pH 6). The solution was stored at 4° C. until use
- MERONEM® (AstraZeneca, 500 mg infusion substance, meropenem). Lot no. 09466C. Date of expire: 08-2013
- Water, sterile
- 0.9% saline, sterile
- Cyclophosphamide, (APODan®, A-Pharma, 1 g) Batch nr. 928491 Date of expire: 05-2012
- 5% Horse Blood Agar plates
- Lactose bromthymol blue agar plates Laboratory Animal Facilities and Housing of Mice The temperature and humidity were registered daily in the animal facilities. The temperature was 21+/−2° C. and can be regulated by heating and cooling. The humidity was 55+/− 10%. The air changes per hour were approximately 10-20 times, and light/dark period was in 12-hours interval of 6 a.m.-6 p.m./6 p.m-6 a.m.

The mice had free access to domestic quality drinking water and food (2016, Harlan). The mice were housed in Type 3 macrolone cages with 3 mice/cage. The bedding was Aspen Wood from Tapvei. Further the animals were offered paper strands from Sizzle-nest as nesting material. Mice were marked on the tail for individual identification within the cage. Mice were weighed the day before dosing.

Preparation of NZ17074 Solutions

The solution of 1.2 mg/ml was further diluted in PBS vehicle as follows:

| | |
|---|---|
| 0.6 mg/ml~7.5 mg/kg: | 1.5 ml of 1.2 mg/ml NZ17074 + 1.5 ml vehicle |
| 0.3 mg/ml~5.0 mg/kg: | 1.5 ml of 0.6 mg/ml NZ17074 + 1.5 ml vehicle |
| 0.15 mg/ml~2.5 mg/kg: | 1.5 ml of 0.3 mg/ml NZ17074 + 1.5 ml vehicle |
| 0.075 mg/ml~1.25 mg/kg: | 1.5 ml of 0.15 mg/ml NZ17074 + 1.5 ml vehicle |
| 0.03 mg/ml~0.63 mg/kg: | 1.5 ml of 0.075 mg/ml NZ17074 + 2.25 ml vehicle |
| 0.016 mg/ml~0.16 mg/kg: | 1.5 ml of 0.03 mg/ml NZ17074 + 1.5 ml vehicle |

Preparation Meropenem Solution

Treatment with meropenem 40 mg/kg was included as a positive control group. A total of 500 mg meropenem (one ampoule) was dissolved in 10 ml water~50 mg/ml This stock solution was further diluted to 4 mg/ml (0.4 ml 50 mg/ml+4.6 ml saline).

Preparation of Cyclophosphamide

A total of 1 g cyclophosphamide (one ampoule APO-DAN®, A-Pharma, 1 g), was dissolved in 50 ml water. ~20 mg/ml on each day of use. This stock solution was further diluted to 11 mg/ml (16.5 ml 20 mg/ml+13.5 ml saline) for use on day −4 or to 5 mg/kg (8.25 ml 20 mg/ml+21.75 ml saline)) for use on day −1.

Treatment of Mice with Cyclophosphamide

The mice were rendered neutropenic by injecting 0.5 ml cyclophosphamide solution intraperitoneally 4 days (200 mg/kg) and 1 day (100 mg/kg) prior to inoculation.

Inoculation of Mice

Fresh overnight *E. coli* AID#172 colonies from a 5% Horse Blood Agar plate were suspended and diluted in sterile saline to approximately $2 \times 10^8$ CFU/ml. One hour before start of treatment (time −1 hr) mice were inoculated intraperitoneally with 0.5 ml of the *E. coli* suspension in the lateral lower quadrant of the abdomen. Approximately ½-1 hour after treatment, mice were treated orally with 45 microliters neurophen (20 mg ibuprofen/ml corresponding to 30 mg/kg) as a pain relief.

Treatment of Mice

The mice were treated iv. in the lateral tail vein over approximately 30 seconds with 10 ml/kg with a single dose of NZ17074, meropenem or vehicle at time 0 hour (see Table 1). The dosing was based on a mean weight of 30 g. Mice that weighed 28-32 g received 0.30 ml solution. Mice that weighed 27-28 g received 0.25 ml solution and mice that weighed 32.1-36 g received 0.35 ml solution.

TABLE 1

Treatment and sampling schedule in the murine peritonitis model.

| Inoculation | Intravenous treatment at 0 hr | Sampling and mouse no. | |
|---|---|---|---|
| | | 0 hour | 5 hours |
| i.p. at − 1 hr | | | |
| 0.5 ml of | Vehicle, Ringer acetate | | 1-2-3 |
| *E. coli* | NZ17074 0.16 mg/kg | | 4-5-6 |
| AID#172 | NZ17074 0.30 mg/kg | | 7-8-9 |
| $1 \times 10^6$ CFU/ml | NZ17074 0.75 mg/kg | | 10-11-12 |
| | NZ17074 1.5 mg/kg | | 13-14-15 |
| | NZ17074 3.0 mg/kg | | 16-17-18 |
| | NZ17074 6.0 mg/kg | | 19-20-21 |
| | NZ17074 12 mg/kg | | 22-23-24 |

TABLE 1-continued

Treatment and sampling schedule in the murine peritonitis model.

| Inoculation | | Sampling and mouse no. | |
|---|---|---|---|
| i.p. at - 1 hr | Intravenous treatment at 0 hr | 0 hour | 5 hours |
| | meropenem 40 mg/kg | | 25-26-27 |
| | No treatment | 28-29-30 | |

T indicates the time in relation to treatment. Numbers in the sampling columns are mouse identification numbers.

Clinical Scoring of Mice

The mice were observed during the study and scored 0-5 based on their behaviour and clinical signs.

Score 0: Healthy.

Score 1: Minor clinical signs of infection and inflammation e.g. observations of minor signs of distress or changed activity.

Score 2: Clear signs of infection like, social withdrawal, lack of curiosity, changed body position, piloerection, or changes in pattern of movement.

Score 3: Severe signs of infection like stiff movements, lack of curiosity, changed body position, piloerection, pain, or changes in pattern of movement.

Score 4: Severe pain and the mouse was sacrificed immediately to minimize the suffering of the animal.

Score 5: The mouse was dead.

Sampling

Colony counts were determined from blood and peritoneal fluid at 0 and 5 hours. The mice were anaesthetized with $CO_2+O_2$ and blood was collected from axillary cutdown in 1.5 ml EDTA coated eppendorf tubes. The mice were sacrificed immediately after blood sampling and a total of 2 ml sterile saline was injected i.p. and the abdomen gently massaged before it was opened and fluid sampled with a pipette. Each sample was then 10 fold diluted in saline and 20-microliter spots were applied on blue agar plates. All agar plates were incubated 18-22 hours at 35° C. in ambient air.

Results

The colony counts were performed at the start of treatment and 5 hours after treatment. The CFU counts and the clinical score of the mice are shown in Table 3. The CFU lumbers are $log_{10}$ transformed before performing calculations.

The CFU/ml in the inoculum was determined to 6.29 $log_{10}$. At start of treatment the mean $log_{10}$ CFU/ml in peritoneal fluid was 5.76 and in blood 5.13 and the CFU levels remained at a similar level in the vehicle group (5.72 and 4.65 $log_{10}$ CFU/ml in the peritoneum and blood respectively) at 5 hours after treatment. Slightly lower CFU levels were observed in blood and peritoneal fluid after treatment with NZ17074 0.16-3.0 mg/kg. Treatment with 6 and 12 mg/kg NZ17074 resulted in CFU levels significantly lower (p<0.001) than after vehicle treatment both in peritoneal fluid and in blood (Table 3). Also the meropenem treatment, 40 mg/kg, resulted in significant reduction compared to the vehicle treated mice both in blood (p<0.05) and peritoneal fluid (p<0.01).

The dose-response curves (data not shown) were calculated in GraphPad Prism using Sigmoidal dose-response (variable slope). From these ED50 values were determined to 3.09±2.07 mg/kg in peritoneal fluid and 3.17±0.53 mg/kg in blood.

The maximum effect of NZ17074, $E_{max}$ was defined as the log CFU difference between no response and maximum response. No response was characterised as colony counts at the same level as determined for vehicle treated mice. The $E_{max}$ was calculated as the difference between the "Top plateau" and "Bottom plateau" in GraphPad Prism using Sigmoidal dose-response to be 4.72 $log_{10}$ CFU for the peritoneal fluid and 3.15 $log_{10}$ CFU for the blood.

In addition the 1, 2 and 3 log killing, defined as the dose required to obtain 1, 2 or 3 log reduction in bacterial loads compared to start of treatment, were estimated using GraphPad Prism. The 1, 2 and 3 log killing of NZ17074 was 1.11 mg/kg, 2.95 mg/kg and 4.73 mg/kg respectively in peritoneal fluid and 0.25 mg/kg, 2.75 mg/kg and 3.78 mg/kg respectively in blood.

No or only mild clinical score was observed in all of the treatment groups (Table 3).

Discussion and Conclusion

The purpose of this study was to investigate the dose-response relationship following intravenous (i.v.) administration of a single dose of NZ17074 ranging from 0.18-12 mg/kg. The effect was tested against *E. coli* AID#172 in the neutropenic peritonitis/sepsis model.

The ED50 values for NZ17074 were determined to 3.09±2.07 mg/kg in the peritoneal fluid and 3.17±0.53 mg/kg in the blood. The 1 log killing was estimated to be 1.11 mg/kg in the peritoneal fluid and 0.25 mg/kg in the blood. The 2 log killing was estimated to be 2.95 mg/kg in the peritoneal fluid and 2.76 mg/kg in the blood. The 3 log killing was estimated to be 4.73 mg/kg in the peritoneal fluid and 3.78 mg/kg in the blood.

TABLE 2

Efficacy values for NZ17074 against *E. coli* AID#172 calculated in Graph Pad Prism.

| NZ17074 | Peritoneal fluid | Blood |
|---|---|---|
| TOP | 0.325 CFU/ml | −0.985 CFU/ml |
| BOTTOM | −4.486 CFU/ml | −4.138 CFU/ml |
| Emax | 4.811 CFU/ml | 3.153 CFU/ml |
| ED50 | 3.086 mg/kg | 3.168 mg/kg |
| $R^2$ | 0.7524 | 0.6889 |
| 1 log killing | 1.11 mg/kg | 0.25 mg/kg |
| 2 log killing | 2.95 mg/kg | 2.76 mg/kg |
| 3 log killing | 4.73 mg/kg | 3.78 mg/kg |

TABLE 3

Colony counts of *E. coli* AID#172 in blood and peritoneal fluid from neutropenic mice treated with a single dose of NZ17074, meropenem or vehicle.

| Treatment T = 0 hour | Mouse no. | Time | Clinical score T = 0 hour | Clinical score T = 5 hours | $log_{10}$ CFU PF | mean PF | $log_{10}$ CFU Blood | mean Blood |
|---|---|---|---|---|---|---|---|---|
| Vehicle | 1 | T = 5 | 1 | 1 | 5.74 | 5.72 | 5.05 | 4.65 |
| | 2 | T = 5 | 1 | 0 | 5.54 | | 4.78 | |
| | 3 | T = 5 | 1 | 1 | 5.88 | | 4.11 | |

TABLE 3-continued

Colony counts of *E. coli* AID#172 in blood and peritoneal fluid from neutropenic mice treated with a single dose of NZ17074, meropenem or vehicle.

| Treatment T = 0 hour | Mouse no. | Time | Clinical score T = 0 hour | Clinical score T = 5 hours | log₁₀ CFU PF | log₁₀ CFU mean PF | log₁₀ CFU Blood | log₁₀ CFU mean Blood |
|---|---|---|---|---|---|---|---|---|
| NZ17074 | 4 | T = 5 | 1 | 1 | 5.16 | 5.31 | 4.27 | 4.54 |
| 0.16 mg/kg | 5 | T = 5 | 1 | 1 | 4.78 | | 4.19 | |
| | 6 | T = 5 | 1 | 0 | 5.98 | | 5.18 | |
| NZ17074 | 7 | T = 5 | 1 | 0 | 2.76 | 4.26 | 1.40 | 2.88 |
| 0.30 mg/kg | 8 | T = 5 | 1 | 1 | 5.74 | | 4.63 | |
| | 9 | T = 5 | 1 | 0 | 4.27 | | 2.60 | |
| NZ17074 | 10 | T = 5 | 1 | 0 | 5.74 | 5.16 | 5.07 | 4.46 |
| 0.75 mg/kg | 11 | T = 5 | 1 | 1 | 4.95 | | 4.30 | |
| | 12 | T = 5 | 1 | 1 | 4.78 | | 4.00 | |
| NZ17074 | 13 | T = 5 | 1 | 0 | 3.33 | 4.41 | 3.51 | 3.99 |
| 1.5 mg/kg | 14 | T = 5 | 1 | 1 | 4.72 | | 3.92 | |
| | 15 | T = 5 | 1 | 0 | 5.18 | | 4.54 | |
| NZ17074 | 16 | T = 5 | 1 | 1 | 4.74 | 3.91 | 3.86 | 2.81 |
| 3.0 mg/kg | 17 | T = 5 | 1 | 1 | 4.74 | | 3.57 | |
| | 18 | T = 5 | 1 | 0 | 2.24 | | 1.00 | |
| NZ17074 | 19 | T = 5 | 1 | 1 | 2.18 | 2.12*** | 1.00 | 1.00*** |
| 8.0 mg/kg | 20 | T = 5 | 1 | 1 | 2.18 | | 1.00 | |
| | 21 | T = 5 | 1 | 1 | 2.00 | | 1.00 | |
| NZ17074 | 22 | T = 5 | 1 | 1 | 1.00 | 1.36*** | 1.00 | 1.00*** |
| 12 mg/kg | 23 | T = 5 | 1 | 0 | 1.69 | | 1.00 | |
| | 24 | T = 5 | 1 | 0 | 1.40 | | 1.00 | |
| Meropenem | 25 | T = 5 | 1 | 1 | 3.92 | 2.64** | 2.48 | 2.38* |
| 40 mg/kg | 26 | T = 5 | 1 | 1 | 1.70 | | 1.70 | |
| | 27 | T = 5 | 1 | 0 | 2.30 | | 2.95 | |
| | 28 | T = 0 | 1 | | 5.84 | 5.78 | 5.08 | |
| None | 29 | T = 0 | 1 | | 5.78 | | 4.98 | 5.13 |
| | 30 | T = 0 | 1 | | 5.65 | | 5.34 | |

Stars indicate significantly different from vehicle group (Anova; multiple comparison).
*corresponds to $p < 0.05$;
**corresponds to $p < 0.01$;
***corresponds to $p < 0.001$.
Detection limit 1.4 log₁₀ CFU/ml. Samples with no detectable bacteria is presented as 1.0 log₁₀ CFU/ml.

Example 3

Peritonitis/Sepsis Model: Effect Over Time of 7.5 mg/kg NZ17074 Against *Escherichia coli* AID#172 in Neutropenic NMRI Mice Introduction The purpose of this study was to investigate the in vivo efficacy of NZ17074 following intravenous (i.v.) administration of a single dose of 7.5 mg/kg. The effect was tested against *Escherichia coli* AID#172 in the peritonitis model in neutropenic NMRI mice to avoid the use of mucin as normally applied in the murine peritonitis model. The mice were rendered neutropenic by cyclophosphamide injections. Treatment with 40 mg/kg meropenem was included as a positive control group and treatment with vehicle was included as a negative control group. The colony counts in peritoneal fluid and blood were determined at 2 and 5 hours after treatment.

Materials and Methods 30 outbred, NMRI female mice, 28-32 grams (Harlan Scandinavia)

*Escherichia coli* AID#172 from Statens Serum Instute, Copenhagen, Denmark. Clinical isolate from a human wound from 2003. Multiresistant (Ampicillin, Ceftazidime, Aztreonam, Gentamicin, Ciprofloxacin)

NZ17074 in Ringer Acetate pH 6, 1.2 ml 0.75 mg/ml. Analyses of the dose formulation performed after the study showed a concentration of approx. 0.78 mg/ml.

Vehicle (Ringer Acetate pH 6) 3 ml.

MERONEM® (AstraZeneca, 500 mg infusion substance, meropenem). Lot no. 09466C Date of expire: 08-2013

APODAN® (A-Pharma, 1 g cyclophosphamide) Batch nr. 928491 Date of expire: 05-2012

Water, sterile 0.9% saline, sterile

5% Horse Blood Agar plates

Lactose bromthymol blue agar plates

Laboratory Animal Facilities and Housing of Mice

The temperature and humidity were registered daily in the animal facilities. The temperature was 21+/−2° C. and can be regulated by heating and cooling. The humidity was 55+/−10%. The air changes per hour were approximately 10-20 times, and light/dark period was in 12-hours interval of 6 a.m.-6 p.m./6 p.m.-6 a.m. The mice had free access to domestic quality drinking water and food (2016, Harlan). The mice were housed in Type 3 macrolone cages with 3 mice/cage. The bedding was Aspen Wood from Tapvei. Further the animals were offered paper strands from Sizzle-nest as nesting material. Mice were marked on the tail for individual identification within the cage.

NZ17074 Solution

A solution of 0.75 mg/ml of each test compound was stored at +4° C. until one hour before injection, thereafter at room temperature.

Preparation of Meropenem Solution

A total of 500 mg meropenem (one ampoule) was dissolved in 10 ml water~50 mg/ml the day of use. This stock solution was further diluted to 4 mg/ml (0.4 ml 50 mg/ml+4.6 ml saline).

Preparation of Cyclophosphamide

A total of 1 g cyclophosphamide (one ampoule Apodan) was dissolved in 50 ml water~20 mg/ml on each day of use.

This stock solution was further diluted to 11 mg/ml (16.5 ml of 20 mg/ml+13.5 ml saline) for use on day −4 or to 5.5 mg/ml (8.25 ml of 20 mg/ml+21.75 ml saline) for use on day −1.

Treatment of Mice with Cyclophosphamide

The mice were rendered neutropenic by injecting 0.5 ml cyclophosphamide solution intraperitoneally 4 days (200 mg/kg) and 1 day (100 mg/kg) prior to inoculation.

Inoculation of Mice

Fresh overnight *E. coli* AID#172 colonies from a 5% Horse Blood Agar plate were suspended and diluted in sterile saline to approximately $2 \times 10^6$ CFU/ml.

One hour before start of treatment (time −1 hour) mice were inoculated intraperitoneally with 0.5 ml of the *E. coli* suspension in the lateral lower quadrant of the abdomen.

2.5 hours after treatment, when clinical signs of infection were significant, mice were treated orally with 45 microliters neurophen (20 mg ibuprofen/ml, corresponding to 30 mg/kg) as a pain relief.

Scoring of Mice

The mice were clinically scored for signs of infection at the time of each sampling.

Score 0: Healthy.
Score 1: Minor clinical signs of infection and inflammation e.g. observations of minor signs of distress or changed activity.
Score 2: Clear signs of infection like, social withdrawal, lack of curiosity, changed body position, piloerection, or changes in pattern of movement.
Score 3: Severe signs of infection like stiff movements, lack of curiosity, forced ventilation, changed body position, piloerection, pain, or changes in pattern movement.
Score 4: Severe pain and the mouse was sacrificed immediately to minimize the suffering of the animal.
Score 5: The mouse was dead.

Treatment of Mice

The mice were treated i.v. in the lateral tail vein over approximately 30 seconds with a single dose of NZ17074, meropenem or vehicle at time 0 hour (see Table 1). The dosing was based on a mean weight of 30 g. Mice that weighed 28-32 g received 0.30 ml solution. Mice that weighed 27-28 g received 0.25 ml solution and mice that weighed 32.1-36 g received 0.35 ml solution. Mouse 17 accidentally received 0.35 ml although it weighed 29.5 g. This does not seem to have influenced the results as the CFU levels in this mouse was very similar to the other two mice in the group.

TABLE 4

Treatment and sampling schedule in the murine peritonitis model.

| Inoculation T = −1 hour | Treatment T = 0 hour | Sampling T = 0 hour | Sampling T = 2 hours | Sampling T = 5 hours |
|---|---|---|---|---|
| 0.5 ml of *E. coli* AID#172 $10^6$ CFU/ml | NZ17074 | | | 4, 5, 6 |
| | Meropenem | | | 7, 8, 9 |
| | Vehicle (Ringer Acetate) | | | 10, 11, 12 |
| | NZ17074 | | 16, 17, 18 | |
| | Meropenem | | 19, 20, 21 | |
| | Vehicle (Ringer Acetate) | | 22, 23, 24 | |
| | None | | 25, 26, 27 | |
| | None | 28, 29, 30 | | |

T indicates the time in relation to treatment. Numbers in the sampling columns are mouse identification numbers.

Sampling

Colony counts were determined from blood and peritoneal fluid at 0, 2 and 5 hours after treatment according to Table 1.

The mice were anesthetized with $O_2+CO_2$ and blood was collected by axillary cut down. The mice were sacrificed by cervical dislocation and a total of 2 ml sterile saline was injected i.p. and the abdomen gently massaged before it was opened and fluid sampled with a pipette. Each sample was 10 fold diluted in saline and 20-microliter spots were applied on blood agar plates. All agar plates were incubated 18-22 hours at 35° C. in ambient air.

Results

The colony counts and the clinical scores of the mice are shown in Table 2. The CFU numbers are $\log_{10}$ transformed before performing calculations to obtain a normal distribution.

The CFU/ml in the inoculum was determined to 6.30 $\log_{10}$. At start of treatment the mean $\log_{10}$ CFU/ml in the peritoneal fluid was 3.57 and in the blood 3.54 and the CFU level increased to 5.43 and 4.58 in the peritoneal fluid and the blood respectively after 2 hours in vehicle treated animals and to 5.72 and 4.74 in the peritoneal fluid and the blood respectively after 5 hours in vehicle treated mice, which was as expected.

At 2 hours after treatment with NZ17074 significantly lower CFU levels were observed both in the blood and the peritoneal fluid compared to the vehicle treatment ($p<0.001$).

A further reduction of the CFU levels was observed at 5 hours after treatment with NZ17074 both in the blood and in the peritoneal fluid ($p<0.001$ compared to vehicle control). The CFU levels were more the 3 $\log_{10}$ CFU/ml lower than after vehicle treatment.

Also meropenem treatment resulted in significantly ($p<0.01$) reduced CFU levels compared to vehicle treatment in the peritoneal fluid at both 2 and 5 hours after treatment but in the blood only at 5 hours after treatment. The lack of significance in the blood at 2 hours after treatment may reflect the large variability in the vehicle group rather than poor effect of meropenem.

The difference in CFU levels after NZ17074 or meropenem treatment compared to vehicle treatment was:

| NZ17074, 7.5 mg/kg | 2 hours: peritoneum −1.63 log cfu/ml | blood −2.50 log cfu/ml |
|---|---|---|
| | 5 hours: peritoneum −3.76 log cfu/ml | blood −3.74 log cfu/ml |
| Meropenem 40 mg/kg | 2 hours: peritoneum −1.51 log cfu/ml | blood −0.82 log cfu/ml |
| | 5 hours: peritoneum −1.51 log cfu/ml | blood −1.64 log cfu/ml |

All mice had only mild or no symptoms of infection (Table 2).

Discussion and Conclusion

The purpose of this study was to investigate the efficacy of NZ17074 following intravenous (i.v.) administration of a single dose of 7.5 mg/kg in the neutropenic peritonitis model in NMRI mice. A significant ($p<0.001$) reduction of more the 3 $\log_{10}$ CFU/ml compared to vehicle treatment was observed for NZ17074 in blood and peritoneal fluid at 5 hours after treatment. Also at 2 hours after treatment with NZ17074 a significant reduction ($p<0.001$) both in the blood and peritoneal fluid was observed. Meropenem showed a significant reduction compared to the vehicle group ($p<0.01$) both in the blood and in the peritoneal fluid at 5 hours but at 2 hours after treatment only in the peritoneal fluid.

TABLE 5

Colony counts of E. coli AID#172 in mice treated with a single dose of NZ17074, vehicle or meropenem

| Treatment | id no. | Time of sampling | T = 0 hour | T = 2 hours | T = 5 hours | PF | mean PF | Blood | Mean Blood |
|---|---|---|---|---|---|---|---|---|---|
| NZ17074 | 4 | T = 5 | 0 | | 0 | 2.18 | 1.96*** | 1.00 | 1.00*** |
| 7.5 mg/kg | 5 | T = 5 | 0 | | 1 | 2.30 | | 1.00 | |
| | 6 | T = 5 | 0 | | 1 | 1.40 | | 1.00 | |
| Meropenem | 7 | T = 5 | 0 | | 0 | 4.38 | 4.21** | 3.20 | 3.10** |
| 40 mg/kg | 8 | T = 5 | 0 | | 0 | 4.00 | | 2.85 | |
| | 9 | T = 5 | 0 | | 0 | 4.26 | | 3.26 | |
| | 10 | T = 5 | 0 | | 0 | 5.39 | 5.72 | 4.63 | 4.74 |
| Vehicle | 11 | T = 5 | 0 | | 0 | 5.99 | | 5.24 | |
| | 12 | T = 5 | 0 | | 0 | 5.78 | | 4.36 | |
| NZ17074 | 16 | T = 2 | 0 | 1 | | 4.24 | 3.79** | 2.04 | 2.08** |
| 7.5 mg/kg | 17 | T = 2 | 0 | 1 | | 3.60 | | 2.20 | |
| | 18 | T = 2 | 0 | 1 | | 3.54 | | 2.00 | |
| Meropenem | 19 | T = 2 | 0 | 1 | | 4.12 | 3.92** | 3.60 | 3.76 |
| 40 mg/kg | 20 | T = 2 | 0 | 1 | | 3.40 | | 3.57 | |
| | 21 | T = 2 | 0 | 1 | | 4.24 | | 4.11 | |
| Vehicle | 22 | T = 2 | 0 | 0 | | 4.89 | 5.43 | 3.21 | 4.58 |
| | 23 | T = 2 | 0 | 1 | | 5.65 | | 5.39 | |
| | 24 | T = 2 | 0 | 0 | | 5.74 | | 5.15 | |
| None | 25 | T = 2 | 0 | 0 | | 4.45 | 5.08 | 4.39 | 4.33 |
| | 26 | T = 2 | 0 | 0 | | 5.42 | | 4.57 | |
| | 27 | T = 2 | 0 | 0 | | 5.38 | | 4.02 | |
| None | 28 | T = 0 | 0 | | | 1.88 | 3.57 | 1.00 | 3.54 |
| | 29 | T = 0 | 0 | | | 3.71 | | 4.27 | |
| | 30 | T = 0 | 0 | | | 5.13 | | 5.35 | |

PF: peritoneal fluid. Used inoculum: $1.97 \times 10^6$ CFU/ml.
Mouse received 0.35 ml instead of 0.30 ml of test compound
*p < 0.05,
**p < 0.01,
***p < 0.001 compared to vehicle group.

Example 4

Neutropenic Thigh Infection Model

Efficacy of NZ17074 Against *Escherichia coli* AID#72 and Estimation of ED50

Introduction

The purpose of this study was to investigate the dose-response relationship following intravenous (i.v.) administration of a single dose of NZ17074 ranging from 0.16-12 mg/kg. The effect was tested against *E. coli* AID#172 in the neutropenic thigh model. Treatment with 40 mg/kg meropenem was included as a positive control group. The colony counts in thighs were determined at 5 hours after treatment.

The thigh infection model is a well-recognized model for studies of antimicrobial effect and tissue penetration as described by S. Gudmundsson & H. Erlensdóttir Handbook of Animal Models of Infection (1999), ed. by O. Zak & M. A. Sande, Academic Press, San Diego, US and in several publications. Reviewed by D. Andes & C. Craig: Animal model pharmacokinetics and pharmacodynamics: a critical review. *International Journal of Antimicrobial Agents* 19(4): 261-268.

Materials and Methods 40 outbred, NMRI female mice, 25-30 grams (Harlan Scandinavia)

*E. coli* AID#172 from Statens Serum Instute, Copenhagen, Denmark: Clinical isolate from a human wound from 2003. Multiresistant (Ampicillin, Ceftazidime, Aztreonam, Gentamicin, Ciprofloxacin)

NZ17074 in Ringer Acetate, pH 6: 1.2 mg/ml, 6.0 ml. The solution was stored at 4° C. until use. Analyses of the dose formulations used were performed after completion of the in-life phase of the study and gave the following results:

| Intended concentration | Measured concentration |
|---|---|
| 1.2 mg/ml | 1.11 mg/ml |
| 0.6 mg/ml | 0.51 mg/ml |
| 0.3 mg/ml | 0.24 mg/ml |
| 0.15 mg/ml | 0.14 mg/ml |
| 0.075 mg/ml | 0.043 mg/ml |
| 0.03 mg/ml | 0.010 mg/ml |
| 0.016 mg/ml | 0.002 mg/ml |

Vehicle (Ringer Acetate pH 6). The solution was stored at 4° C. until use

MERONEM® (AstraZeneca, 500 mg infusion substance, meropenem). Lot no. 09466C. Date of expire: 08-2013

Water, sterile 0.9% saline, sterile

SENDOXAN® (Cyclophosphamide, Baxter, 1 g) Batch nr. 0A671C Date of expire: 01-2013

5% Horse Blood Agar plates

Lactose bromthymol blue agar plates

Laboratory Animal Facilities and Housing of Mice

The temperature and humidity were registered daily in the animal facilities. The temperature was 21+/−2° C. and can be regulated by heating and cooling. The humidity was 55+/−10%. The air changes per hour were approximately 10-20 times, and light/dark period was in 12-hours interval of 6 a.m.-6 p.m./6 p.m.-6 a.m.

The mice had free access to domestic quality drinking water and food (2016, Harlan). The mice were housed in Type 3 macrolone cages with 4 mice/cage. The bedding was Aspen Wood from Tapvei. Further the animals were offered paper strands from Sizzle-nest as nesting material. Mice were marked on the tail for individual identification within the cage. Mice were weighed the day before dosing.

Preparation of NZ17074 Solutions

The solution of 1.2 mg/ml was further diluted in PBS vehicle as follows:

| | |
|---|---|
| 0.6 mg/ml~7.5 mg/kg: | 1.5 ml of 1.2 mg/ml NZ17074 + 1.5 ml vehicle |
| 0.3 mg/ml~5.0 mg/kg: | 1.5 ml of 0.6 mg/ml NZ17074 + 1.5 ml vehicle |
| 0.15 mg/ml~2.5 mg/kg: | 1.5 ml of 0.3 mg/ml NZ17074 + 1.5 ml vehicle |
| 0.075 mg/ml~1.25 mg/kg: | 1.5 ml of 0.15 mg/ml NZ17074 + 1.5 ml vehicle |
| 0.03 mg/ml~0.63 mg/kg: | 1.5 ml of 0.075 mg/ml NZ17074 + 2.25 ml vehicle |
| 0.016 mg/ml~0.16 mg/kg: | 1.5 ml of 0.03 mg/ml NZ17074 + 1.5 ml vehicle |

Preparation Meropenem Solution

Treatment with meropenem 40 mg/kg was included as a positive control group.

A total of 500 mg meropenem (one ampoule) was dissolved in 10 ml water~50 mg/ml This stock solution was further diluted to 4 mg/ml (0.4 ml 50 mg/ml+4.6 ml saline).

Preparation of Cyclophosphamide

A total of 1 g cyclophosphamide (one ampoule SENDOXAN® 1 g, Baxter) was dissolved in 50 ml water ~20 mg/ml on each day of use. This stock solution was further diluted to 11 mg/ml (16.5 ml 20 mg/ml+13.5 ml saline) for use on day −4 or to 5 mg/kg (8.25 ml 20 mg/ml+21.75 ml saline)) for use on day −1.

Treatment of Mice with Cyclophosphamide

The mice were rendered neutropenic by injecting 0.5 ml cyclophosphamide solution intraperitoneally 4 days (200 mg/kg) and 1 day (100 mg/kg) prior to inoculation.

Inoculation of Mice

Fresh overnight *E. coli* AID#172 colonies from a 5% Horse Blood Agar plate were suspended and diluted in sterile saline to approximately $2 \times 10^7$ CFU/ml. One hour before start of treatment (time −1 hour) mice were inoculated intramuscularly with 0.05 ml of the *E. coli* suspension in the left hind leg. Approximately ½ hour before inoculation mice were treated orally with 45 microliters neurophen (20 mg ibuprofen/ml corresponding to 30 mg/kg) as a pain relief.

Treatment of Mice

The mice were treated i.v. in the lateral tail vein over approximately 30 seconds with 10 ml/kg with a single dose of NZ17074, meropenem or vehicle at time 0 hour (see Table 1). The dosing was based on a mean weight of 30 g. Mice that weighed 28-32 g received 0.30 ml solution. Mice that weighed 27-28 g received 0.25 ml solution and mice that weighed 32.1-36 g received 0.35 ml solution.

TABLE 6

Treatment and sampling schedule in the murine thigh model.

| Inoculation | Intravenous treatment | Sampling and mouse no. | |
|---|---|---|---|
| i.m. at −1 hr | at 0 hr | 0 hr | 5 hours |
| 0.05 ml of *E. coli* AID#172 | Vehicle, Ringer acetate | | 1-2-3-4 |
| | NZ17074 0.16 mg/kg | | 5-6-7-8 |
| | NZ17074 0.30 mg/kg | | 9-10-11-12 |

TABLE 6-continued

Treatment and sampling schedule in the murine thigh model.

| Inoculation | Intravenous treatment | Sampling and mouse no. | |
|---|---|---|---|
| i.m. at −1 hr | at 0 hr | 0 hr | 5 hours |
| $2 \times 10^7$ CFU/ml | NZ17074 0.75 mg/kg | | 13-14-15-16 |
| | NZ17074 1.5 mg/kg | | 17-18-19-20 |
| | NZ17074 3.0 mg/kg | | 21-22-23-24 |
| | NZ17074 6.0 mg/kg | | 25-26-27-28 |
| | NZ17074 12 mg/kg | | 29-30-31-32 |
| | meropenem 40 mg/kg | | 33-34-35-36 |
| | No treatment | 37-38-39-40 | |

T indicates the time in relation to treatment. Numbers in the sampling columns are mouse identification numbers.

Clinical Scoring of Mice

The mice were observed during the study and scored 0-5 based on their behaviour and clinical signs, Score 0: Healthy.
Score 1: Minor clinical signs of infection and inflammation e.g. observations of minor signs of distress or changed activity.
Score 2: Clear signs of infection like, social withdrawal, lack of curiosity, changed body position, piloerection, or changes in pattern of movement.
Score 3: Severe signs of infection like stiff movements, lack of curiosity, changed body position, piloerection, pain, or changes in pattern of movement.
Score 4: Severe pain and the mouse was sacrificed immediately to minimize the suffering of the animal.
Score 5: The mouse was dead.

Sampling

Colony counts were determined from thighs at 0 and 5 hours. The mice were anaesthetized with $CO_2+O_2$ and sacrificed. Immediately after, skin was removed and the left hind leg was collected and frozen at −70° C. After thawing, the thighs were homogenized using a DISPOMIX® Homogenizing Drive. Each sample was then 10 fold diluted in saline and 20-microliter spots were applied on the blue agar plates. All agar plates were incubated 18-22 hours at 35° C. in ambient air.

Results

The colony counts were performed at the start of treatment and 5 hours after treatment. The CFU counts are shown in Table 3. The CFU numbers are $\log_{10}$ transformed before performing calculations.

The CFU/ml in the inoculum was determined to 7.35 $\log_{10}$ corresponding to 6.05 $\log_{10}$ CFU/mouse. The high variability observed may be caused by suboptimal inoculation of some mice and resulting in too low CFU values. The lowest value in each group was therefore excluded from graphs and calculations (see table 3). At start of treatment the mean $\log_{10}$ CFU/ml was 4.93 and increased to 6.49 $\log_{10}$ CFU/ml in the vehicle group at 5 hrs after treatment. Slightly lower CFU levels were observed after treatment with NZ17074 0.16-3.0 mg/kg. Significantly lower CFU levels were observed after treatment with 6 mg/kg ($p<0.05$) and 12 mg/kg ($p<0.01$) NZ17074 compared to vehicle treatment (Table 3). Meropenem treatment, 40 mg/kg, resulted in slight but not significant reduction compared to the vehicle treated mice.

The dose-response curves (not shown) were calculated in GraphPad Prism using Sigmoidal dose-response (variable slope). From this the ED50 value was determined to 5.9 mg/kg. However, a bottom plateau was not obtained and this value may therefore be underestimated.

The maximum effect of NZ17074, $E_{max}$, was defined as the log CFU difference between no response and maximum response. No response was characterised as colony counts at the same level as determined for vehicle treated mice. The $E_{max}$ was calculated as the difference between the "Top plateau" and "Bottom plateau" in GraphPad Prism using Sigmoidal dose-response to be 2.4 Δ $\log_{10}$ CFU/ml. In addition the 1 log killing, defined as the dose required to obtain 1 log reduction in bacterial loads compared to start of treatment, was estimated using GraphPad Prism to 6.1 mg/kg. A 2 and 3 log killing was not obtained.

No clinical signs of infection were observed at any time point in any of the mice.

TABLE 7

Efficacy values for NZ17074 against *E. coli* AID#172 calculated in Graph Pad Prism

| | |
|---|---|
| TOP | 1.1 Δ$\log_{10}$ CFU/ml |
| BOTTOM | −1.3 Δ$\log_{10}$ CFU/ml |
| Emax | 2.4 Δ$\log_{10}$ CFU/ml |
| ED50 | 5.9 mg/kg |
| $R^2$ | 10.46 |
| 1 log killing | 6.1 mg/kg |

TABLE 8

Colony counts of *E. coli* AID#172 in thighs from neutropenic mice treated with a single dose of NZ17074, meropenem or vehicle.

| Treatment T = 0 hour | mouse no. | Time of sampling | $\log_{10}$ CFU thigh | mean | Treatment T = 0 hrs | mouse no. | Time of sampling | $\log_{10}$ CFU thigh | mean |
|---|---|---|---|---|---|---|---|---|---|
| Vehicle | 1 | T = 5 | 5.16¤ | 6.49 | NZ17074 | 21 | T = 5 | 5.30 | 6.07 |
| | 2 | T = 5 | 6.47 | | 3.0 mg/kg | 22 | T = 5 | 6.03 | |
| | 3 | T = 5 | 6.13 | | | 23 | T = 5 | 4.85¤ | |
| | 4 | T = 5 | 6.86 | | | 24 | T = 5 | 6.89 | |
| NZ17074 | 5 | T = 5 | 3.18¤ | 5.16 | NZ17074 | 25 | T = 5 | 2.75 | 4.10* |
| 0.16 mg/kg | 6 | T = 5 | 6.03 | | 6.0 mg/kg | 26 | T = 5 | 4.54 | |
| | 7 | T = 5 | 3.30 | | | 27 | T = 5 | 1.48¤ | |
| | 8 | T = 5 | 6.15 | | | 28 | T = 5 | 5.01 | |
| NZ17074 | 9 | T = 5 | 2.00¤ | 5.09 | NZ17074 | 29 | T = 5 | 2.48¤ | 3.32** |
| 0.30 mg/kg | 10 | T = 5 | 5.40 | | 12 mg/kg | 30 | T = 5 | 3.27 | |
| | 11 | T = 5 | 3.10 | | | 31 | T = 5 | 3.19 | |
| | 12 | T = 5 | 6.78 | | | 32 | T = 5 | 3.51 | |
| NZ17074 | 13 | T = 5 | 2.9¤ | 6.33 | Meropenem | 33 | T = 5 | 3.08¤ | 4.25 |
| 0.75 mg/kg | 14 | T = 5 | 5.72 | | 40 mg/kg | 34 | T = 5 | 3.81 | |
| | 15 | T = 5 | 7.27 | | | 35 | T = 5 | 4.99 | |
| | 16 | T = 5 | 6.00 | | | 38 | T = 5 | 3.94 | |
| NZ17074 | 17 | T = 5 | 2.56¤ | 5.62 | None | 37 | T = 0 | 4.98 | 4.93 |
| 1.5 mg/kg | 18 | T = 5 | 6.23 | | | 38 | T = 0 | 3.81¤ | |
| | 19 | T = 5 | 4.93 | | | 39 | T = 0 | 4.79 | |
| | 20 | T = 5 | 5.70 | | | 40 | T = 0 | 5.01 | |

¤This value was excluded from calculations as it was considered an outlier.
Stars indicate significantly different from vehicle group (Annova; multiple comparison).
*corresponds to $p < 0.05$;
**corresponds to $p < 0.01$.
Detection limit 1.4 $\log_{10}$ CFU/ml.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. An isolated variant of an antimicrobial peptide comprising the amino acid sequence of SEQ ID NO: 2, comprising a substitution at one or more of positions 1, 2, 3, 4, 5, 7, 8, 9, 10, 11, 12, 13, 15, 17 and 19 of the amino acid sequence of SEQ ID NO: 2, wherein
   (a) the variant has antimicrobial activity;
   (b) the number of substitutions is 1-11;
   (c) the variant comprises at least one or more non-conservative substitutions;
   (d) the variant comprises at least one non-conservative substitutions at position 5, 9 or 17 of the amino acid sequence of SEQ ID NO: 2; and
   (e) when the amino acid residues at positions 5 and 17 of the amino acid sequence of SEQ ID NO: 2 are Y and the variant comprises a non-conservative substitution at position 9, the variant comprises either (i) a conservative substitution at least at one of positions 8 or 13 or (ii) a non-conservative substitution at position 15.

2. The variant of claim 1, wherein the number of substitutions is 1-10.

3. The variant of claim 1, which comprises the amino acid sequence of any of SEQ ID NOS: 10-12, 26-28, 47-49, 56, 58, 61, 63, 64, 67-78, 86, 87, 92, 95-117, 120-125, 127, 130-137, 161-166, 168-177, 179-182, 184-195, 198-204, 206-211, 215, 220-337, 345, 346, 350, 351, 354, 355, 358-360, 363-368, 371-382, 384-389, 391, 393-451, 452, 453-493, 495-499, 501-542, and 544-548.

4. An isolated polynucleotide encoding the variant of claim 1.

5. A nucleic acid construct comprising the polynucleotide of claim 4.

6. An expression vector comprising the polynucleotide of claim 4.

7. A non-human eukaryotic or prokaryotic host cell comprising the polynucleotide of claim 4.

8. A method of producing an isolated variant of claim 1, comprising:
   a) cultivating the host cell of claim 7 under conditions suitable for expression of the variant; and
   b) recovering the variant.

9. The variant of claim 1, wherein said variant comprises at least two non-conservative substitutions at positions 5, 9, or 17.

10. The variant of claim 1, wherein said variant comprises non-conservative substitutions at positions 5, 9, or 17.

11. The variant of claim 1, which further comprises one or more substitutions selected from the group consisting of V6A, V8A, V13A, V13L, and V15S.

12. The variant of claim 1, wherein said variant comprises a non-conservative substitution at position 5 and further comprises a conservative substitution at position 6.

13. The variant of claim 1, wherein said variant comprises a non-conservative substitution at position 9 and further comprises a conservative substitution at least at position 8 or position 13.

14. The variant of claim 1, wherein said variant comprises a non-conservative substitution at position 9 and further comprises a non-conservative substitution at least at position 15.

15. The variant of claim 1, wherein said variant is selected from the group consisting of SEQ ID NO: 72, 87, 248, 308, 319, 350, 435 and 450.

16. The variant of claim 1, wherein said variant is selected from the group consisting of SEQ ID NO: 216 and 218.

17. The variant of claim 1, wherein said variant is SEQ ID NO: 72.

18. The variant of claim 1, wherein said variant is SEQ ID NO: 87.

19. The variant of claim 1, wherein said variant is SEQ ID NO: 350.

* * * * *

SEQUENCE LISTING

<160> NUMBER OF SEQ ID NOS: 548

<210> SEQ ID NO 1
<211> LENGTH: 63
<212> TYPE: DNA
<213> ORGANISM: Arenicola marina
<220> FEATURE:
<221> NAME/KEY: CDS
<222> LOCATION: (1)..(63)
<220> FEATURE:
<221> NAME/KEY: mat_peptide
<222> LOCATION: (1)..(63)

<400> SEQUENCE: 1

```
ggt ttc tgc tgg tac gtc tgc gtc tac agg aac gga gtc cgc gtc tgc        48
Gly Phe Cys Trp Tyr Val Cys Val Tyr Arg Asn Gly Val Arg Val Cys
1               5                   10                  15 tac cga cgg tgc aac                                                    63
Tyr Arg Arg Cys Asn
            20
```

<210> SEQ ID NO 2
<211> LENGTH: 21
<212> TYPE: PRT
<213> ORGANISM: Arenicola marina

<400> SEQUENCE: 2

```
Gly Phe Cys Trp Tyr Val Cys Val Tyr Arg Asn Gly Val Arg Val Cys
1               5                   10                  15

Tyr Arg Arg Cys Asn
            20
```

<210> SEQ ID NO 3
<211> LENGTH: 21
<212> TYPE: PRT
<213> ORGANISM: Artificial sequence
<220> FEATURE:
<223> OTHER INFORMATION: Synthetic construct

<400> SEQUENCE: 3

```
Gly Ala Cys Trp Tyr Val Cys Val Tyr Arg Asn Gly Val Arg Val Cys
1               5                   10                  15

Tyr Arg Arg Cys Asn
            20
```

<210> SEQ ID NO 4
<211> LENGTH: 21
<212> TYPE: PRT
<213> ORGANISM: Artificial sequence
<220> FEATURE:
<223> OTHER INFORMATION: Synthetic construct

<400> SEQUENCE: 4

```
Gly Phe Cys Ala Tyr Val Cys Val Tyr Arg Asn Gly Val Arg Val Cys
1               5                   10                  15

Tyr Arg Arg Cys Asn
            20
```

<210> SEQ ID NO 5
<211> LENGTH: 21
<212> TYPE: PRT
<213> ORGANISM: Artificial sequence
<220> FEATURE:
<223> OTHER INFORMATION: Synthetic construct

<400> SEQUENCE: 5

```
Gly Phe Cys Glu Tyr Val Cys Val Tyr Arg Asn Gly Val Arg Val Cys
1               5                   10                  15

Tyr Arg Arg Cys Asn
            20
```

<210> SEQ ID NO 6
<211> LENGTH: 21
<212> TYPE: PRT
<213> ORGANISM: Artificial sequence
<220> FEATURE:

<223> OTHER INFORMATION: Synthetic construct

<400> SEQUENCE: 6

Gly Phe Cys Gly Tyr Val Cys Val Tyr Arg Asn Gly Val Arg Val Cys
1               5                   10                  15

Tyr Arg Arg Cys Asn
            20

<210> SEQ ID NO 7
<211> LENGTH: 21
<212> TYPE: PRT
<213> ORGANISM: Artificial sequence
<220> FEATURE:
<223> OTHER INFORMATION: Synthetic construct

<400> SEQUENCE: 7

Gly Phe Cys Ser Tyr Val Cys Val Tyr Arg Asn Gly Val Arg Val Cys
1               5                   10                  15

Tyr Arg Arg Cys Asn
            20

<210> SEQ ID NO 8
<211> LENGTH: 21
<212> TYPE: PRT
<213> ORGANISM: Artificial sequence
<220> FEATURE:
<223> OTHER INFORMATION: Synthetic construct

<400> SEQUENCE: 8

Gly Phe Cys Thr Tyr Val Cys Val Tyr Arg Asn Gly Val Arg Val Cys
1               5                   10                  15

Tyr Arg Arg Cys Asn
            20

<210> SEQ ID NO 9
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 9

Gly Phe Cys Tyr Tyr Val Cys Val Tyr Arg Asn Gly Val Arg Val Cys
1               5                   10                  15

Tyr Arg Arg Cys Asn
            20

<210> SEQ ID NO 10
<211> LENGTH: 21
<212> TYPE: PRT
<213> ORGANISM: Artificial sequence
<220> FEATURE:
<223> OTHER INFORMATION: Synthetic construct

<400> SEQUENCE: 10

Gly Phe Cys Trp Lys Val Cys Val Tyr Arg Asn Gly Val Arg Val Cys
1               5                   10                  15

Tyr Arg Arg Cys Asn
            20

<210> SEQ ID NO 11
<211> LENGTH: 21
<212> TYPE: PRT
<213> ORGANISM: Artificial

```
<220> FEATURE:
<223> OTHER INFORMATION: Synthetic antimicrobial peptide

<400> SEQUENCE: 11

Gly Phe Cys Trp Asn Val Cys Val Tyr Arg Asn Gly Val Arg Val Cys
1               5                   10                  15

Tyr Arg Arg Cys Asn
            20

<210> SEQ ID NO 12
<211> LENGTH: 21
<212> TYPE: PRT
<213> ORGANISM: Artificial sequence
<220> FEATURE:
<223> OTHER INFORMATION: Synthetic construct

<400> SEQUENCE: 12

Gly Phe Cys Trp Arg Val Cys Val Tyr Arg Asn Gly Val Arg Val Cys
1               5                   10                  15

Tyr Arg Arg Cys Asn
            20

<210> SEQ ID NO 13
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 13

Gly Phe Cys Trp Tyr Ala Cys Val Tyr Arg Asn Gly Val Arg Val Cys
1               5                   10                  15

Tyr Arg Arg Cys Asn
            20

<210> SEQ ID NO 14
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 14

Gly Phe Cys Trp Tyr Glu Cys Val Tyr Arg Asn Gly Val Arg Val Cys
1               5                   10                  15

Tyr Arg Arg Cys Asn
            20

<210> SEQ ID NO 15
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 15

Gly Phe Cys Trp Tyr Gly Cys Val Tyr Arg Asn Gly Val Arg Val Cys
1               5                   10                  15

Tyr Arg Arg Cys Asn
            20

<210> SEQ ID NO 16
<211> LENGTH: 21
<212> TYPE: PRT
```

```
<213> ORGANISM: Artificial sequence
<220> FEATURE:
<223> OTHER INFORMATION: Synthetic construct

<400> SEQUENCE: 16

Gly Phe Cys Trp Tyr Leu Cys Val Tyr Arg Asn Gly Val Arg Val Cys
1               5                   10                  15

Tyr Arg Arg Cys Asn
            20

<210> SEQ ID NO 17
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 17

Gly Phe Cys Trp Tyr Asn Cys Val Tyr Arg Asn Gly Val Arg Val Cys
1               5                   10                  15

Tyr Arg Arg Cys Asn
            20

<210> SEQ ID NO 18
<211> LENGTH: 21
<212> TYPE: PRT
<213> ORGANISM: Artificial sequence
<220> FEATURE:
<223> OTHER INFORMATION: Synthetic construct

<400> SEQUENCE: 18

Gly Phe Cys Trp Tyr Arg Cys Val Tyr Arg Asn Gly Val Arg Val Cys
1               5                   10                  15

Tyr Arg Arg Cys Asn
            20

<210> SEQ ID NO 19
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 19

Gly Phe Cys Trp Tyr Ser Cys Val Tyr Arg Asn Gly Val Arg Val Cys
1               5                   10                  15

Tyr Arg Arg Cys Asn
            20

<210> SEQ ID NO 20
<211> LENGTH: 21
<212> TYPE: PRT
<213> ORGANISM: Artificial sequence
<220> FEATURE:
<223> OTHER INFORMATION: Synthetic construct

<400> SEQUENCE: 20

Gly Phe Cys Trp Tyr Trp Cys Val Tyr Arg Asn Gly Val Arg Val Cys
1               5                   10                  15

Tyr Arg Arg Cys Asn
            20

<210> SEQ ID NO 21
<211> LENGTH: 21
```

```
<212> TYPE: PRT
<213> ORGANISM: Artificial
<220> FEATURE:
<223> OTHER INFORMATION: Synthetic antimicrobial peptide

<400> SEQUENCE: 21

Gly Phe Cys Trp Tyr Val Cys Ala Tyr Arg Asn Gly Val Arg Val Cys
1               5                   10                  15

Tyr Arg Arg Cys Asn
            20

<210> SEQ ID NO 22
<211> LENGTH: 21
<212> TYPE: PRT
<213> ORGANISM: Artificial sequence
<220> FEATURE:
<223> OTHER INFORMATION: Synthetic construct

<400> SEQUENCE: 22

Gly Phe Cys Trp Tyr Val Cys Gly Tyr Arg Asn Gly Val Arg Val Cys
1               5                   10                  15

Tyr Arg Arg Cys Asn
            20

<210> SEQ ID NO 23
<211> LENGTH: 21
<212> TYPE: PRT
<213> ORGANISM: Artificial sequence
<220> FEATURE:
<223> OTHER INFORMATION: Synthetic construct

<400> SEQUENCE: 23

Gly Phe Cys Trp Tyr Val Cys His Tyr Arg Asn Gly Val Arg Val Cys
1               5                   10                  15

Tyr Arg Arg Cys Asn
            20

<210> SEQ ID NO 24
<211> LENGTH: 21
<212> TYPE: PRT
<213> ORGANISM: Artificial sequence
<220> FEATURE:
<223> OTHER INFORMATION: Synthetic construct

<400> SEQUENCE: 24

Gly Phe Cys Trp Tyr Val Cys Ser Tyr Arg Asn Gly Val Arg Val Cys
1               5                   10                  15

Tyr Arg Arg Cys Asn
            20

<210> SEQ ID NO 25
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 25

Gly Phe Cys Trp Tyr Val Cys Tyr Tyr Arg Asn Gly Val Arg Val Cys
1               5                   10                  15

Tyr Arg Arg Cys Asn
            20

<210> SEQ ID NO 26
```

```
<211> LENGTH: 21
<212> TYPE: PRT
<213> ORGANISM: Artificial sequence
<220> FEATURE:
<223> OTHER INFORMATION: Synthetic construct

<400> SEQUENCE: 26

Gly Phe Cys Trp Tyr Val Cys Val Ile Arg Asn Gly Val Arg Val Cys
1               5                   10                  15

Tyr Arg Arg Cys Asn
            20

<210> SEQ ID NO 27
<211> LENGTH: 21
<212> TYPE: PRT
<213> ORGANISM: Artificial sequence
<220> FEATURE:
<223> OTHER INFORMATION: Synthetic construct

<400> SEQUENCE: 27

Gly Phe Cys Trp Tyr Val Cys Val Lys Arg Asn Gly Val Arg Val Cys
1               5                   10                  15

Tyr Arg Arg Cys Asn
            20

<210> SEQ ID NO 28
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 28

Gly Phe Cys Trp Tyr Val Cys Val Arg Arg Asn Gly Val Arg Val Cys
1               5                   10                  15

Tyr Arg Arg Cys Asn
            20

<210> SEQ ID NO 29
<211> LENGTH: 21
<212> TYPE: PRT
<213> ORGANISM: Artificial sequence
<220> FEATURE:
<223> OTHER INFORMATION: Synthetic construct

<400> SEQUENCE: 29

Gly Phe Cys Trp Tyr Val Cys Val Tyr Arg Asn Gly Ala Arg Val Cys
1               5                   10                  15

Tyr Arg Arg Cys Asn
            20

<210> SEQ ID NO 30
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 30

Gly Phe Cys Trp Tyr Val Cys Val Tyr Arg Asn Gly Gly Arg Val Cys
1               5                   10                  15

Tyr Arg Arg Cys Asn
            20
```

```
<210> SEQ ID NO 31
<211> LENGTH: 21
<212> TYPE: PRT
<213> ORGANISM: Artificial sequence
<220> FEATURE:
<223> OTHER INFORMATION: Synthetic construct

<400> SEQUENCE: 31

Gly Phe Cys Trp Tyr Val Cys Val Tyr Arg Asn Gly Lys Arg Val Cys
1               5                   10                  15

Tyr Arg Arg Cys Asn
            20

<210> SEQ ID NO 32
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 32

Gly Phe Cys Trp Tyr Val Cys Val Tyr Arg Asn Gly Leu Arg Val Cys
1               5                   10                  15

Tyr Arg Arg Cys Asn
            20

<210> SEQ ID NO 33
<211> LENGTH: 21
<212> TYPE: PRT
<213> ORGANISM: Artificial sequence
<220> FEATURE:
<223> OTHER INFORMATION: Synthetic construct

<400> SEQUENCE: 33

Gly Phe Cys Trp Tyr Val Cys Val Tyr Arg Asn Gly Pro Arg Val Cys
1               5                   10                  15

Tyr Arg Arg Cys Asn
            20

<210> SEQ ID NO 34
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 34

Gly Phe Cys Trp Tyr Val Cys Val Tyr Arg Asn Gly Gln Arg Val Cys
1               5                   10                  15

Tyr Arg Arg Cys Asn
            20

<210> SEQ ID NO 35
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 35

Gly Phe Cys Trp Tyr Val Cys Val Tyr Arg Asn Gly Arg Arg Val Cys
1               5                   10                  15

Tyr Arg Arg Cys Asn
            20
```

<210> SEQ ID NO 36
<211> LENGTH: 21
<212> TYPE: PRT
<213> ORGANISM: Artificial sequence
<220> FEATURE:
<223> OTHER INFORMATION: Synthetic construct

<400> SEQUENCE: 36

Gly Phe Cys Trp Tyr Val Cys Val Tyr Arg Asn Gly Ser Arg Val Cys
1               5                   10                  15

Tyr Arg Arg Cys Asn
            20

<210> SEQ ID NO 37
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 37

Gly Phe Cys Trp Tyr Val Cys Val Tyr Arg Asn Gly Val Arg Ala Cys
1               5                   10                  15

Tyr Arg Arg Cys Asn
            20

<210> SEQ ID NO 38
<211> LENGTH: 21
<212> TYPE: PRT
<213> ORGANISM: Artificial sequence
<220> FEATURE:
<223> OTHER INFORMATION: Synthetic construct

<400> SEQUENCE: 38

Gly Phe Cys Trp Tyr Val Cys Val Tyr Arg Asn Gly Val Arg Gly Cys
1               5                   10                  15

Tyr Arg Arg Cys Asn
            20

<210> SEQ ID NO 39
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 39

Gly Phe Cys Trp Tyr Val Cys Val Tyr Arg Asn Gly Val Arg His Cys
1               5                   10                  15

Tyr Arg Arg Cys Asn
            20

<210> SEQ ID NO 40
<211> LENGTH: 21
<212> TYPE: PRT
<213> ORGANISM: Artificial sequence
<220> FEATURE:
<223> OTHER INFORMATION: Synthetic construct

<400> SEQUENCE: 40

Gly Phe Cys Trp Tyr Val Cys Val Tyr Arg Asn Gly Val Arg Lys Cys
1               5                   10                  15

Tyr Arg Arg Cys Asn
            20

```
<210> SEQ ID NO 41
<211> LENGTH: 21
<212> TYPE: PRT
<213> ORGANISM: Artificial sequence
<220> FEATURE:
<223> OTHER INFORMATION: Synthetic construct

<400> SEQUENCE: 41

Gly Phe Cys Trp Tyr Val Cys Val Tyr Arg Asn Gly Val Arg Asn Cys
1               5                   10                  15

Tyr Arg Arg Cys Asn
            20

<210> SEQ ID NO 42
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 42

Gly Phe Cys Trp Tyr Val Cys Val Tyr Arg Asn Gly Val Arg Gln Cys
1               5                   10                  15

Tyr Arg Arg Cys Asn
            20

<210> SEQ ID NO 43
<211> LENGTH: 21
<212> TYPE: PRT
<213> ORGANISM: Artificial sequence
<220> FEATURE:
<223> OTHER INFORMATION: Synthetic construct

<400> SEQUENCE: 43

Gly Phe Cys Trp Tyr Val Cys Val Tyr Arg Asn Gly Val Arg Arg Cys
1               5                   10                  15

Tyr Arg Arg Cys Asn
            20

<210> SEQ ID NO 44
<211> LENGTH: 21
<212> TYPE: PRT
<213> ORGANISM: Artificial sequence
<220> FEATURE:
<223> OTHER INFORMATION: Synthetic construct

<400> SEQUENCE: 44

Gly Phe Cys Trp Tyr Val Cys Val Tyr Arg Asn Gly Val Arg Ser Cys
1               5                   10                  15

Tyr Arg Arg Cys Asn
            20

<210> SEQ ID NO 45
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 45

Gly Phe Cys Trp Tyr Val Cys Val Tyr Arg Asn Gly Val Arg Thr Cys
1               5                   10                  15

Tyr Arg Arg Cys Asn
```

```
                        20

<210> SEQ ID NO 46
<211> LENGTH: 21
<212> TYPE: PRT
<213> ORGANISM: Artificial sequence
<220> FEATURE:
<223> OTHER INFORMATION: Synthetic construct

<400> SEQUENCE: 46

Gly Phe Cys Trp Tyr Val Cys Val Tyr Arg Asn Gly Val Arg Val Cys
1               5                   10                  15

His Arg Arg Cys Asn
            20

<210> SEQ ID NO 47
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 47

Gly Phe Cys Trp Tyr Val Cys Val Tyr Arg Asn Gly Val Arg Val Cys
1               5                   10                  15

Lys Arg Arg Cys Asn
            20

<210> SEQ ID NO 48
<211> LENGTH: 21
<212> TYPE: PRT
<213> ORGANISM: Artificial sequence
<220> FEATURE:
<223> OTHER INFORMATION: Synthetic construct

<400> SEQUENCE: 48

Gly Phe Cys Trp Tyr Val Cys Val Tyr Arg Asn Gly Val Arg Val Cys
1               5                   10                  15

Asn Arg Arg Cys Asn
            20

<210> SEQ ID NO 49
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 49

Gly Phe Cys Trp Tyr Val Cys Val Tyr Arg Asn Gly Val Arg Val Cys
1               5                   10                  15

Arg Arg Arg Cys Asn
            20

<210> SEQ ID NO 50
<211> LENGTH: 21
<212> TYPE: PRT
<213> ORGANISM: Artificial sequence
<220> FEATURE:
<223> OTHER INFORMATION: Synthetic construct

<400> SEQUENCE: 50

Gly Phe Cys Trp Tyr Val Cys Val Tyr Arg Asn Gly Val Arg Val Cys
1               5                   10                  15
```

Tyr Arg Arg Cys His
            20

<210> SEQ ID NO 51
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 51

Gly Phe Cys Trp Tyr Val Cys Val Tyr Arg Asn Gly Val Arg Val Cys
1               5                   10                  15

Tyr Arg Arg Cys Lys
            20

<210> SEQ ID NO 52
<211> LENGTH: 21
<212> TYPE: PRT
<213> ORGANISM: Artificial sequence
<220> FEATURE:
<223> OTHER INFORMATION: Synthetic construct

<400> SEQUENCE: 52

Gly Phe Cys Trp Tyr Val Cys Val Tyr Arg Asn Gly Val Arg Val Cys
1               5                   10                  15

Tyr Arg Arg Cys Arg
            20

<210> SEQ ID NO 53
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 53

Gly Phe Cys Trp Tyr Val Cys Val Tyr Arg Asn Gly Val Arg Val Cys
1               5                   10                  15

Tyr Arg Arg Cys Ser
            20

<210> SEQ ID NO 54
<211> LENGTH: 21
<212> TYPE: PRT
<213> ORGANISM: Artificial sequence
<220> FEATURE:
<223> OTHER INFORMATION: Synthetic construct

<400> SEQUENCE: 54

Gly Phe Cys Trp Tyr Val Cys Val Tyr Arg Asn Gly Val Arg Val Cys
1               5                   10                  15

Tyr Arg Arg Cys Thr
            20

<210> SEQ ID NO 55
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 55

Arg Phe Cys Trp Tyr Val Cys Val Tyr Arg Asn Gly Val Arg Val Cys
1               5                   10                  15

Tyr Arg Arg Cys Arg
        20

<210> SEQ ID NO 56
<211> LENGTH: 21
<212> TYPE: PRT
<213> ORGANISM: Artificial sequence
<220> FEATURE:
<223> OTHER INFORMATION: Synthetic construct

<400> SEQUENCE: 56

Gly Phe Cys Phe Tyr Val Cys Val Tyr Arg Asn Gly Val Arg Val Cys
1               5                   10                  15

Arg Arg Arg Cys Asn
        20

<210> SEQ ID NO 57
<211> LENGTH: 21
<212> TYPE: PRT
<213> ORGANISM: Artificial sequence
<220> FEATURE:
<223> OTHER INFORMATION: Synthetic construct

<400> SEQUENCE: 57

Gly Phe Cys Ala His Val Cys Val Tyr Arg Asn Gly Val Arg Val Cys
1               5                   10                  15

Tyr Arg Arg Cys Asn
        20

<210> SEQ ID NO 58
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 58

Gly Phe Cys Ala Arg Val Cys Val Tyr Arg Asn Gly Val Arg Val Cys
1               5                   10                  15

Tyr Arg Arg Cys Asn
        20

<210> SEQ ID NO 59
<211> LENGTH: 21
<212> TYPE: PRT
<213> ORGANISM: Artificial sequence
<220> FEATURE:
<223> OTHER INFORMATION: Synthetic construct

<400> SEQUENCE: 59

Gly Phe Cys Phe Tyr Val Cys Val Arg Arg Asn Gly Val Arg Val Cys
1               5                   10                  15

Tyr Arg Arg Cys Asn
        20

<210> SEQ ID NO 60
<211> LENGTH: 21
<212> TYPE: PRT
<213> ORGANISM: Artificial sequence
<220> FEATURE:
<223> OTHER INFORMATION: Synthetic construct

<400> SEQUENCE: 60

Gly Phe Cys Gly His Val Cys Val Tyr Arg Asn Gly Val Arg Val Cys

```
1               5                   10                  15
Tyr Arg Arg Cys Asn
            20

<210> SEQ ID NO 61
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 61

Gly Phe Cys Gly Arg Val Cys Val Tyr Arg Asn Gly Val Arg Val Cys
1               5                   10                  15

Tyr Arg Arg Cys Asn
            20

<210> SEQ ID NO 62
<211> LENGTH: 21
<212> TYPE: PRT
<213> ORGANISM: Artificial sequence
<220> FEATURE:
<223> OTHER INFORMATION: Synthetic construct

<400> SEQUENCE: 62

Gly Phe Cys Ser Tyr Val Cys Val Tyr Arg Asn Gly Val Arg Ala Cys
1               5                   10                  15

Tyr Arg Arg Cys Asn
            20

<210> SEQ ID NO 63
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 63

Gly Phe Cys Ser Arg Val Cys Val Tyr Arg Asn Gly Val Arg Val Cys
1               5                   10                  15

Tyr Arg Arg Cys Asn
            20

<210> SEQ ID NO 64
<211> LENGTH: 21
<212> TYPE: PRT
<213> ORGANISM: Artificial sequence
<220> FEATURE:
<223> OTHER INFORMATION: Synthetic construct

<400> SEQUENCE: 64

Gly Phe Cys Tyr Arg Val Cys Val Tyr Arg Asn Gly Val Arg Val Cys
1               5                   10                  15

Tyr Arg Arg Cys Asn
            20

<210> SEQ ID NO 65
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 65
```

```
Gly Phe Cys Trp Phe Val Cys Val Tyr Arg Asn Gly Val Arg Gln Cys
1               5                   10                  15

Tyr Arg Arg Cys Asn
            20
```

<210> SEQ ID NO 66
<211> LENGTH: 21
<212> TYPE: PRT
<213> ORGANISM: Artificial sequence
<220> FEATURE:
<223> OTHER INFORMATION: Synthetic construct

<400> SEQUENCE: 66

```
Gly Phe Cys Trp His Val Cys Val Tyr Arg Asn Gly Val Arg Ser Cys
1               5                   10                  15

Tyr Arg Arg Cys Asn
            20
```

<210> SEQ ID NO 67
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 67

```
Gly Phe Cys Trp His Val Cys Val Tyr Arg Asn Gly Val Arg Val Cys
1               5                   10                  15

Arg Arg Arg Cys Asn
            20
```

<210> SEQ ID NO 68
<211> LENGTH: 21
<212> TYPE: PRT
<213> ORGANISM: Artificial sequence
<220> FEATURE:
<223> OTHER INFORMATION: Synthetic construct

<400> SEQUENCE: 68

```
Gly Phe Cys Trp Lys Val Cys Val Tyr Arg Asn Gly Val Arg Val Cys
1               5                   10                  15

Ser Arg Arg Cys Asn
            20
```

<210> SEQ ID NO 69
<211> LENGTH: 21
<212> TYPE: PRT
<213> ORGANISM: Artificial sequence
<220> FEATURE:
<223> OTHER INFORMATION: Synthetic construct

<400> SEQUENCE: 69

```
Gly Phe Cys Trp Asn Val Cys Val Tyr Arg Asn Gly Val Arg Ser Cys
1               5                   10                  15

Tyr Arg Arg Cys Asn
            20
```

<210> SEQ ID NO 70
<211> LENGTH: 21
<212> TYPE: PRT
<213> ORGANISM: Artificial sequence
<220> FEATURE:
<223> OTHER INFORMATION: Synthetic construct

<400> SEQUENCE: 70

```
Gly Phe Cys Trp Asn Val Cys Val Tyr Arg Asn Gly Val Arg Val Cys
1               5                   10                  15

His Arg Arg Cys Asn
            20

<210> SEQ ID NO 71
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 71

Gly Phe Cys Trp Arg Val Cys Val Tyr Arg Asn Gly Val Arg Pro Cys
1               5                   10                  15

Tyr Arg Arg Cys Asn
            20

<210> SEQ ID NO 72
<211> LENGTH: 21
<212> TYPE: PRT
<213> ORGANISM: Artificial sequence
<220> FEATURE:
<223> OTHER INFORMATION: Synthetic construct

<400> SEQUENCE: 72

Gly Phe Cys Trp Arg Ala Cys Val Tyr Arg Asn Gly Val Arg Val Cys
1               5                   10                  15

Tyr Arg Arg Cys Asn
            20

<210> SEQ ID NO 73
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 73

Gly Phe Cys Trp Arg Val Cys Gly Tyr Arg Asn Gly Val Arg Val Cys
1               5                   10                  15

Tyr Arg Arg Cys Asn
            20

<210> SEQ ID NO 74
<211> LENGTH: 21
<212> TYPE: PRT
<213> ORGANISM: Artificial sequence
<220> FEATURE:
<223> OTHER INFORMATION: Synthetic construct

<400> SEQUENCE: 74

Gly Phe Cys Trp Arg Val Cys His Tyr Arg Asn Gly Val Arg Val Cys
1               5                   10                  15

Tyr Arg Arg Cys Asn
            20

<210> SEQ ID NO 75
<211> LENGTH: 21
<212> TYPE: PRT
<213> ORGANISM: Artificial
<220> FEATURE:
<223> OTHER INFORMATION: Synthetic antimicrobial peptide
```

```
<400> SEQUENCE: 75

Gly Phe Cys Trp Arg Val Cys Ser Tyr Arg Asn Gly Val Arg Val Cys
1               5                   10                  15

Tyr Arg Arg Cys Asn
            20

<210> SEQ ID NO 76
<211> LENGTH: 21
<212> TYPE: PRT
<213> ORGANISM: Artificial sequence
<220> FEATURE:
<223> OTHER INFORMATION: Synthetic construct

<400> SEQUENCE: 76

Gly Phe Cys Trp Arg Val Cys Val Tyr Arg Asn Gly Val Arg Val Cys
1               5                   10                  15

His Arg Arg Cys Asn
            20

<210> SEQ ID NO 77
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 77

Gly Phe Cys Trp Arg Val Cys Val Tyr Arg Asn Gly Val Arg Val Cys
1               5                   10                  15

Asn Arg Arg Cys Asn
            20

<210> SEQ ID NO 78
<211> LENGTH: 21
<212> TYPE: PRT
<213> ORGANISM: Artificial sequence
<220> FEATURE:
<223> OTHER INFORMATION: Synthetic construct

<400> SEQUENCE: 78

Gly Phe Cys Trp Ser Val Cys Val Tyr Arg Asn Gly Val Arg Ser Cys
1               5                   10                  15

Tyr Arg Arg Cys Asn
            20

<210> SEQ ID NO 79
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 79

Gly Phe Cys Trp Tyr Ala Cys Val Tyr Arg Asn Gly Ala Arg Val Cys
1               5                   10                  15

Tyr Arg Arg Cys Asn
            20

<210> SEQ ID NO 80
<211> LENGTH: 21
<212> TYPE: PRT
<213> ORGANISM: Artificial sequence
<220> FEATURE:
<223> OTHER INFORMATION: Synthetic construct
```

-continued

```
<400> SEQUENCE: 80

Gly Phe Cys Trp Tyr Ala Cys Val Tyr Arg Asn Gly Lys Arg Val Cys
1               5                   10                  15

Tyr Arg Arg Cys Asn
            20

<210> SEQ ID NO 81
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 81

Gly Phe Cys Trp Tyr Ala Cys Val Tyr Arg Asn Gly Val Arg Ala Cys
1               5                   10                  15

Tyr Arg Arg Cys Asn
            20

<210> SEQ ID NO 82
<211> LENGTH: 21
<212> TYPE: PRT
<213> ORGANISM: Artificial sequence
<220> FEATURE:
<223> OTHER INFORMATION: Synthetic construct

<400> SEQUENCE: 82

Gly Phe Cys Trp Tyr Ala Cys Val Tyr Arg Asn Gly Val Arg Val Cys
1               5                   10                  15

His Arg Arg Cys Asn
            20

<210> SEQ ID NO 83
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 83

Gly Phe Cys Trp Tyr Met Cys Gly Tyr Arg Asn Gly Val Arg Val Cys
1               5                   10                  15

Tyr Arg Arg Cys Asn
            20

<210> SEQ ID NO 84
<211> LENGTH: 21
<212> TYPE: PRT
<213> ORGANISM: Artificial sequence
<220> FEATURE:
<223> OTHER INFORMATION: Synthetic construct

<400> SEQUENCE: 84

Gly Phe Cys Trp Tyr Val Cys Ala Tyr Arg Asn Gly Val Arg Ala Cys
1               5                   10                  15

Tyr Arg Arg Cys Asn
            20

<210> SEQ ID NO 85
<211> LENGTH: 21
<212> TYPE: PRT
<213> ORGANISM: Artificial
<220> FEATURE:
```

<223> OTHER INFORMATION: Synthetic antimicrobial peptide

<400> SEQUENCE: 85

Gly Phe Cys Trp Tyr Val Cys Ser Tyr Arg Asn Gly Lys Arg Val Cys
1               5                   10                  15

Tyr Arg Arg Cys Asn
            20

<210> SEQ ID NO 86
<211> LENGTH: 21
<212> TYPE: PRT
<213> ORGANISM: Artificial sequence
<220> FEATURE:
<223> OTHER INFORMATION: Synthetic construct

<400> SEQUENCE: 86

Gly Phe Cys Trp Tyr Val Cys Val Lys Arg Asn Gly Ala Arg Val Cys
1               5                   10                  15

Tyr Arg Arg Cys Asn
            20

<210> SEQ ID NO 87
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 87

Gly Phe Cys Trp Tyr Val Cys Val Lys Arg Asn Gly Val Arg Ser Cys
1               5                   10                  15

Tyr Arg Arg Cys Asn
            20

<210> SEQ ID NO 88
<211> LENGTH: 21
<212> TYPE: PRT
<213> ORGANISM: Artificial sequence
<220> FEATURE:
<223> OTHER INFORMATION: Synthetic construct

<400> SEQUENCE: 88

Gly Phe Cys Trp Tyr Val Cys Val Tyr Lys Asn Gly Val Arg Ser Cys
1               5                   10                  15

Tyr Arg Arg Cys Asn
            20

<210> SEQ ID NO 89
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 89

Gly Phe Cys Trp Tyr Val Cys Val Tyr Lys Asn Gly Val Arg Val Cys
1               5                   10                  15

His Arg Arg Cys Asn
            20

<210> SEQ ID NO 90
<211> LENGTH: 21
<212> TYPE: PRT
<213> ORGANISM: Artificial sequence

```
<220> FEATURE:
<223> OTHER INFORMATION: Synthetic construct

<400> SEQUENCE: 90

Gly Phe Cys Trp Tyr Val Cys Val Tyr Pro Asn Gly Gly Arg Val Cys
1               5                   10                  15

Tyr Arg Arg Cys Asn
            20

<210> SEQ ID NO 91
<211> LENGTH: 21
<212> TYPE: PRT
<213> ORGANISM: Artificial sequence
<220> FEATURE:
<223> OTHER INFORMATION: Synthetic construct

<400> SEQUENCE: 91

Gly Phe Cys Trp Tyr Val Cys Val Tyr Arg Arg Gly Val Arg Gln Cys
1               5                   10                  15

Tyr Arg Arg Cys Asn
            20

<210> SEQ ID NO 92
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 92

Gly Phe Cys Trp Tyr Val Cys Val Tyr Arg Asn Gly Ala Arg Val Cys
1               5                   10                  15

Cys Arg Arg Cys Asn
            20

<210> SEQ ID NO 93
<211> LENGTH: 21
<212> TYPE: PRT
<213> ORGANISM: Artificial sequence
<220> FEATURE:
<223> OTHER INFORMATION: Synthetic construct

<400> SEQUENCE: 93

Gly Phe Cys Trp Tyr Val Cys Val Tyr Arg Asn Gly Gly Arg Lys Cys
1               5                   10                  15

Tyr Arg Arg Cys Asn
            20

<210> SEQ ID NO 94
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 94

Gly Phe Cys Trp Tyr Val Cys Val Tyr Arg Asn Gly Val Arg Leu Cys
1               5                   10                  15

His Arg Arg Cys Asn
            20

<210> SEQ ID NO 95
<211> LENGTH: 21
<212> TYPE: PRT
```

<213> ORGANISM: Artificial sequence
<220> FEATURE:
<223> OTHER INFORMATION: Synthetic construct

<400> SEQUENCE: 95

Ala Phe Cys Trp Asn Val Cys Val Tyr Arg Asn Gly Val Arg Val Cys
1               5                   10                  15

His Arg Arg Cys Asn
            20

<210> SEQ ID NO 96
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 96

Asp Phe Cys Trp Asn Val Cys Val Tyr Arg Asn Gly Val Arg Val Cys
1               5                   10                  15

His Arg Arg Cys Asn
            20

<210> SEQ ID NO 97
<211> LENGTH: 21
<212> TYPE: PRT
<213> ORGANISM: Artificial sequence
<220> FEATURE:
<223> OTHER INFORMATION: Synthetic construct

<400> SEQUENCE: 97

Phe Phe Cys Trp Asn Val Cys Val Tyr Arg Asn Gly Val Arg Val Cys
1               5                   10                  15

His Arg Arg Cys Asn
            20

<210> SEQ ID NO 98
<211> LENGTH: 21
<212> TYPE: PRT
<213> ORGANISM: Artificial sequence
<220> FEATURE:
<223> OTHER INFORMATION: Synthetic construct

<400> SEQUENCE: 98

His Phe Cys Trp Asn Val Cys Val Tyr Arg Asn Gly Val Arg Val Cys
1               5                   10                  15

His Arg Arg Cys Asn
            20

<210> SEQ ID NO 99
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 99

Ile Phe Cys Trp Asn Val Cys Val Tyr Arg Asn Gly Val Arg Val Cys
1               5                   10                  15

His Arg Arg Cys Asn
            20

<210> SEQ ID NO 100
<211> LENGTH: 21

```
<212> TYPE: PRT
<213> ORGANISM: Artificial sequence
<220> FEATURE:
<223> OTHER INFORMATION: Synthetic construct

<400> SEQUENCE: 100

Lys Phe Cys Trp Asn Val Cys Val Tyr Arg Asn Gly Val Arg Val Cys
1               5                   10                  15

His Arg Arg Cys Asn
            20

<210> SEQ ID NO 101
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 101

Met Phe Cys Trp Asn Val Cys Val Tyr Arg Asn Gly Val Arg Val Cys
1               5                   10                  15

His Arg Arg Cys Asn
            20

<210> SEQ ID NO 102
<211> LENGTH: 21
<212> TYPE: PRT
<213> ORGANISM: Artificial sequence
<220> FEATURE:
<223> OTHER INFORMATION: Synthetic construct

<400> SEQUENCE: 102

Gln Phe Cys Trp Asn Val Cys Val Tyr Arg Asn Gly Val Arg Val Cys
1               5                   10                  15

His Arg Arg Cys Asn
            20

<210> SEQ ID NO 103
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 103

Arg Phe Cys Trp Asn Val Cys Val Tyr Arg Asn Gly Val Arg Val Cys
1               5                   10                  15

His Arg Arg Cys Asn
            20

<210> SEQ ID NO 104
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 104

Ser Phe Cys Trp Asn Val Cys Val Tyr Arg Asn Gly Val Arg Val Cys
1               5                   10                  15

His Arg Arg Cys Asn
            20

<210> SEQ ID NO 105
```

```
<211> LENGTH: 21
<212> TYPE: PRT
<213> ORGANISM: Artificial sequence
<220> FEATURE:
<223> OTHER INFORMATION: Synthetic construct

<400> SEQUENCE: 105

Thr Phe Cys Trp Asn Val Cys Val Tyr Arg Asn Gly Val Arg Val Cys
1               5                   10                  15

His Arg Arg Cys Asn
            20

<210> SEQ ID NO 106
<211> LENGTH: 21
<212> TYPE: PRT
<213> ORGANISM: Artificial sequence
<220> FEATURE:
<223> OTHER INFORMATION: Synthetic construct

<400> SEQUENCE: 106

Val Phe Cys Trp Asn Val Cys Val Tyr Arg Asn Gly Val Arg Val Cys
1               5                   10                  15

His Arg Arg Cys Asn
            20

<210> SEQ ID NO 107
<211> LENGTH: 21
<212> TYPE: PRT
<213> ORGANISM: Artificial sequence
<220> FEATURE:
<223> OTHER INFORMATION: Synthetic construct

<400> SEQUENCE: 107

Trp Phe Cys Trp Asn Val Cys Val Tyr Arg Asn Gly Val Arg Val Cys
1               5                   10                  15

His Arg Arg Cys Asn
            20

<210> SEQ ID NO 108
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 108

Tyr Phe Cys Trp Asn Val Cys Val Tyr Arg Asn Gly Val Arg Val Cys
1               5                   10                  15

His Arg Arg Cys Asn
            20

<210> SEQ ID NO 109
<211> LENGTH: 21
<212> TYPE: PRT
<213> ORGANISM: Artificial sequence
<220> FEATURE:
<223> OTHER INFORMATION: Synthetic construct

<400> SEQUENCE: 109

Gly Gly Cys Trp Asn Val Cys Val Tyr Arg Asn Gly Val Arg Val Cys
1               5                   10                  15

His Arg Arg Cys Asn
            20
```

```
<210> SEQ ID NO 110
<211> LENGTH: 21
<212> TYPE: PRT
<213> ORGANISM: Artificial sequence
<220> FEATURE:
<223> OTHER INFORMATION: Synthetic construct

<400> SEQUENCE: 110

Gly His Cys Trp Asn Val Cys Val Tyr Arg Asn Gly Val Arg Val Cys
1               5                   10                  15

His Arg Arg Cys Asn
            20

<210> SEQ ID NO 111
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 111

Gly Ile Cys Trp Asn Val Cys Val Tyr Arg Asn Gly Val Arg Val Cys
1               5                   10                  15

His Arg Arg Cys Asn
            20

<210> SEQ ID NO 112
<211> LENGTH: 21
<212> TYPE: PRT
<213> ORGANISM: Artificial sequence
<220> FEATURE:
<223> OTHER INFORMATION: Synthetic construct

<400> SEQUENCE: 112

Gly Leu Cys Trp Asn Val Cys Val Tyr Arg Asn Gly Val Arg Val Cys
1               5                   10                  15

His Arg Arg Cys Asn
            20

<210> SEQ ID NO 113
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 113

Gly Met Cys Trp Asn Val Cys Val Tyr Arg Asn Gly Val Arg Val Cys
1               5                   10                  15

His Arg Arg Cys Asn
            20

<210> SEQ ID NO 114
<211> LENGTH: 21
<212> TYPE: PRT
<213> ORGANISM: Artificial sequence
<220> FEATURE:
<223> OTHER INFORMATION: Synthetic construct

<400> SEQUENCE: 114

Gly Pro Cys Trp Asn Val Cys Val Tyr Arg Asn Gly Val Arg Val Cys
1               5                   10                  15

His Arg Arg Cys Asn
            20
```

<210> SEQ ID NO 115
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 115

Gly Val Cys Trp Asn Val Cys Val Tyr Arg Asn Gly Val Arg Val Cys
1               5                   10                  15

His Arg Arg Cys Asn
            20

<210> SEQ ID NO 116
<211> LENGTH: 21
<212> TYPE: PRT
<213> ORGANISM: Artificial sequence
<220> FEATURE:
<223> OTHER INFORMATION: Synthetic construct

<400> SEQUENCE: 116

Gly Trp Cys Trp Asn Val Cys Val Tyr Arg Asn Gly Val Arg Val Cys
1               5                   10                  15

His Arg Arg Cys Asn
            20

<210> SEQ ID NO 117
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 117

Gly Tyr Cys Trp Asn Val Cys Val Tyr Arg Asn Gly Val Arg Val Cys
1               5                   10                  15

His Arg Arg Cys Asn
            20

<210> SEQ ID NO 118
<211> LENGTH: 21
<212> TYPE: PRT
<213> ORGANISM: Artificial sequence
<220> FEATURE:
<223> OTHER INFORMATION: Synthetic construct

<400> SEQUENCE: 118

Gly Phe Leu Gln Tyr Val Cys Val Tyr Arg Asn Gly Val Arg Val Cys
1               5                   10                  15

His Arg Arg Cys Asn
            20

<210> SEQ ID NO 119
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 119

Gly Phe Cys Ala Tyr Ala Cys Val Lys Arg Asn Gly Val Arg Val Cys
1               5                   10                  15

Tyr Arg Arg Cys Asn
            20

```
<210> SEQ ID NO 120
<211> LENGTH: 21
<212> TYPE: PRT
<213> ORGANISM: Artificial sequence
<220> FEATURE:
<223> OTHER INFORMATION: Synthetic construct

<400> SEQUENCE: 120

Gly Phe Cys Ala Lys Val Cys Val Tyr Arg Asn Gly Val Arg Ser Cys
1               5                   10                  15

Tyr Arg Arg Cys Asn
            20

<210> SEQ ID NO 121
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 121

Gly Phe Cys Ala Arg Val Cys Val Tyr Arg Asn Gly Val Arg Ala Cys
1               5                   10                  15

Tyr Arg Arg Cys Asn
            20

<210> SEQ ID NO 122
<211> LENGTH: 21
<212> TYPE: PRT
<213> ORGANISM: Artificial sequence
<220> FEATURE:
<223> OTHER INFORMATION: Synthetic construct

<400> SEQUENCE: 122

Gly Phe Cys Ala Arg Val Cys Val Tyr Arg Asn Gly Val Arg Ser Cys
1               5                   10                  15

Tyr Arg Arg Cys Asn
            20

<210> SEQ ID NO 123
<211> LENGTH: 21
<212> TYPE: PRT
<213> ORGANISM: Artificial sequence
<220> FEATURE:
<223> OTHER INFORMATION: Synthetic construct

<400> SEQUENCE: 123

Gly Phe Cys Ala Arg Val Cys Val Tyr Arg Asn Gly Val Arg Thr Cys
1               5                   10                  15

Tyr Arg Arg Cys Asn
            20

<210> SEQ ID NO 124
<211> LENGTH: 21
<212> TYPE: PRT
<213> ORGANISM: Artificial sequence
<220> FEATURE:
<223> OTHER INFORMATION: Synthetic construct

<400> SEQUENCE: 124

Gly Phe Cys Ala Arg Val Cys Ser Tyr Arg Asn Gly Val Arg Val Cys
1               5                   10                  15

Tyr Arg Arg Cys Asn
```

```
                        20

<210> SEQ ID NO 125
<211> LENGTH: 21
<212> TYPE: PRT
<213> ORGANISM: Artificial sequence
<220> FEATURE:
<223> OTHER INFORMATION: Synthetic construct

<400> SEQUENCE: 125

Gly Phe Cys Ala Arg Val Cys Val Lys Arg Asn Gly Val Arg Val Cys
1               5                   10                  15

Tyr Arg Arg Cys Asn
            20

<210> SEQ ID NO 126
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 126

Gly Phe Cys Ala Trp Val Cys Val Tyr Arg Asn Gly Val Arg Gln Cys
1               5                   10                  15

Tyr Arg Arg Cys Asn
            20

<210> SEQ ID NO 127
<211> LENGTH: 21
<212> TYPE: PRT
<213> ORGANISM: Artificial sequence
<220> FEATURE:
<223> OTHER INFORMATION: Synthetic construct

<400> SEQUENCE: 127

Gly Phe Cys Ala Tyr Val Cys Val Arg Arg Asn Gly Val Arg Ser Cys
1               5                   10                  15

Tyr Arg Arg Cys Asn
            20

<210> SEQ ID NO 128
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 128

Gly Phe Cys Phe Tyr Val Cys Ala Tyr Arg Asn Gly Val Arg Ser Cys
1               5                   10                  15

Tyr Arg Arg Cys Asn
            20

<210> SEQ ID NO 129
<211> LENGTH: 21
<212> TYPE: PRT
<213> ORGANISM: Artificial sequence
<220> FEATURE:
<223> OTHER INFORMATION: Synthetic construct

<400> SEQUENCE: 129

Gly Phe Cys Phe His Val Cys Val Tyr Arg Asn Gly Val Arg Ser Cys
1               5                   10                  15
```

Tyr Arg Arg Cys Asn
            20

<210> SEQ ID NO 130
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 130

Gly Phe Cys Phe Asn Val Cys Val Tyr Arg Asn Gly Val Arg Ser Cys
1               5                   10                  15

Tyr Arg Arg Cys Asn
            20

<210> SEQ ID NO 131
<211> LENGTH: 21
<212> TYPE: PRT
<213> ORGANISM: Artificial sequence
<220> FEATURE:
<223> OTHER INFORMATION: Synthetic construct

<400> SEQUENCE: 131

Gly Phe Cys Phe Asn Val Cys Val Tyr Arg Asn Gly Val Arg Val Cys
1               5                   10                  15

His Arg Arg Cys Asn
            20

<210> SEQ ID NO 132
<211> LENGTH: 21
<212> TYPE: PRT
<213> ORGANISM: Artificial sequence
<220> FEATURE:
<223> OTHER INFORMATION: Synthetic construct

<400> SEQUENCE: 132

Gly Phe Cys Phe Arg Val Cys Val Tyr Arg Asn Gly Val Arg Lys Cys
1               5                   10                  15

Tyr Arg Arg Cys Asn
            20

<210> SEQ ID NO 133
<211> LENGTH: 21
<212> TYPE: PRT
<213> ORGANISM: Artificial sequence
<220> FEATURE:
<223> OTHER INFORMATION: Synthetic construct

<400> SEQUENCE: 133

Gly Phe Cys Phe Arg Val Cys Val Tyr Arg Asn Gly Val Arg Gln Cys
1               5                   10                  15

Tyr Arg Arg Cys Asn
            20

<210> SEQ ID NO 134
<211> LENGTH: 21
<212> TYPE: PRT
<213> ORGANISM: Artificial sequence
<220> FEATURE:
<223> OTHER INFORMATION: Synthetic construct

<400> SEQUENCE: 134

Gly Phe Cys Phe Arg Val Cys Val Tyr Arg Asn Gly Val Arg Ser Cys
1               5                   10                  15

Tyr Arg Arg Cys Asn
            20

<210> SEQ ID NO 135
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 135

Gly Phe Cys Phe Arg Val Cys Val Tyr Arg Asn Gly Val Arg Val Cys
1               5                   10                  15

His Arg Arg Cys Asn
            20

<210> SEQ ID NO 136
<211> LENGTH: 21
<212> TYPE: PRT
<213> ORGANISM: Artificial sequence
<220> FEATURE:
<223> OTHER INFORMATION: Synthetic construct

<400> SEQUENCE: 136

Gly Phe Cys Phe Arg Val Cys Val Tyr Arg Asn Gly Val Arg Val Cys
1               5                   10                  15

Gln Arg Arg Cys Asn
            20

<210> SEQ ID NO 137
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 137

Gly Phe Cys Phe Tyr Val Cys Val Lys Arg Asn Gly Val Arg Val Cys
1               5                   10                  15

His Arg Arg Cys Asn
            20

<210> SEQ ID NO 138
<211> LENGTH: 21
<212> TYPE: PRT
<213> ORGANISM: Artificial sequence
<220> FEATURE:
<223> OTHER INFORMATION: Synthetic construct

<400> SEQUENCE: 138

Gly Phe Cys Gly His Val Cys Val Tyr Arg Asn Gly Val Arg Val Cys
1               5                   10                  15

Tyr Arg Arg Cys Ala
            20

<210> SEQ ID NO 139
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 139

Gly Phe Cys Gly His Val Cys Val Tyr Arg Asn Gly Val Arg Val Cys

```
1               5                   10                  15

Tyr Arg Arg Cys Lys
            20

<210> SEQ ID NO 140
<211> LENGTH: 21
<212> TYPE: PRT
<213> ORGANISM: Artificial sequence
<220> FEATURE:
<223> OTHER INFORMATION: Synthetic construct

<400> SEQUENCE: 140

Gly Phe Cys Gly His Val Cys Val Tyr Arg Asn Gly Val Arg Val Cys
1               5                   10                  15

Tyr Arg Arg Cys Leu
            20

<210> SEQ ID NO 141
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 141

Gly Phe Cys Gly His Val Cys Val Tyr Arg Asn Gly Val Arg Val Cys
1               5                   10                  15

Tyr Arg Arg Cys Met
            20

<210> SEQ ID NO 142
<211> LENGTH: 21
<212> TYPE: PRT
<213> ORGANISM: Artificial sequence
<220> FEATURE:
<223> OTHER INFORMATION: Synthetic construct

<400> SEQUENCE: 142

Gly Phe Cys Gly His Val Cys Val Tyr Arg Asn Gly Val Arg Val Cys
1               5                   10                  15

Tyr Arg Arg Cys Pro
            20

<210> SEQ ID NO 143
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 143

Gly Phe Cys Gly His Val Cys Val Tyr Arg Asn Gly Val Arg Val Cys
1               5                   10                  15

Tyr Arg Arg Cys Arg
            20

<210> SEQ ID NO 144
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 144
```

```
Gly Phe Cys Gly His Val Cys Val Tyr Arg Asn Gly Val Arg Val Cys
1               5                   10                  15

Tyr Arg Arg Cys Ser
            20

<210> SEQ ID NO 145
<211> LENGTH: 21
<212> TYPE: PRT
<213> ORGANISM: Artificial sequence
<220> FEATURE:
<223> OTHER INFORMATION: Synthetic construct

<400> SEQUENCE: 145

Gly Phe Cys Gly His Val Cys Val Tyr Arg Asn Gly Val Arg Val Cys
1               5                   10                  15

Tyr Arg Arg Cys Tyr
            20

<210> SEQ ID NO 146
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 146

Gly Phe Cys Gly His Val Cys Val Tyr Arg Asn Gly Val Arg Ala Cys
1               5                   10                  15

Tyr Arg Arg Cys Asn
            20

<210> SEQ ID NO 147
<211> LENGTH: 21
<212> TYPE: PRT
<213> ORGANISM: Artificial sequence
<220> FEATURE:
<223> OTHER INFORMATION: Synthetic construct

<400> SEQUENCE: 147

Gly Phe Cys Gly His Val Cys Val Tyr Arg Asn Gly Val Arg Phe Cys
1               5                   10                  15

Tyr Arg Arg Cys Asn
            20

<210> SEQ ID NO 148
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 148

Gly Phe Cys Gly His Val Cys Val Tyr Arg Asn Gly Val Arg Gly Cys
1               5                   10                  15

Tyr Arg Arg Cys Asn
            20

<210> SEQ ID NO 149
<211> LENGTH: 21
<212> TYPE: PRT
<213> ORGANISM: Artificial sequence
<220> FEATURE:
<223> OTHER INFORMATION: Synthetic construct

<400> SEQUENCE: 149
```

-continued

Gly Phe Cys Gly His Val Cys Val Tyr Arg Asn Gly Val Arg His Cys
1               5                   10                  15

Tyr Arg Arg Cys Asn
            20

<210> SEQ ID NO 150
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 150

Gly Phe Cys Gly His Val Cys Val Tyr Arg Asn Gly Val Arg Ile Cys
1               5                   10                  15

Tyr Arg Arg Cys Asn
            20

<210> SEQ ID NO 151
<211> LENGTH: 21
<212> TYPE: PRT
<213> ORGANISM: Artificial sequence
<220> FEATURE:
<223> OTHER INFORMATION: Synthetic construct

<400> SEQUENCE: 151

Gly Phe Cys Gly His Val Cys Val Tyr Arg Asn Gly Val Arg Leu Cys
1               5                   10                  15

Tyr Arg Arg Cys Asn
            20

<210> SEQ ID NO 152
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 152

Gly Phe Cys Gly His Val Cys Val Tyr Arg Asn Gly Val Arg Met Cys
1               5                   10                  15

Tyr Arg Arg Cys Asn
            20

<210> SEQ ID NO 153
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 153

Gly Phe Cys Gly His Val Cys Val Tyr Arg Asn Gly Val Arg Asn Cys
1               5                   10                  15

Tyr Arg Arg Cys Asn
            20

<210> SEQ ID NO 154
<211> LENGTH: 21
<212> TYPE: PRT
<213> ORGANISM: Artificial sequence
<220> FEATURE:
<223> OTHER INFORMATION: Synthetic construct

```
<400> SEQUENCE: 154

Gly Phe Cys Gly His Val Cys Val Tyr Arg Asn Gly Val Arg Gln Cys
1               5                   10                  15

Tyr Arg Arg Cys Asn
            20

<210> SEQ ID NO 155
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 155

Gly Phe Cys Gly His Val Cys Val Tyr Arg Asn Gly Val Arg Arg Cys
1               5                   10                  15

Tyr Arg Arg Cys Asn
            20

<210> SEQ ID NO 156
<211> LENGTH: 21
<212> TYPE: PRT
<213> ORGANISM: Artificial sequence
<220> FEATURE:
<223> OTHER INFORMATION: Synthetic construct

<400> SEQUENCE: 156

Gly Phe Cys Gly His Val Cys Val Tyr Arg Asn Gly Val Arg Ser Cys
1               5                   10                  15

Tyr Arg Arg Cys Asn
            20

<210> SEQ ID NO 157
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 157

Gly Phe Cys Gly His Val Cys Val Tyr Arg Asn Gly Val Arg Thr Cys
1               5                   10                  15

Tyr Arg Arg Cys Asn
            20

<210> SEQ ID NO 158
<211> LENGTH: 21
<212> TYPE: PRT
<213> ORGANISM: Artificial sequence
<220> FEATURE:
<223> OTHER INFORMATION: Synthetic construct

<400> SEQUENCE: 158

Gly Phe Cys Gly His Val Cys Val Tyr Arg Asn Gly Val Arg Trp Cys
1               5                   10                  15

Tyr Arg Arg Cys Asn
            20

<210> SEQ ID NO 159
<211> LENGTH: 21
<212> TYPE: PRT
<213> ORGANISM: Artificial
<220> FEATURE:
<223> OTHER INFORMATION: Synthetic antimicrobial peptide
```

```
<400> SEQUENCE: 159

Gly Phe Cys Gly His Val Cys Val Tyr Arg Asn Gly Val Arg Tyr Cys
1               5                   10                  15

Tyr Arg Arg Cys Asn
            20

<210> SEQ ID NO 160
<211> LENGTH: 21
<212> TYPE: PRT
<213> ORGANISM: Artificial sequence
<220> FEATURE:
<223> OTHER INFORMATION: Synthetic construct

<400> SEQUENCE: 160

Gly Phe Cys Gly His Val Cys Val Tyr Arg Asn Gly Val Arg Val Cys
1               5                   10                  15

Phe Arg Arg Cys Asn
            20

<210> SEQ ID NO 161
<211> LENGTH: 21
<212> TYPE: PRT
<213> ORGANISM: Artificial sequence
<220> FEATURE:
<223> OTHER INFORMATION: Synthetic construct

<400> SEQUENCE: 161

Gly Phe Cys Gly His Val Cys Val Tyr Arg Asn Gly Val Arg Val Cys
1               5                   10                  15

Gly Arg Arg Cys Asn
            20

<210> SEQ ID NO 162
<211> LENGTH: 21
<212> TYPE: PRT
<213> ORGANISM: Artificial sequence
<220> FEATURE:
<223> OTHER INFORMATION: Synthetic construct

<400> SEQUENCE: 162

Gly Phe Cys Gly His Val Cys Val Tyr Arg Asn Gly Val Arg Val Cys
1               5                   10                  15

Ile Arg Arg Cys Asn
            20

<210> SEQ ID NO 163
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 163

Gly Phe Cys Gly His Val Cys Val Tyr Arg Asn Gly Val Arg Val Cys
1               5                   10                  15

Leu Arg Arg Cys Asn
            20

<210> SEQ ID NO 164
<211> LENGTH: 21
<212> TYPE: PRT
<213> ORGANISM: Artificial
<220> FEATURE:
```

<223> OTHER INFORMATION: Synthetic antimicrobial peptide

<400> SEQUENCE: 164

Gly Phe Cys Gly His Val Cys Val Tyr Arg Asn Gly Val Arg Val Cys
1               5                   10                  15

Met Arg Arg Cys Asn
            20

<210> SEQ ID NO 165
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 165

Gly Phe Cys Gly His Val Cys Val Tyr Arg Asn Gly Val Arg Val Cys
1               5                   10                  15

Thr Arg Arg Cys Asn
            20

<210> SEQ ID NO 166
<211> LENGTH: 21
<212> TYPE: PRT
<213> ORGANISM: Artificial sequence
<220> FEATURE:
<223> OTHER INFORMATION: Synthetic construct

<400> SEQUENCE: 166

Gly Phe Cys Gly His Val Cys Val Tyr Arg Asn Gly Val Arg Val Cys
1               5                   10                  15

Val Arg Arg Cys Asn
            20

<210> SEQ ID NO 167
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 167

Gly Phe Cys Gly His Val Cys Val Tyr Arg Asn Gly Val Arg Val Cys
1               5                   10                  15

Trp Arg Arg Cys Asn
            20

<210> SEQ ID NO 168
<211> LENGTH: 21
<212> TYPE: PRT
<213> ORGANISM: Artificial sequence
<220> FEATURE:
<223> OTHER INFORMATION: Synthetic construct

<400> SEQUENCE: 168

Gly Phe Cys Gly Lys Val Cys Val Tyr Arg Asn Gly Val Arg His Cys
1               5                   10                  15

Tyr Arg Arg Cys Asn
            20

<210> SEQ ID NO 169
<211> LENGTH: 21
<212> TYPE: PRT
<213> ORGANISM: Artificial

```
<220> FEATURE:
<223> OTHER INFORMATION: Synthetic antimicrobial peptide

<400> SEQUENCE: 169

Gly Phe Cys Gly Arg Val Cys Val Tyr Arg Asn Gly Val Arg Leu Cys
1               5                   10                  15

Tyr Arg Arg Cys Asn
            20

<210> SEQ ID NO 170
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 170

Gly Phe Cys Gly Arg Val Cys Val Tyr Arg Asn Gly Val Arg Arg Cys
1               5                   10                  15

Tyr Arg Arg Cys Asn
            20

<210> SEQ ID NO 171
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 171

Gly Phe Cys Gly Arg Val Cys Val Tyr Arg Asn Gly Val Arg Thr Cys
1               5                   10                  15

Tyr Arg Arg Cys Asn
            20

<210> SEQ ID NO 172
<211> LENGTH: 21
<212> TYPE: PRT
<213> ORGANISM: Artificial sequence
<220> FEATURE:
<223> OTHER INFORMATION: Synthetic construct

<400> SEQUENCE: 172

Gly Phe Cys Gly Arg Val Cys Val Arg Arg Asn Gly Val Arg Val Cys
1               5                   10                  15

Tyr Arg Arg Cys Asn
            20

<210> SEQ ID NO 173
<211> LENGTH: 21
<212> TYPE: PRT
<213> ORGANISM: Artificial sequence
<220> FEATURE:
<223> OTHER INFORMATION: Synthetic construct

<400> SEQUENCE: 173

Gly Phe Cys Gly Ser Val Cys Val Tyr Arg Asn Gly Val Arg Ala Cys
1               5                   10                  15

Tyr Arg Arg Cys Asn
            20

<210> SEQ ID NO 174
<211> LENGTH: 21
<212> TYPE: PRT
```

```
<213> ORGANISM: Artificial
<220> FEATURE:
<223> OTHER INFORMATION: Synthetic antimicrobial peptide

<400> SEQUENCE: 174

Gly Phe Cys Gly Ser Val Cys Val Tyr Arg Asn Gly Val Arg Lys Cys
1               5                   10                  15

Tyr Arg Arg Cys Asn
            20

<210> SEQ ID NO 175
<211> LENGTH: 21
<212> TYPE: PRT
<213> ORGANISM: Artificial sequence
<220> FEATURE:
<223> OTHER INFORMATION: Synthetic construct

<400> SEQUENCE: 175

Gly Phe Cys Gly Ser Val Cys Val Tyr Arg Asn Gly Val Arg Arg Cys
1               5                   10                  15

Tyr Arg Arg Cys Asn
            20

<210> SEQ ID NO 176
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 176

Gly Phe Cys Gly Tyr Val Cys Val Arg Arg Asn Gly Val Arg Ser Cys
1               5                   10                  15

Tyr Arg Arg Cys Asn
            20

<210> SEQ ID NO 177
<211> LENGTH: 21
<212> TYPE: PRT
<213> ORGANISM: Artificial sequence
<220> FEATURE:
<223> OTHER INFORMATION: Synthetic construct

<400> SEQUENCE: 177

Gly Phe Cys Ile Asn Val Cys Val Tyr Arg Asn Gly Val Arg Val Cys
1               5                   10                  15

His Arg Arg Cys Asn
            20

<210> SEQ ID NO 178
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 178

Gly Phe Cys Leu His Val Cys Val Tyr Arg Asn Gly Val Arg Gln Cys
1               5                   10                  15

Tyr Arg Arg Cys Asn
            20

<210> SEQ ID NO 179
<211> LENGTH: 21
```

```
<212> TYPE: PRT
<213> ORGANISM: Artificial sequence
<220> FEATURE:
<223> OTHER INFORMATION: Synthetic construct

<400> SEQUENCE: 179

Gly Phe Cys Leu Lys Val Cys Val Tyr Arg Asn Gly Val Arg Lys Cys
1               5                   10                  15

Tyr Arg Arg Cys Asn
            20

<210> SEQ ID NO 180
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 180

Gly Phe Cys Leu Arg Val Cys Val Tyr Arg Asn Gly Val Arg Gln Cys
1               5                   10                  15

Tyr Arg Arg Cys Asn
            20

<210> SEQ ID NO 181
<211> LENGTH: 21
<212> TYPE: PRT
<213> ORGANISM: Artificial sequence
<220> FEATURE:
<223> OTHER INFORMATION: Synthetic construct

<400> SEQUENCE: 181

Gly Phe Cys Leu Arg Val Cys Val Tyr Arg Asn Gly Val Arg Ser Cys
1               5                   10                  15

Tyr Arg Arg Cys Asn
            20

<210> SEQ ID NO 182
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 182

Gly Phe Cys Met Glu Val Cys Val Tyr Arg Asn Gly Val Arg Val Cys
1               5                   10                  15

Thr Arg Arg Cys Asn
            20

<210> SEQ ID NO 183
<211> LENGTH: 21
<212> TYPE: PRT
<213> ORGANISM: Artificial sequence
<220> FEATURE:
<223> OTHER INFORMATION: Synthetic construct

<400> SEQUENCE: 183

Gly Phe Cys Met His Val Cys Val Tyr Arg Asn Gly Val Arg Ser Cys
1               5                   10                  15

Tyr Arg Arg Cys Asn
            20

<210> SEQ ID NO 184
```

```
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 184

Gly Phe Cys Met Asn Val Cys Val Tyr Arg Asn Gly Val Arg Val Cys
1               5                   10                  15

His Arg Arg Cys Asn
            20

<210> SEQ ID NO 185
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 185

Gly Phe Cys Met Arg Val Cys Val Tyr Arg Asn Gly Val Arg Thr Cys
1               5                   10                  15

Tyr Arg Arg Cys Asn
            20

<210> SEQ ID NO 186
<211> LENGTH: 21
<212> TYPE: PRT
<213> ORGANISM: Artificial sequence
<220> FEATURE:
<223> OTHER INFORMATION: Synthetic construct

<400> SEQUENCE: 186

Gly Phe Cys Met Ser Val Cys Val Tyr Arg Asn Gly Val Arg Gln Cys
1               5                   10                  15

Tyr Arg Arg Cys Asn
            20

<210> SEQ ID NO 187
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 187

Gly Phe Cys Met Ser Val Cys Val Tyr Arg Asn Gly Val Arg Arg Cys
1               5                   10                  15

Tyr Arg Arg Cys Asn
            20

<210> SEQ ID NO 188
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 188

Gly Phe Cys Asn Arg Val Cys Val Tyr Arg Asn Gly Val Arg Ile Cys
1               5                   10                  15

Tyr Arg Arg Cys Asn
            20
```

```
<210> SEQ ID NO 189
<211> LENGTH: 21
<212> TYPE: PRT
<213> ORGANISM: Artificial sequence
<220> FEATURE:
<223> OTHER INFORMATION: Synthetic construct

<400> SEQUENCE: 189

Gly Phe Cys Ser Lys Val Cys Val Tyr Arg Asn Gly Val Arg Arg Cys
1               5                   10                  15

Tyr Arg Arg Cys Asn
            20

<210> SEQ ID NO 190
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 190

Gly Phe Cys Ser Arg Val Cys Val Tyr Arg Asn Gly Val Arg Ile Cys
1               5                   10                  15

Tyr Arg Arg Cys Asn
            20

<210> SEQ ID NO 191
<211> LENGTH: 21
<212> TYPE: PRT
<213> ORGANISM: Artificial sequence
<220> FEATURE:
<223> OTHER INFORMATION: Synthetic construct

<400> SEQUENCE: 191

Gly Phe Cys Thr Asn Val Cys Val Tyr Arg Asn Gly Val Arg Ala Cys
1               5                   10                  15

Tyr Arg Arg Cys Asn
            20

<210> SEQ ID NO 192
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 192

Gly Phe Cys Thr Arg Val Cys Val Tyr Arg Asn Gly Val Arg Arg Cys
1               5                   10                  15

Tyr Arg Arg Cys Asn
            20

<210> SEQ ID NO 193
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 193

Gly Phe Cys Thr Arg Val Cys Val Tyr Arg Asn Gly Val Arg Thr Cys
1               5                   10                  15

Tyr Arg Arg Cys Asn
            20
```

<210> SEQ ID NO 194
<211> LENGTH: 21
<212> TYPE: PRT
<213> ORGANISM: Artificial sequence
<220> FEATURE:
<223> OTHER INFORMATION: Synthetic construct

<400> SEQUENCE: 194

Gly Phe Cys Thr Ser Val Cys Val Tyr Arg Asn Gly Val Arg His Cys
1               5                   10                  15

Tyr Arg Arg Cys Asn
            20

<210> SEQ ID NO 195
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 195

Gly Phe Cys Thr Tyr Val Cys Val Lys Arg Asn Gly Val Arg Lys Cys
1               5                   10                  15

Tyr Arg Arg Cys Asn
            20

<210> SEQ ID NO 196
<211> LENGTH: 21
<212> TYPE: PRT
<213> ORGANISM: Artificial sequence
<220> FEATURE:
<223> OTHER INFORMATION: Synthetic construct

<400> SEQUENCE: 196

Gly Phe Cys Val His Val Cys Val Tyr Arg Asn Gly Val Arg Pro Cys
1               5                   10                  15

Tyr Arg Arg Cys Asn
            20

<210> SEQ ID NO 197
<211> LENGTH: 21
<212> TYPE: PRT
<213> ORGANISM: Artificial sequence
<220> FEATURE:
<223> OTHER INFORMATION: Synthetic construct

<400> SEQUENCE: 197

Gly Phe Cys Val His Val Cys Val Tyr Arg Asn Gly Val Arg Val Cys
1               5                   10                  15

His Arg Arg Cys Asn
            20

<210> SEQ ID NO 198
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 198

Gly Phe Cys Val Lys Val Cys Val Tyr Arg Asn Gly Val Arg Gln Cys
1               5                   10                  15

Tyr Arg Arg Cys Asn
            20

```
<210> SEQ ID NO 199
<211> LENGTH: 21
<212> TYPE: PRT
<213> ORGANISM: Artificial sequence
<220> FEATURE:
<223> OTHER INFORMATION: Synthetic construct

<400> SEQUENCE: 199

Gly Phe Cys Val Asn Val Cys Val Tyr Arg Asn Gly Val Arg Val Cys
1               5                   10                  15

His Arg Arg Cys Asn
            20

<210> SEQ ID NO 200
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 200

Gly Phe Cys Val Arg Val Cys Val Tyr Arg Asn Gly Val Arg Gly Cys
1               5                   10                  15

Tyr Arg Arg Cys Asn
            20

<210> SEQ ID NO 201
<211> LENGTH: 21
<212> TYPE: PRT
<213> ORGANISM: Artificial sequence
<220> FEATURE:
<223> OTHER INFORMATION: Synthetic construct

<400> SEQUENCE: 201

Gly Phe Cys Val Arg Val Cys Val Tyr Arg Asn Gly Val Arg Pro Cys
1               5                   10                  15

Tyr Arg Arg Cys Asn
            20

<210> SEQ ID NO 202
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 202

Gly Phe Cys Val Arg Val Cys Val Tyr Arg Asn Gly Val Arg Gln Cys
1               5                   10                  15

Tyr Arg Arg Cys Asn
            20

<210> SEQ ID NO 203
<211> LENGTH: 21
<212> TYPE: PRT
<213> ORGANISM: Artificial sequence
<220> FEATURE:
<223> OTHER INFORMATION: Synthetic construct

<400> SEQUENCE: 203

Gly Phe Cys Val Arg Val Cys Val Tyr Arg Asn Gly Val Arg Arg Cys
1               5                   10                  15

Tyr Arg Arg Cys Asn
```

20

<210> SEQ ID NO 204
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 204

Gly Phe Cys Val Arg Val Cys Val Tyr Arg Asn Gly Val Arg Thr Cys
1               5                   10                  15

Tyr Arg Arg Cys Asn
            20

<210> SEQ ID NO 205
<211> LENGTH: 21
<212> TYPE: PRT
<213> ORGANISM: Artificial sequence
<220> FEATURE:
<223> OTHER INFORMATION: Synthetic construct

<400> SEQUENCE: 205

Gly Phe Cys Tyr His Val Cys Val Tyr Arg Asn Gly Val Arg Tyr Cys
1               5                   10                  15

Tyr Arg Arg Cys Asn
            20

<210> SEQ ID NO 206
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 206

Gly Phe Cys Tyr Lys Val Cys Val Tyr Arg Asn Gly Val Arg Ser Cys
1               5                   10                  15

Tyr Arg Arg Cys Asn
            20

<210> SEQ ID NO 207
<211> LENGTH: 21
<212> TYPE: PRT
<213> ORGANISM: Artificial sequence
<220> FEATURE:
<223> OTHER INFORMATION: Synthetic construct

<400> SEQUENCE: 207

Gly Phe Cys Tyr Asn Val Cys Val Tyr Arg Asn Gly Val Arg Arg Cys
1               5                   10                  15

Tyr Arg Arg Cys Asn
            20

<210> SEQ ID NO 208
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 208

Gly Phe Cys Tyr Asn Val Cys Val Tyr Arg Asn Gly Val Arg Val Cys
1               5                   10                  15

```
His Arg Arg Cys Asn
            20

<210> SEQ ID NO 209
<211> LENGTH: 21
<212> TYPE: PRT
<213> ORGANISM: Artificial sequence
<220> FEATURE:
<223> OTHER INFORMATION: Synthetic construct

<400> SEQUENCE: 209

Gly Phe Cys Tyr Arg Val Cys Val Tyr Arg Asn Gly Val Arg Thr Cys
1               5                   10                  15

Tyr Arg Arg Cys Asn
            20

<210> SEQ ID NO 210
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 210

Gly Phe Cys Tyr Arg Val Cys Val Tyr Arg Asn Gly Val Arg Val Cys
1               5                   10                  15

His Arg Arg Cys Asn
            20

<210> SEQ ID NO 211
<211> LENGTH: 21
<212> TYPE: PRT
<213> ORGANISM: Artificial sequence
<220> FEATURE:
<223> OTHER INFORMATION: Synthetic construct

<400> SEQUENCE: 211

Gly Phe Cys Tyr Arg Val Cys Val Tyr Arg Asn Gly Val Arg Val Cys
1               5                   10                  15

Ser Arg Arg Cys Asn
            20

<210> SEQ ID NO 212
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 212

Gly Phe Cys Tyr Trp Val Cys Val Tyr Arg Asn Gly Val Arg Ser Cys
1               5                   10                  15

Tyr Arg Arg Cys Asn
            20

<210> SEQ ID NO 213
<211> LENGTH: 21
<212> TYPE: PRT
<213> ORGANISM: Artificial sequence
<220> FEATURE:
<223> OTHER INFORMATION: Synthetic construct

<400> SEQUENCE: 213

Gly Phe Cys Trp His Val Cys Val Tyr Arg Asn Gly Ala Arg Ser Cys
1               5                   10                  15
```

Tyr Arg Arg Cys Asn
            20

<210> SEQ ID NO 214
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 214

Gly Phe Cys Trp His Val Cys Val Tyr Arg Asn Gly Ser Arg Ser Cys
1               5                   10                  15

Tyr Arg Arg Cys Asn
            20

<210> SEQ ID NO 215
<211> LENGTH: 21
<212> TYPE: PRT
<213> ORGANISM: Artificial sequence
<220> FEATURE:
<223> OTHER INFORMATION: Synthetic construct

<400> SEQUENCE: 215

Gly Phe Cys Trp His Val Cys Val Tyr Arg Asn Gly Val Arg Ser Cys
1               5                   10                  15

Ser Arg Arg Cys Asn
            20

<210> SEQ ID NO 216
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 216

Gly Phe Cys Trp His Val Cys Ala Tyr Arg Asn Gly Lys Arg Val Cys
1               5                   10                  15

Tyr Arg Arg Cys Asn
            20

<210> SEQ ID NO 217
<211> LENGTH: 21
<212> TYPE: PRT
<213> ORGANISM: Artificial sequence
<220> FEATURE:
<223> OTHER INFORMATION: Synthetic construct

<400> SEQUENCE: 217

Gly Phe Cys Trp His Val Cys Ala Tyr Arg Asn Gly Val Arg Ser Cys
1               5                   10                  15

Tyr Arg Arg Cys Asn
            20

<210> SEQ ID NO 218
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 218

Gly Phe Cys Trp His Val Cys Ala Arg Arg Asn Gly Val Arg Val Cys

```
1               5                   10                  15

Tyr Arg Arg Cys Asn
            20

<210> SEQ ID NO 219
<211> LENGTH: 21
<212> TYPE: PRT
<213> ORGANISM: Artificial sequence
<220> FEATURE:
<223> OTHER INFORMATION: Synthetic construct

<400> SEQUENCE: 219

Gly Phe Cys Trp His Val Cys His Tyr Arg Asn Ser Val Arg Val Cys
1               5                   10                  15

Tyr Arg Arg Cys Asn
            20

<210> SEQ ID NO 220
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 220

Gly Phe Cys Trp His Val Cys Val Ser Arg Asn Gly Val Arg Lys Cys
1               5                   10                  15

Tyr Arg Arg Cys Asn
            20

<210> SEQ ID NO 221
<211> LENGTH: 21
<212> TYPE: PRT
<213> ORGANISM: Artificial sequence
<220> FEATURE:
<223> OTHER INFORMATION: Synthetic construct

<400> SEQUENCE: 221

Gly Phe Cys Trp Lys Val Cys Val Ser Arg Asn Gly Val Arg Val Cys
1               5                   10                  15

Ser Arg Arg Cys Asn
            20

<210> SEQ ID NO 222
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 222

Gly Phe Cys Trp Asn Val Cys Val Tyr Arg Asn Ala Val Arg Val Cys
1               5                   10                  15

His Arg Arg Cys Asn
            20

<210> SEQ ID NO 223
<211> LENGTH: 21
<212> TYPE: PRT
<213> ORGANISM: Artificial sequence
<220> FEATURE:
<223> OTHER INFORMATION: Synthetic construct

<400> SEQUENCE: 223
```

```
Gly Phe Cys Trp Asn Val Cys Val Tyr Arg Asn Asp Val Arg Val Cys
1               5                   10                  15

His Arg Arg Cys Asn
            20

<210> SEQ ID NO 224
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 224

Gly Phe Cys Trp Asn Val Cys Val Tyr Arg Asn Glu Val Arg Val Cys
1               5                   10                  15

His Arg Arg Cys Asn
            20

<210> SEQ ID NO 225
<211> LENGTH: 21
<212> TYPE: PRT
<213> ORGANISM: Artificial sequence
<220> FEATURE:
<223> OTHER INFORMATION: Synthetic construct

<400> SEQUENCE: 225

Gly Phe Cys Trp Asn Val Cys Val Tyr Arg Asn Phe Val Arg Val Cys
1               5                   10                  15

His Arg Arg Cys Asn
            20

<210> SEQ ID NO 226
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 226

Gly Phe Cys Trp Asn Val Cys Val Tyr Arg Asn His Val Arg Val Cys
1               5                   10                  15

His Arg Arg Cys Asn
            20

<210> SEQ ID NO 227
<211> LENGTH: 21
<212> TYPE: PRT
<213> ORGANISM: Artificial sequence
<220> FEATURE:
<223> OTHER INFORMATION: Synthetic construct

<400> SEQUENCE: 227

Gly Phe Cys Trp Asn Val Cys Val Tyr Arg Asn Lys Val Arg Val Cys
1               5                   10                  15

His Arg Arg Cys Asn
            20

<210> SEQ ID NO 228
<211> LENGTH: 21
<212> TYPE: PRT
<213> ORGANISM: Artificial sequence
<220> FEATURE:
<223> OTHER INFORMATION: Synthetic construct

<400> SEQUENCE: 228
```

```
Gly Phe Cys Trp Asn Val Cys Val Tyr Arg Asn Arg Val Arg Val Cys
1               5                   10                  15

His Arg Arg Cys Asn
            20

<210> SEQ ID NO 229
<211> LENGTH: 21
<212> TYPE: PRT
<213> ORGANISM: Artificial sequence
<220> FEATURE:
<223> OTHER INFORMATION: Synthetic construct

<400> SEQUENCE: 229

Gly Phe Cys Trp Asn Val Cys Val Tyr Arg Asn Tyr Val Arg Val Cys
1               5                   10                  15

His Arg Arg Cys Asn
            20

<210> SEQ ID NO 230
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 230

Gly Phe Cys Trp Asn Val Cys Val Tyr Arg Ala Gly Val Arg Val Cys
1               5                   10                  15

His Arg Arg Cys Asn
            20

<210> SEQ ID NO 231
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 231

Gly Phe Cys Trp Asn Val Cys Val Tyr Arg Gly Gly Val Arg Val Cys
1               5                   10                  15

His Arg Arg Cys Asn
            20

<210> SEQ ID NO 232
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 232

Gly Phe Cys Trp Asn Val Cys Val Tyr Arg His Gly Val Arg Val Cys
1               5                   10                  15

His Arg Arg Cys Asn
            20

<210> SEQ ID NO 233
<211> LENGTH: 21
<212> TYPE: PRT
<213> ORGANISM: Artificial sequence
<220> FEATURE:
<223> OTHER INFORMATION: Synthetic construct
```

-continued

<400> SEQUENCE: 233

Gly Phe Cys Trp Asn Val Cys Val Tyr Arg Gln Gly Val Arg Val Cys
1               5                   10                  15

His Arg Arg Cys Asn
            20

<210> SEQ ID NO 234
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 234

Gly Phe Cys Trp Asn Val Cys Val Tyr Arg Arg Gly Val Arg Val Cys
1               5                   10                  15

His Arg Arg Cys Asn
            20

<210> SEQ ID NO 235
<211> LENGTH: 21
<212> TYPE: PRT
<213> ORGANISM: Artificial sequence
<220> FEATURE:
<223> OTHER INFORMATION: Synthetic construct

<400> SEQUENCE: 235

Gly Phe Cys Trp Asn Val Cys Val Tyr Arg Asn Gly Ala Arg Val Cys
1               5                   10                  15

His Arg Arg Cys Asn
            20

<210> SEQ ID NO 236
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 236

Gly Phe Cys Trp Asn Val Cys Val Tyr Arg Asn Gly Phe Arg Val Cys
1               5                   10                  15

His Arg Arg Cys Asn
            20

<210> SEQ ID NO 237
<211> LENGTH: 21
<212> TYPE: PRT
<213> ORGANISM: Artificial sequence
<220> FEATURE:
<223> OTHER INFORMATION: Synthetic construct

<400> SEQUENCE: 237

Gly Phe Cys Trp Asn Val Cys Val Tyr Arg Asn Gly His Arg Val Cys
1               5                   10                  15

His Arg Arg Cys Asn
            20

<210> SEQ ID NO 238
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 238

Gly Phe Cys Trp Asn Val Cys Val Tyr Arg Asn Gly Gln Arg Val Cys
1               5                   10                  15

His Arg Arg Cys Asn
            20

<210> SEQ ID NO 239
<211> LENGTH: 21
<212> TYPE: PRT
<213> ORGANISM: Artificial sequence
<220> FEATURE:
<223> OTHER INFORMATION: Synthetic construct

<400> SEQUENCE: 239

Gly Phe Cys Trp Asn Val Cys Val Tyr Arg Asn Gly Arg Arg Val Cys
1               5                   10                  15

His Arg Arg Cys Asn
            20

<210> SEQ ID NO 240
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 240

Gly Phe Cys Trp Asn Val Cys Val Tyr Arg Asn Gly Thr Arg Val Cys
1               5                   10                  15

His Arg Arg Cys Asn
            20

<210> SEQ ID NO 241
<211> LENGTH: 21
<212> TYPE: PRT
<213> ORGANISM: Artificial sequence
<220> FEATURE:
<223> OTHER INFORMATION: Synthetic construct

<400> SEQUENCE: 241

Gly Phe Cys Trp Asn Val Cys Val Tyr Arg Asn Gly Trp Arg Val Cys
1               5                   10                  15

His Arg Arg Cys Asn
            20

<210> SEQ ID NO 242
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 242

Gly Phe Cys Trp Asn Val Cys Val Tyr Arg Asn Gly Tyr Arg Val Cys
1               5                   10                  15

His Arg Arg Cys Asn
            20

<210> SEQ ID NO 243
<211> LENGTH: 21
<212> TYPE: PRT
<213> ORGANISM: Artificial sequence
<220> FEATURE:

```
<223> OTHER INFORMATION: Synthetic construct

<400> SEQUENCE: 243

Gly Phe Cys Trp Asn Val Cys Val Tyr Arg Asn Gly Val Arg Ala Cys
1               5                   10                  15

His Arg Arg Cys Asn
            20

<210> SEQ ID NO 244
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 244

Gly Phe Cys Trp Asn Val Cys Val Tyr Arg Asn Gly Val Arg Cys Cys
1               5                   10                  15

His Arg Arg Cys Asn
            20

<210> SEQ ID NO 245
<211> LENGTH: 21
<212> TYPE: PRT
<213> ORGANISM: Artificial sequence
<220> FEATURE:
<223> OTHER INFORMATION: Synthetic construct

<400> SEQUENCE: 245

Gly Phe Cys Trp Asn Val Cys Val Tyr Arg Asn Gly Val Arg Phe Cys
1               5                   10                  15

His Arg Arg Cys Asn
            20

<210> SEQ ID NO 246
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 246

Gly Phe Cys Trp Asn Val Cys Val Tyr Arg Asn Gly Val Arg Gly Cys
1               5                   10                  15

His Arg Arg Cys Asn
            20

<210> SEQ ID NO 247
<211> LENGTH: 21
<212> TYPE: PRT
<213> ORGANISM: Artificial sequence
<220> FEATURE:
<223> OTHER INFORMATION: Synthetic construct

<400> SEQUENCE: 247

Gly Phe Cys Trp Asn Val Cys Val Tyr Arg Asn Gly Val Arg His Cys
1               5                   10                  15

His Arg Arg Cys Asn
            20

<210> SEQ ID NO 248
<211> LENGTH: 21
<212> TYPE: PRT
<213> ORGANISM: Artificial
```

```
<220> FEATURE:
<223> OTHER INFORMATION: Synthetic antimicrobial peptide

<400> SEQUENCE: 248

Gly Phe Cys Trp Asn Val Cys Val Tyr Arg Asn Gly Val Arg Ile Cys
1               5                   10                  15

His Arg Arg Cys Asn
            20

<210> SEQ ID NO 249
<211> LENGTH: 21
<212> TYPE: PRT
<213> ORGANISM: Artificial sequence
<220> FEATURE:
<223> OTHER INFORMATION: Synthetic construct

<400> SEQUENCE: 249

Gly Phe Cys Trp Asn Val Cys Val Tyr Arg Asn Gly Val Arg Leu Cys
1               5                   10                  15

His Arg Arg Cys Asn
            20

<210> SEQ ID NO 250
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 250

Gly Phe Cys Trp Asn Val Cys Val Tyr Arg Asn Gly Val Arg Met Cys
1               5                   10                  15

His Arg Arg Cys Asn
            20

<210> SEQ ID NO 251
<211> LENGTH: 21
<212> TYPE: PRT
<213> ORGANISM: Artificial sequence
<220> FEATURE:
<223> OTHER INFORMATION: Synthetic construct

<400> SEQUENCE: 251

Gly Phe Cys Trp Asn Val Cys Val Tyr Arg Asn Gly Val Arg Asn Cys
1               5                   10                  15

His Arg Arg Cys Asn
            20

<210> SEQ ID NO 252
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 252

Gly Phe Cys Trp Asn Val Cys Val Tyr Arg Asn Gly Val Arg Arg Cys
1               5                   10                  15

His Arg Arg Cys Asn
            20

<210> SEQ ID NO 253
<211> LENGTH: 21
<212> TYPE: PRT
```

<213> ORGANISM: Artificial sequence
<220> FEATURE:
<223> OTHER INFORMATION: Synthetic construct

<400> SEQUENCE: 253

Gly Phe Cys Trp Asn Val Cys Val Tyr Arg Asn Gly Val Arg Trp Cys
1               5                   10                  15

His Arg Arg Cys Asn
            20

<210> SEQ ID NO 254
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 254

Gly Phe Cys Trp Asn Val Cys Val Tyr Arg Asn Gly Val Arg Tyr Cys
1               5                   10                  15

His Arg Arg Cys Asn
            20

<210> SEQ ID NO 255
<211> LENGTH: 21
<212> TYPE: PRT
<213> ORGANISM: Artificial sequence
<220> FEATURE:
<223> OTHER INFORMATION: Synthetic construct

<400> SEQUENCE: 255

Gly Phe Cys Trp Asn Ala Cys Val Tyr Arg Asn Gly Val Arg Asn Cys
1               5                   10                  15

Tyr Arg Arg Cys Asn
            20

<210> SEQ ID NO 256
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 256

Gly Phe Cys Trp Asn Ala Cys Val Tyr Arg Asn Gly Val Arg Ser Cys
1               5                   10                  15

Tyr Arg Arg Cys Asn
            20

<210> SEQ ID NO 257
<211> LENGTH: 21
<212> TYPE: PRT
<213> ORGANISM: Artificial sequence
<220> FEATURE:
<223> OTHER INFORMATION: Synthetic construct

<400> SEQUENCE: 257

Gly Phe Cys Trp Asn Ala Cys Val Tyr Arg Asn Gly Val Arg Val Cys
1               5                   10                  15

His Arg Arg Cys Asn
            20

<210> SEQ ID NO 258
<211> LENGTH: 21

```
<212> TYPE: PRT
<213> ORGANISM: Artificial sequence
<220> FEATURE:
<223> OTHER INFORMATION: Synthetic construct

<400> SEQUENCE: 258

Gly Phe Cys Trp Asn Ala Cys Val Lys Arg Asn Gly Val Arg Val Cys
1               5                   10                  15

Tyr Arg Arg Cys Asn
            20

<210> SEQ ID NO 259
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 259

Gly Phe Cys Trp Asn Cys Cys Val Tyr Arg Asn Gly Val Arg Val Cys
1               5                   10                  15

His Arg Arg Cys Asn
            20

<210> SEQ ID NO 260
<211> LENGTH: 21
<212> TYPE: PRT
<213> ORGANISM: Artificial sequence
<220> FEATURE:
<223> OTHER INFORMATION: Synthetic construct

<400> SEQUENCE: 260

Gly Phe Cys Trp Asn Phe Cys Val Tyr Arg Asn Gly Val Arg Val Cys
1               5                   10                  15

His Arg Arg Cys Asn
            20

<210> SEQ ID NO 261
<211> LENGTH: 21
<212> TYPE: PRT
<213> ORGANISM: Artificial sequence
<220> FEATURE:
<223> OTHER INFORMATION: Synthetic construct

<400> SEQUENCE: 261

Gly Phe Cys Trp Asn His Cys Val Tyr Arg Asn Gly Val Arg Val Cys
1               5                   10                  15

His Arg Arg Cys Asn
            20

<210> SEQ ID NO 262
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 262

Gly Phe Cys Trp Asn Ile Cys Val Tyr Arg Asn Gly Val Arg Val Cys
1               5                   10                  15

His Arg Arg Cys Asn
            20

<210> SEQ ID NO 263
```

<211> LENGTH: 21
<212> TYPE: PRT
<213> ORGANISM: Artificial sequence
<220> FEATURE:
<223> OTHER INFORMATION: Synthetic construct

<400> SEQUENCE: 263

Gly Phe Cys Trp Asn Leu Cys Val Tyr Arg Asn Gly Val Arg Val Cys
1               5                   10                  15

His Arg Arg Cys Asn
            20

<210> SEQ ID NO 264
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 264

Gly Phe Cys Trp Asn Met Cys Val Tyr Arg Asn Gly Val Arg Val Cys
1               5                   10                  15

His Arg Arg Cys Asn
            20

<210> SEQ ID NO 265
<211> LENGTH: 21
<212> TYPE: PRT
<213> ORGANISM: Artificial sequence
<220> FEATURE:
<223> OTHER INFORMATION: Synthetic construct

<400> SEQUENCE: 265

Gly Phe Cys Trp Asn Gln Cys Val Tyr Arg Asn Gly Val Arg Val Cys
1               5                   10                  15

His Arg Arg Cys Asn
            20

<210> SEQ ID NO 266
<211> LENGTH: 21
<212> TYPE: PRT
<213> ORGANISM: Artificial sequence
<220> FEATURE:
<223> OTHER INFORMATION: Synthetic construct

<400> SEQUENCE: 266

Gly Phe Cys Trp Asn Thr Cys Val Tyr Arg Asn Gly Val Arg Val Cys
1               5                   10                  15

His Arg Arg Cys Asn
            20

<210> SEQ ID NO 267
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 267

Gly Phe Cys Trp Asn Trp Cys Val Tyr Arg Asn Gly Val Arg Val Cys
1               5                   10                  15

His Arg Arg Cys Asn
            20

```
<210> SEQ ID NO 268
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 268

Gly Phe Cys Trp Asn Tyr Cys Val Tyr Arg Asn Gly Val Arg Val Cys
1               5                   10                  15

His Arg Arg Cys Asn
            20

<210> SEQ ID NO 269
<211> LENGTH: 21
<212> TYPE: PRT
<213> ORGANISM: Artificial sequence
<220> FEATURE:
<223> OTHER INFORMATION: Synthetic construct

<400> SEQUENCE: 269

Gly Phe Cys Trp Asn Val Cys Ala Tyr Arg Asn Gly Ala Arg Val Cys
1               5                   10                  15

Tyr Arg Arg Cys Asn
            20

<210> SEQ ID NO 270
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 270

Gly Phe Cys Trp Asn Val Cys Ala Tyr Arg Asn Gly Val Arg Ser Cys
1               5                   10                  15

Tyr Arg Arg Cys Asn
            20

<210> SEQ ID NO 271
<211> LENGTH: 21
<212> TYPE: PRT
<213> ORGANISM: Artificial sequence
<220> FEATURE:
<223> OTHER INFORMATION: Synthetic construct

<400> SEQUENCE: 271

Gly Phe Cys Trp Asn Val Cys Ala Tyr Arg Asn Gly Val Arg Val Cys
1               5                   10                  15

His Arg Arg Cys Asn
            20

<210> SEQ ID NO 272
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 272

Gly Phe Cys Trp Asn Val Cys Phe Tyr Arg Asn Gly Val Arg Val Cys
1               5                   10                  15

His Arg Arg Cys Asn
            20
```

<210> SEQ ID NO 273
<211> LENGTH: 21
<212> TYPE: PRT
<213> ORGANISM: Artificial sequence
<220> FEATURE:
<223> OTHER INFORMATION: Synthetic construct

<400> SEQUENCE: 273

Gly Phe Cys Trp Asn Val Cys Gly Tyr Arg Asn Gly Val Arg Val Cys
1               5                   10                  15

His Arg Arg Cys Asn
            20

<210> SEQ ID NO 274
<211> LENGTH: 21
<212> TYPE: PRT
<213> ORGANISM: Artificial sequence
<220> FEATURE:
<223> OTHER INFORMATION: Synthetic construct

<400> SEQUENCE: 274

Gly Phe Cys Trp Asn Val Cys Ile Tyr Arg Asn Gly Val Arg Val Cys
1               5                   10                  15

His Arg Arg Cys Asn
            20

<210> SEQ ID NO 275
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 275

Gly Phe Cys Trp Asn Val Cys Leu Tyr Arg Asn Gly Val Arg Val Cys
1               5                   10                  15

His Arg Arg Cys Asn
            20

<210> SEQ ID NO 276
<211> LENGTH: 21
<212> TYPE: PRT
<213> ORGANISM: Artificial sequence
<220> FEATURE:
<223> OTHER INFORMATION: Synthetic construct

<400> SEQUENCE: 276

Gly Phe Cys Trp Asn Val Cys Trp Tyr Arg Asn Gly Val Arg Val Cys
1               5                   10                  15

His Arg Arg Cys Asn
            20

<210> SEQ ID NO 277
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 277

Gly Phe Cys Trp Asn Val Cys Tyr Tyr Arg Asn Gly Val Arg Val Cys
1               5                   10                  15

His Arg Arg Cys Asn
            20

<210> SEQ ID NO 278
<211> LENGTH: 21
<212> TYPE: PRT
<213> ORGANISM: Artificial sequence
<220> FEATURE:
<223> OTHER INFORMATION: Synthetic construct

<400> SEQUENCE: 278

Gly Phe Cys Trp Asn Val Cys Val Tyr Arg Asn Gly Val Arg Val Cys
1               5                   10                  15

His Arg Arg Cys Ala
            20

<210> SEQ ID NO 279
<211> LENGTH: 21
<212> TYPE: PRT
<213> ORGANISM: Artificial sequence
<220> FEATURE:
<223> OTHER INFORMATION: Synthetic construct

<400> SEQUENCE: 279

Gly Phe Cys Trp Asn Val Cys Val Tyr Arg Asn Gly Val Arg Val Cys
1               5                   10                  15

His Arg Arg Cys Cys
            20

<210> SEQ ID NO 280
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 280

Gly Phe Cys Trp Asn Val Cys Val Tyr Arg Asn Gly Val Arg Val Cys
1               5                   10                  15

His Arg Arg Cys Phe
            20

<210> SEQ ID NO 281
<211> LENGTH: 21
<212> TYPE: PRT
<213> ORGANISM: Artificial sequence
<220> FEATURE:
<223> OTHER INFORMATION: Synthetic construct

<400> SEQUENCE: 281

Gly Phe Cys Trp Asn Val Cys Val Tyr Arg Asn Gly Val Arg Val Cys
1               5                   10                  15

His Arg Arg Cys Gly
            20

<210> SEQ ID NO 282
<211> LENGTH: 21
<212> TYPE: PRT
<213> ORGANISM: Artificial sequence
<220> FEATURE:
<223> OTHER INFORMATION: Synthetic construct

<400> SEQUENCE: 282

Gly Phe Cys Trp Asn Val Cys Val Tyr Arg Asn Gly Val Arg Val Cys
1               5                   10                  15

His Arg Arg Cys His

20

<210> SEQ ID NO 283
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 283

Gly Phe Cys Trp Asn Val Cys Val Tyr Arg Asn Gly Val Arg Val Cys
1               5                   10                  15

His Arg Arg Cys Ile
            20

<210> SEQ ID NO 284
<211> LENGTH: 21
<212> TYPE: PRT
<213> ORGANISM: Artificial sequence
<220> FEATURE:
<223> OTHER INFORMATION: Synthetic construct

<400> SEQUENCE: 284

Gly Phe Cys Trp Asn Val Cys Val Tyr Arg Asn Gly Val Arg Val Cys
1               5                   10                  15

His Arg Arg Cys Lys
            20

<210> SEQ ID NO 285
<211> LENGTH: 21
<212> TYPE: PRT
<213> ORGANISM: Artificial sequence
<220> FEATURE:
<223> OTHER INFORMATION: Synthetic construct

<400> SEQUENCE: 285

Gly Phe Cys Trp Asn Val Cys Val Tyr Arg Asn Gly Val Arg Val Cys
1               5                   10                  15

His Arg Arg Cys Leu
            20

<210> SEQ ID NO 286
<211> LENGTH: 21
<212> TYPE: PRT
<213> ORGANISM: Artificial sequence
<220> FEATURE:
<223> OTHER INFORMATION: Synthetic construct

<400> SEQUENCE: 286

Gly Phe Cys Trp Asn Val Cys Val Tyr Arg Asn Gly Val Arg Val Cys
1               5                   10                  15

His Arg Arg Cys Met
            20

<210> SEQ ID NO 287
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 287

Gly Phe Cys Trp Asn Val Cys Val Tyr Arg Asn Gly Val Arg Val Cys
1               5                   10                  15

His Arg Arg Cys Pro
            20

<210> SEQ ID NO 288
<211> LENGTH: 21
<212> TYPE: PRT
<213> ORGANISM: Artificial sequence
<220> FEATURE:
<223> OTHER INFORMATION: Synthetic construct

<400> SEQUENCE: 288

Gly Phe Cys Trp Asn Val Cys Val Tyr Arg Asn Gly Val Arg Val Cys
1               5                   10                  15

His Arg Arg Cys Gln
            20

<210> SEQ ID NO 289
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 289

Gly Phe Cys Trp Asn Val Cys Val Tyr Arg Asn Gly Val Arg Val Cys
1               5                   10                  15

His Arg Arg Cys Arg
            20

<210> SEQ ID NO 290
<211> LENGTH: 21
<212> TYPE: PRT
<213> ORGANISM: Artificial sequence
<220> FEATURE:
<223> OTHER INFORMATION: Synthetic construct

<400> SEQUENCE: 290

Gly Phe Cys Trp Asn Val Cys Val Tyr Arg Asn Gly Val Arg Val Cys
1               5                   10                  15

His Arg Arg Cys Ser
            20

<210> SEQ ID NO 291
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 291

Gly Phe Cys Trp Asn Val Cys Val Tyr Arg Asn Gly Val Arg Val Cys
1               5                   10                  15

His Arg Arg Cys Trp
            20

<210> SEQ ID NO 292
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 292

Gly Phe Cys Trp Asn Val Cys Val Tyr Arg Asn Gly Val Arg Val Cys
1               5                   10                  15

His Arg Arg Cys Tyr
            20

<210> SEQ ID NO 293
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 293

Gly Phe Cys Trp Asn Val Cys Val Tyr Arg Asn Gly Val Arg Val Cys
1               5                   10                  15

His Arg Asp Cys Asn
            20

<210> SEQ ID NO 294
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 294

Gly Phe Cys Trp Asn Val Cys Val Tyr Arg Asn Gly Val Arg Val Cys
1               5                   10                  15

His Arg His Cys Asn
            20

<210> SEQ ID NO 295
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 295

Gly Phe Cys Trp Asn Val Cys Val Tyr Arg Asn Gly Val Arg Val Cys
1               5                   10                  15

His Arg Lys Cys Asn
            20

<210> SEQ ID NO 296
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 296

Gly Phe Cys Trp Asn Val Cys Val Tyr Arg Asn Gly Val Arg Val Cys
1               5                   10                  15

His Arg Met Cys Asn
            20

<210> SEQ ID NO 297
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 297

Gly Phe Cys Trp Asn Val Cys Val Tyr Arg Asn Gly Val Arg Val Cys

```
1               5                   10                  15
His Arg Thr Cys Asn
            20

<210> SEQ ID NO 298
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 298

Gly Phe Cys Trp Asn Val Cys Val Tyr Arg Asn Gly Val Arg Val Cys
1               5                   10                  15
His Arg Tyr Cys Asn
            20

<210> SEQ ID NO 299
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 299

Gly Phe Cys Trp Asn Val Cys Val Ala Arg Asn Gly Val Arg Val Cys
1               5                   10                  15
His Arg Arg Cys Asn
            20

<210> SEQ ID NO 300
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 300

Gly Phe Cys Trp Asn Val Cys Val Asp Arg Asn Gly Val Arg Val Cys
1               5                   10                  15
His Arg Arg Cys Asn
            20

<210> SEQ ID NO 301
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 301

Gly Phe Cys Trp Asn Val Cys Val Phe Arg Asn Gly Val Arg Val Cys
1               5                   10                  15
His Arg Arg Cys Asn
            20

<210> SEQ ID NO 302
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 302
```

```
Gly Phe Cys Trp Asn Val Cys Val Gly Arg Asn Gly Val Arg Val Cys
1               5                   10                  15

His Arg Arg Cys Asn
            20
```

<210> SEQ ID NO 303
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 303

```
Gly Phe Cys Trp Asn Val Cys Val His Arg Asn Gly Val Arg Val Cys
1               5                   10                  15

His Arg Arg Cys Asn
            20
```

<210> SEQ ID NO 304
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 304

```
Gly Phe Cys Trp Asn Val Cys Val Ile Arg Asn Gly Val Arg Val Cys
1               5                   10                  15

His Arg Arg Cys Asn
            20
```

<210> SEQ ID NO 305
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 305

```
Gly Phe Cys Trp Asn Val Cys Val Lys Arg Asn Gly Val Arg Val Cys
1               5                   10                  15

His Arg Arg Cys Asn
            20
```

<210> SEQ ID NO 306
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 306

```
Gly Phe Cys Trp Asn Val Cys Val Met Arg Asn Gly Val Arg Val Cys
1               5                   10                  15

His Arg Arg Cys Asn
            20
```

<210> SEQ ID NO 307
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 307

-continued

```
Gly Phe Cys Trp Asn Val Cys Val Gln Arg Asn Gly Val Arg Val Cys
1               5                   10                  15

His Arg Arg Cys Asn
            20

<210> SEQ ID NO 308
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 308

Gly Phe Cys Trp Asn Val Cys Val Arg Arg Asn Gly Val Arg Val Cys
1               5                   10                  15

His Arg Arg Cys Asn
            20

<210> SEQ ID NO 309
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 309

Gly Phe Cys Trp Asn Val Cys Val Ser Arg Asn Gly Val Arg Val Cys
1               5                   10                  15

His Arg Arg Cys Asn
            20

<210> SEQ ID NO 310
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 310

Gly Phe Cys Trp Asn Val Cys Val Thr Arg Asn Gly Val Arg Val Cys
1               5                   10                  15

His Arg Arg Cys Asn
            20

<210> SEQ ID NO 311
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 311

Gly Phe Cys Trp Asn Val Cys Val Val Arg Asn Gly Val Arg Val Cys
1               5                   10                  15

His Arg Arg Cys Asn
            20

<210> SEQ ID NO 312
<211> LENGTH: 21
<212> TYPE: PRT
<213> ORGANISM: Artificial
<220> FEATURE:
<223> OTHER INFORMATION: Synthetic antimicrobial peptide
```

<400> SEQUENCE: 312

Gly Phe Cys Trp Asn Val Cys Val Trp Arg Asn Gly Val Arg Val Cys
1               5                   10                  15

His Arg Arg Cys Asn
            20

<210> SEQ ID NO 313
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 313

Gly Phe Cys Trp Arg Val Cys Val Tyr Arg Asn Gly Ala Arg Lys Cys
1               5                   10                  15

Tyr Arg Arg Cys Asn
            20

<210> SEQ ID NO 314
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 314

Gly Phe Cys Trp Arg Val Cys Val Tyr Arg Asn Gly Ala Arg Val Cys
1               5                   10                  15

Ser Arg Arg Cys Asn
            20

<210> SEQ ID NO 315
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 315

Gly Phe Cys Trp Arg Val Cys Val Tyr Arg Asn Gly Val Arg Lys Cys
1               5                   10                  15

His Arg Arg Cys Asn
            20

<210> SEQ ID NO 316
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 316

Gly Phe Cys Trp Arg Val Cys Val Tyr Arg Asn Gly Val Arg Ser Cys
1               5                   10                  15

His Arg Arg Cys Asn
            20

<210> SEQ ID NO 317
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 317

Gly Phe Cys Trp Arg Val Cys Val Tyr Arg Asn Gly Val Arg Ser Cys
1               5                   10                  15

Ser Arg Arg Cys Asn
            20

<210> SEQ ID NO 318
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 318

Gly Phe Cys Trp Arg Ala Cys Val Tyr Arg Asn Ser Val Arg Val Cys
1               5                   10                  15

Tyr Arg Arg Cys Asn
            20

<210> SEQ ID NO 319
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 319

Gly Phe Cys Trp Arg Ala Cys Val Tyr Arg Asn Gly Val Arg Ala Cys
1               5                   10                  15

Tyr Arg Arg Cys Asn
            20

<210> SEQ ID NO 320
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 320

Gly Phe Cys Trp Arg Ala Cys Val Tyr Arg Asn Gly Val Arg Ser Cys
1               5                   10                  15

Tyr Arg Arg Cys Asn
            20

<210> SEQ ID NO 321
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 321

Gly Phe Cys Trp Arg Ala Cys Val Tyr Arg Asn Gly Val Arg Val Cys
1               5                   10                  15

His Arg Arg Cys Asn
            20

<210> SEQ ID NO 322
<211> LENGTH: 21
<212> TYPE: PRT
<213> ORGANISM: Artificial
<220> FEATURE:

<223> OTHER INFORMATION: Synthetic antimicrobial peptide

<400> SEQUENCE: 322

Gly Phe Cys Trp Arg Ala Cys Val Lys Arg Asn Gly Val Arg Val Cys
1               5                   10                  15

Tyr Arg Arg Cys Asn
            20

<210> SEQ ID NO 323
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 323

Gly Phe Cys Trp Arg Cys Cys Val Tyr Arg Asn Gly Val Arg Ser Cys
1               5                   10                  15

Tyr Arg Arg Cys Asn
            20

<210> SEQ ID NO 324
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 324

Gly Phe Cys Trp Arg Ser Cys Val Tyr Arg Asn Gly Val Arg Val Cys
1               5                   10                  15

His Arg Arg Cys Asn
            20

<210> SEQ ID NO 325
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 325

Gly Phe Cys Trp Arg Val Cys Ala Tyr Arg Asn Gly Val Arg Ser Cys
1               5                   10                  15

Tyr Arg Arg Cys Asn
            20

<210> SEQ ID NO 326
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 326

Gly Phe Cys Trp Arg Val Cys Gly Tyr Arg Asn Gly Val Arg Val Cys
1               5                   10                  15

His Arg Arg Cys Asn
            20

<210> SEQ ID NO 327
<211> LENGTH: 21
<212> TYPE: PRT
<213> ORGANISM: Artificial

```
<220> FEATURE:
<223> OTHER INFORMATION: Synthetic antimicrobial peptide

<400> SEQUENCE: 327

Gly Phe Cys Trp Arg Val Cys His Tyr Arg Asn Ser Val Arg Val Cys
1               5                   10                  15

Tyr Arg Arg Cys Asn
            20

<210> SEQ ID NO 328
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 328

Gly Phe Cys Trp Arg Val Cys His Tyr Arg Asn Gly Lys Arg Val Cys
1               5                   10                  15

Tyr Arg Arg Cys Asn
            20

<210> SEQ ID NO 329
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 329

Gly Phe Cys Trp Arg Val Cys Ser Tyr Arg Asn Gly Ala Arg Val Cys
1               5                   10                  15

Tyr Arg Arg Cys Asn
            20

<210> SEQ ID NO 330
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 330

Gly Phe Cys Trp Arg Val Cys Ser Tyr Arg Asn Gly Ser Arg Val Cys
1               5                   10                  15

Tyr Arg Arg Cys Asn
            20

<210> SEQ ID NO 331
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 331

Gly Phe Cys Trp Arg Val Cys Ser Tyr Arg Asn Gly Val Arg Lys Cys
1               5                   10                  15

Tyr Arg Arg Cys Asn
            20

<210> SEQ ID NO 332
<211> LENGTH: 21
<212> TYPE: PRT
```

```
<213> ORGANISM: Artificial
<220> FEATURE:
<223> OTHER INFORMATION: Synthetic antimicrobial peptide

<400> SEQUENCE: 332

Gly Phe Cys Trp Arg Val Cys Ser Arg Arg Asn Gly Val Arg Val Cys
1               5                   10                  15

Tyr Arg Arg Cys Asn
            20

<210> SEQ ID NO 333
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 333

Gly Phe Cys Trp Arg Val Cys Ser Ser Arg Asn Gly Val Arg Val Cys
1               5                   10                  15

Tyr Arg Arg Cys Asn
            20

<210> SEQ ID NO 334
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 334

Gly Phe Cys Trp Arg Val Cys Val Arg Arg Asn Gly Ala Arg Val Cys
1               5                   10                  15

Tyr Arg Arg Cys Asn
            20

<210> SEQ ID NO 335
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 335

Gly Phe Cys Trp Arg Val Cys Val Arg Arg Asn Gly Val Arg Val Cys
1               5                   10                  15

His Arg Arg Cys Asn
            20

<210> SEQ ID NO 336
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 336

Gly Phe Cys Trp Arg Val Cys Val Ser Arg Asn Gly Val Arg Val Cys
1               5                   10                  15

His Arg Arg Cys Asn
            20

<210> SEQ ID NO 337
<211> LENGTH: 21
```

```
<212> TYPE: PRT
<213> ORGANISM: Artificial
<220> FEATURE:
<223> OTHER INFORMATION: Synthetic antimicrobial peptide

<400> SEQUENCE: 337

Gly Phe Cys Trp Arg Val Cys Val Ser Arg Asn Gly Val Arg Val Cys
1               5                   10                  15

Ser Arg Arg Cys Asn
            20

<210> SEQ ID NO 338
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 338

Gly Phe Cys Trp Tyr Ala Cys Val Tyr Arg Asn Ser Lys Arg Val Cys
1               5                   10                  15

Tyr Arg Arg Cys Asn
            20

<210> SEQ ID NO 339
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 339

Gly Phe Cys Trp Tyr Ala Cys Val Tyr Arg Asn Gly Ala Arg Ser Cys
1               5                   10                  15

Tyr Arg Arg Cys Asn
            20

<210> SEQ ID NO 340
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 340

Gly Phe Cys Trp Tyr Ala Cys Val Tyr Arg Asn Gly Lys Arg Ala Cys
1               5                   10                  15

Tyr Arg Arg Cys Asn
            20

<210> SEQ ID NO 341
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 341

Gly Phe Cys Trp Tyr Ala Cys Val Tyr Arg Asn Gly Lys Arg Val Cys
1               5                   10                  15

His Arg Arg Cys Asn
            20

<210> SEQ ID NO 342
```

```
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 342

Gly Phe Cys Trp Tyr Ala Cys Val Tyr Arg Asn Gly Val Arg Lys Cys
1               5                   10                  15

His Arg Arg Cys Asn
            20

<210> SEQ ID NO 343
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 343

Gly Phe Cys Trp Tyr Ala Cys Ala Tyr Arg Asn Gly Val Arg Ala Cys
1               5                   10                  15

Tyr Arg Arg Cys Asn
            20

<210> SEQ ID NO 344
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 344

Gly Phe Cys Trp Tyr Arg Cys His Tyr Ser Asn Gly Val Arg Val Cys
1               5                   10                  15

Tyr Arg Arg Cys Asn
            20

<210> SEQ ID NO 345
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 345

Gly Phe Cys Trp Tyr Ser Cys Val Arg Arg Asn Gly Val Arg Ser Cys
1               5                   10                  15

Tyr Arg Arg Cys Asn
            20

<210> SEQ ID NO 346
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 346

Gly Phe Cys Trp Tyr Thr Cys Val Lys Arg Asn Gly Leu Arg Val Cys
1               5                   10                  15

Tyr Arg Arg Cys Asn
            20
```

```
<210> SEQ ID NO 347
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 347

Gly Phe Cys Trp Tyr Val Cys Ala Tyr Lys Asn Gly Val Arg Val Cys
1               5                   10                  15

His Arg Arg Cys Asn
            20

<210> SEQ ID NO 348
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 348

Gly Phe Cys Trp Tyr Val Cys Ala Tyr Arg Asn Gly Val Arg Ala Cys
1               5                   10                  15

His Arg Arg Cys Asn
            20

<210> SEQ ID NO 349
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 349

Gly Phe Cys Trp Tyr Val Cys Ala Tyr Arg Asn Gly Val Arg Ser Cys
1               5                   10                  15

His Arg Arg Cys Asn
            20

<210> SEQ ID NO 350
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 350

Gly Phe Cys Trp Tyr Val Cys Ala Arg Arg Asn Gly Ala Arg Val Cys
1               5                   10                  15

Tyr Arg Arg Cys Asn
            20

<210> SEQ ID NO 351
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 351

Gly Phe Cys Trp Tyr Val Cys Ala Arg Arg Asn Gly Val Arg Ser Cys
1               5                   10                  15

Tyr Arg Arg Cys Asn
            20
```

```
<210> SEQ ID NO 352
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 352

Gly Phe Cys Trp Tyr Val Cys Phe Tyr Arg Asn His Val Arg Val Cys
1               5                   10                  15

His Arg Arg Cys Asn
            20

<210> SEQ ID NO 353
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 353

Gly Phe Cys Trp Tyr Val Cys Val Phe Arg Asn Gly Val Arg Ala Cys
1               5                   10                  15

His Arg Arg Cys Asn
            20

<210> SEQ ID NO 354
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 354

Gly Phe Cys Trp Tyr Val Cys Val Lys Arg Asn Gly Ala Arg Val Cys
1               5                   10                  15

Ser Arg Arg Cys Asn
            20

<210> SEQ ID NO 355
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 355

Gly Phe Cys Trp Tyr Val Cys Val Arg Arg Asn Gly Val Arg Ser Cys
1               5                   10                  15

Ser Arg Arg Cys Asn
            20

<210> SEQ ID NO 356
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 356

Gly Phe Cys Trp Tyr Val Cys Val Tyr Lys Asn Gly Lys Arg Ser Cys
1               5                   10                  15

Tyr Arg Arg Cys Asn
            20
```

```
<210> SEQ ID NO 357
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 357

Gly Phe Cys Trp Tyr Val Cys Val Tyr Arg Asn Gly Lys Arg Ala Cys
1               5                   10                  15

His Arg Arg Cys Asn
            20

<210> SEQ ID NO 358
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 358

Arg Phe Cys Trp Asn Val Cys Val Tyr Arg His Gly Val Arg Val Cys
1               5                   10                  15

His Arg Arg Cys Asn
            20

<210> SEQ ID NO 359
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 359

Arg Phe Cys Trp Asn Val Cys Val Tyr Arg Asn Gly Val Arg Val Cys
1               5                   10                  15

His Arg His Cys Asn
            20

<210> SEQ ID NO 360
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 360

Gly Phe Cys Ala Tyr Ala Cys Val Lys Arg Asn Gly Ala Arg Val Cys
1               5                   10                  15

Tyr Arg Arg Cys Asn
            20

<210> SEQ ID NO 361
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 361

Gly Phe Cys Ala His Val Cys Val Tyr Arg Asn Gly Ala Arg Lys Cys
1               5                   10                  15

Tyr Arg Arg Cys Asn
```

```
                20

<210> SEQ ID NO 362
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 362

Gly Phe Cys Ala His Val Cys Val Lys Arg Asn Gly Ala Arg Val Cys
1               5                   10                  15

Tyr Arg Arg Cys Asn
            20

<210> SEQ ID NO 363
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 363

Gly Phe Cys Ala Arg Val Cys Ala Lys Arg Asn Gly Val Arg Val Cys
1               5                   10                  15

Tyr Arg Arg Cys Asn
            20

<210> SEQ ID NO 364
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 364

Gly Phe Cys Ala Arg Val Cys Val Lys Arg Asn Gly Val Arg Ser Cys
1               5                   10                  15

Tyr Arg Arg Cys Asn
            20

<210> SEQ ID NO 365
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 365

Gly Phe Cys Ala Arg Val Cys Val Arg Arg Asn Gly Val Arg Lys Cys
1               5                   10                  15

Tyr Arg Arg Cys Asn
            20

<210> SEQ ID NO 366
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 366

Gly Phe Cys Ala Arg Val Cys Val Arg Arg Asn Gly Val Arg Ser Cys
1               5                   10                  15
```

Tyr Arg Arg Cys Asn
            20

<210> SEQ ID NO 367
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 367

Gly Phe Cys Phe Tyr Ala Cys Val Arg Arg Asn Gly Val Arg Ser Cys
1               5                   10                  15

Tyr Arg Arg Cys Asn
            20

<210> SEQ ID NO 368
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 368

Gly Phe Cys Phe Tyr Val Cys Ala Ser Arg Asn Gly Val Arg Ser Cys
1               5                   10                  15

Tyr Arg Arg Cys Asn
            20

<210> SEQ ID NO 369
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 369

Gly Phe Cys Phe His Val Cys Ala Tyr Arg Asn Gly Val Arg Val Cys
1               5                   10                  15

His Arg Arg Cys Asn
            20

<210> SEQ ID NO 370
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 370

Gly Phe Cys Phe His Val Cys Ser Tyr Arg Asn Gly Val Arg Lys Cys
1               5                   10                  15

Tyr Arg Arg Cys Asn
            20

<210> SEQ ID NO 371
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 371

Gly Phe Cys Phe Asn Ala Cys Val Tyr Arg Asn Gly Val Arg Ser Cys
1               5                   10                  15

Tyr Arg Arg Cys Asn
            20

<210> SEQ ID NO 372
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 372

Gly Phe Cys Phe Asn Val Cys Ala Arg Arg Asn Gly Val Arg Val Cys
1               5                   10                  15

Tyr Arg Arg Cys Asn
            20

<210> SEQ ID NO 373
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 373

Gly Phe Cys Phe Arg Val Cys Val Tyr Arg Asn Gly Val Arg Lys Cys
1               5                   10                  15

His Arg Arg Cys Asn
            20

<210> SEQ ID NO 374
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 374

Gly Phe Cys Phe Arg Val Cys Val Tyr Arg Asn Gly Val Arg Ser Cys
1               5                   10                  15

Ser Arg Arg Cys Asn
            20

<210> SEQ ID NO 375
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 375

Gly Phe Cys Phe Arg Ala Cys Val Lys Arg Asn Gly Val Arg Val Cys
1               5                   10                  15

Tyr Arg Arg Cys Asn
            20

<210> SEQ ID NO 376
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 376

Gly Phe Cys Phe Arg Ser Cys Val Tyr Arg Asn Gly Ala Arg Val Cys

```
1               5                   10                  15
```
Tyr Arg Arg Cys Asn
            20

<210> SEQ ID NO 377
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 377

Gly Phe Cys Phe Arg Ser Cys Val Arg Asn Gly Val Arg Val Cys
1               5                   10                  15

Tyr Arg Arg Cys Asn
            20

<210> SEQ ID NO 378
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 378

Gly Phe Cys Phe Arg Val Cys Ala Tyr Arg Asn Gly Val Arg Lys Cys
1               5                   10                  15

Tyr Arg Arg Cys Asn
            20

<210> SEQ ID NO 379
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 379

Gly Phe Cys Phe Arg Val Cys Ala Tyr Arg Asn Gly Val Arg Val Cys
1               5                   10                  15

His Arg Arg Cys Asn
            20

<210> SEQ ID NO 380
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 380

Gly Phe Cys Phe Arg Val Cys Ala Ser Arg Asn Gly Val Arg Val Cys
1               5                   10                  15

Tyr Arg Arg Cys Asn
            20

<210> SEQ ID NO 381
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 381

```
Gly Phe Cys Phe Arg Val Cys Val Lys Arg Asn Gly Val Arg Lys Cys
1               5                   10                  15

Tyr Arg Arg Cys Asn
            20
```

<210> SEQ ID NO 382
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 382

```
Gly Phe Cys Phe Tyr Val Cys Val Arg Arg Asn Gly Val Arg Ser Cys
1               5                   10                  15

His Arg Arg Cys Asn
            20
```

<210> SEQ ID NO 383
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 383

```
Gly Phe Cys Gly His Val Cys Val Tyr Arg Asn Gly Val Arg Met Cys
1               5                   10                  15

Tyr Arg Arg Cys His
            20
```

<210> SEQ ID NO 384
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 384

```
Gly Phe Cys Gly Lys Val Cys Val Arg Arg Asn Gly Leu Arg Val Cys
1               5                   10                  15

Tyr Arg Arg Cys Asn
            20
```

<210> SEQ ID NO 385
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 385

```
Gly Phe Cys Gly Arg Val Cys Val Tyr Arg Asn Gly Lys Arg Ala Cys
1               5                   10                  15

Tyr Arg Arg Cys Asn
            20
```

<210> SEQ ID NO 386
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 386

```
Gly Phe Cys Gly Arg Val Cys Val Tyr Arg Asn Gly Lys Arg Ala Cys
1               5                   10                  15

Tyr Arg Arg Cys Asn
            20

<210> SEQ ID NO 387
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 387

Gly Phe Cys Gly Arg Val Cys Val Tyr Arg Asn Gly Lys Arg Ser Cys
1               5                   10                  15

Tyr Arg Arg Cys Asn
            20

<210> SEQ ID NO 388
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 388

Gly Phe Cys Gly Arg Val Cys Val Arg Arg Asn Gly Val Arg Lys Cys
1               5                   10                  15

Tyr Arg Arg Cys Asn
            20

<210> SEQ ID NO 389
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 389

Gly Phe Cys Thr Arg Val Cys Val Arg Arg Asn Gly Leu Arg Val Cys
1               5                   10                  15

Tyr Arg Arg Cys Asn
            20

<210> SEQ ID NO 390
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 390

Gly Phe Cys Trp His Val Cys Val Tyr Lys Asn Gly Lys Arg Ser Cys
1               5                   10                  15

Tyr Arg Arg Cys Asn
            20

<210> SEQ ID NO 391
<211> LENGTH: 21
<212> TYPE: PRT
<213> ORGANISM: Artificial
<220> FEATURE:
<223> OTHER INFORMATION: Synthetic antimicrobial peptide
```

```
<400> SEQUENCE: 391

Gly Phe Cys Trp His Ala Cys Val Arg Arg Asn Gly Val Arg Ser Cys
1               5                   10                  15

Tyr Arg Arg Cys Asn
            20

<210> SEQ ID NO 392
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 392

Gly Phe Cys Trp His Val Cys Ala Tyr Arg Asn Gly Lys Arg Ala Cys
1               5                   10                  15

Tyr Arg Arg Cys Asn
            20

<210> SEQ ID NO 393
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 393

Gly Phe Cys Trp His Val Cys Ala Lys Arg Asn Gly Leu Arg Val Cys
1               5                   10                  15

Tyr Arg Arg Cys Asn
            20

<210> SEQ ID NO 394
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 394

Gly Phe Cys Trp His Val Cys Ala Arg Arg Asn Gly Ala Arg Val Cys
1               5                   10                  15

Tyr Arg Arg Cys Asn
            20

<210> SEQ ID NO 395
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 395

Gly Phe Cys Trp His Val Cys Ala Arg Arg Asn Gly Val Arg Val Cys
1               5                   10                  15

His Arg Arg Cys Asn
            20

<210> SEQ ID NO 396
<211> LENGTH: 21
<212> TYPE: PRT
<213> ORGANISM: Artificial
<220> FEATURE:
<223> OTHER INFORMATION: Synthetic antimicrobial peptide
```

<400> SEQUENCE: 396

Gly Phe Cys Trp His Val Cys Ser Lys Arg Asn Gly Leu Arg Val Cys
1               5                   10                  15

Tyr Arg Arg Cys Asn
            20

<210> SEQ ID NO 397
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 397

Gly Phe Cys Trp His Val Cys Val Arg Arg Asn Gly Ala Arg Lys Cys
1               5                   10                  15

Tyr Arg Arg Cys Asn
            20

<210> SEQ ID NO 398
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 398

Gly Phe Cys Trp His Val Cys Val Arg Arg Asn Gly Ala Arg Ser Cys
1               5                   10                  15

Tyr Arg Arg Cys Asn
            20

<210> SEQ ID NO 399
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 399

Gly Phe Cys Trp His Val Cys Val Arg Arg Asn Gly Ala Arg Val Cys
1               5                   10                  15

Ser Arg Arg Cys Asn
            20

<210> SEQ ID NO 400
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 400

Gly Phe Cys Trp His Val Cys Val Ser Arg Asn Gly Leu Arg Lys Cys
1               5                   10                  15

Tyr Arg Arg Cys Asn
            20

<210> SEQ ID NO 401
<211> LENGTH: 21
<212> TYPE: PRT
<213> ORGANISM: Artificial
<220> FEATURE:

<223> OTHER INFORMATION: Synthetic antimicrobial peptide

<400> SEQUENCE: 401

Gly Phe Cys Trp Lys Ala Cys Val Tyr Lys Asn Gly Val Arg Val Cys
1               5                   10                  15

His Arg Arg Cys Asn
            20

<210> SEQ ID NO 402
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 402

Gly Phe Cys Trp Lys Ala Cys Val Tyr Arg Asn Gly Ala Arg Ser Cys
1               5                   10                  15

Tyr Arg Arg Cys Asn
            20

<210> SEQ ID NO 403
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 403

Gly Phe Cys Trp Lys Ala Cys Ala Tyr Arg Asn Gly Ala Arg Val Cys
1               5                   10                  15

Tyr Arg Arg Cys Asn
            20

<210> SEQ ID NO 404
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 404

Gly Phe Cys Trp Lys Val Cys Val Lys Arg Asn Gly Ala Arg Lys Cys
1               5                   10                  15

Tyr Arg Arg Cys Asn
            20

<210> SEQ ID NO 405
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 405

Gly Phe Cys Trp Lys Val Cys Val Arg Arg Asn Gly Ala Arg Val Cys
1               5                   10                  15

Ser Arg Arg Cys Asn
            20

<210> SEQ ID NO 406
<211> LENGTH: 21
<212> TYPE: PRT
<213> ORGANISM: Artificial

```
<220> FEATURE:
<223> OTHER INFORMATION: Synthetic antimicrobial peptide

<400> SEQUENCE: 406

Gly Phe Cys Trp Asn Ala Cys Ala Tyr Arg Asn Gly Lys Arg Val Cys
1               5                   10                  15

Tyr Arg Arg Cys Asn
            20

<210> SEQ ID NO 407
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 407

Gly Phe Cys Trp Asn Ala Cys Ala Arg Arg Asn Gly Val Arg Val Cys
1               5                   10                  15

Tyr Arg Arg Cys Asn
            20

<210> SEQ ID NO 408
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 408

Gly Phe Cys Trp Asn Ala Cys Val Arg Arg Asn Gly Val Arg Ser Cys
1               5                   10                  15

Tyr Arg Arg Cys Asn
            20

<210> SEQ ID NO 409
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 409

Gly Phe Cys Trp Asn Phe Cys Val Tyr Arg Tyr Gly Val Arg Val Cys
1               5                   10                  15

His Arg Arg Cys Asn
            20

<210> SEQ ID NO 410
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 410

Gly Phe Cys Trp Asn Val Cys Ala Tyr Arg Gln Gly Val Arg Val Cys
1               5                   10                  15

His Arg Arg Cys Asn
            20

<210> SEQ ID NO 411
<211> LENGTH: 21
<212> TYPE: PRT
```

<213> ORGANISM: Artificial
<220> FEATURE:
<223> OTHER INFORMATION: Synthetic antimicrobial peptide

<400> SEQUENCE: 411

Gly Phe Cys Trp Asn Val Cys Ala Tyr Arg Asn Gly Lys Arg Ala Cys
1               5                   10                  15

Tyr Arg Arg Cys Asn
            20

<210> SEQ ID NO 412
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 412

Gly Phe Cys Trp Asn Val Cys Val Arg Arg Asn Gly Ala Arg Ser Cys
1               5                   10                  15

Tyr Arg Arg Cys Asn
            20

<210> SEQ ID NO 413
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 413

Gly Phe Cys Trp Arg Val Cys Val Tyr Arg Asn Ser Lys Arg Val Cys
1               5                   10                  15

His Arg Arg Cys Asn
            20

<210> SEQ ID NO 414
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 414

Gly Phe Cys Trp Arg Val Cys Val Tyr Lys Asn Gly Lys Arg Val Cys
1               5                   10                  15

His Arg Arg Cys Asn
            20

<210> SEQ ID NO 415
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 415

Gly Phe Cys Trp Arg Ala Cys Val Tyr Arg Asn Gly Lys Arg Ser Cys
1               5                   10                  15

Tyr Arg Arg Cys Asn
            20

<210> SEQ ID NO 416
<211> LENGTH: 21

<212> TYPE: PRT
<213> ORGANISM: Artificial
<220> FEATURE:
<223> OTHER INFORMATION: Synthetic antimicrobial peptide

<400> SEQUENCE: 416

Gly Phe Cys Trp Arg Ala Cys Val Tyr Arg Asn Gly Val Arg Ala Cys
1               5                   10                  15

His Arg Arg Cys Asn
            20

<210> SEQ ID NO 417
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 417

Gly Phe Cys Trp Arg Ala Cys Ala Tyr Arg Asn Gly Lys Arg Val Cys
1               5                   10                  15

Tyr Arg Arg Cys Asn
            20

<210> SEQ ID NO 418
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 418

Gly Phe Cys Trp Arg Ala Cys Ala Tyr Arg Asn Gly Val Arg Ala Cys
1               5                   10                  15

Tyr Arg Arg Cys Asn
            20

<210> SEQ ID NO 419
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 419

Gly Phe Cys Trp Arg Ala Cys Ala Tyr Arg Asn Gly Val Arg Val Cys
1               5                   10                  15

His Arg Arg Cys Asn
            20

<210> SEQ ID NO 420
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 420

Gly Phe Cys Trp Arg Ala Cys Ala Arg Arg Asn Gly Val Arg Val Cys
1               5                   10                  15

Tyr Arg Arg Cys Asn
            20

<210> SEQ ID NO 421

<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 421

Gly Phe Cys Trp Arg Ala Cys His Tyr Arg Asn Gly Val Arg Ser Cys
1               5                   10                  15

Tyr Arg Arg Cys Asn
            20

<210> SEQ ID NO 422
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 422

Gly Phe Cys Trp Arg Ala Cys Val Arg Arg Asn Gly Val Arg Lys Cys
1               5                   10                  15

Tyr Arg Arg Cys Asn
            20

<210> SEQ ID NO 423
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 423

Gly Phe Cys Trp Arg Ser Cys Val Tyr Arg Asn Gly Ala Arg Ser Cys
1               5                   10                  15

Tyr Arg Arg Cys Asn
            20

<210> SEQ ID NO 424
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 424

Gly Phe Cys Trp Arg Val Cys Ala Tyr Arg Asn Ser Val Arg Ser Cys
1               5                   10                  15

Tyr Arg Arg Cys Asn
            20

<210> SEQ ID NO 425
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 425

Gly Phe Cys Trp Arg Val Cys Ala Tyr Ser Asn Gly Lys Arg Val Cys
1               5                   10                  15

Tyr Arg Arg Cys Asn
            20

```
<210> SEQ ID NO 426
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 426

Gly Phe Cys Trp Arg Val Cys Ala Tyr Arg Asn Gly Ala Arg Val Cys
1               5                   10                  15

His Arg Arg Cys Asn
            20

<210> SEQ ID NO 427
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 427

Gly Phe Cys Trp Arg Val Cys Ala Tyr Arg Asn Gly Lys Arg Ala Cys
1               5                   10                  15

Tyr Arg Arg Cys Asn
            20

<210> SEQ ID NO 428
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 428

Gly Phe Cys Trp Arg Val Cys Ala Tyr Arg Asn Gly Lys Arg Val Cys
1               5                   10                  15

His Arg Arg Cys Asn
            20

<210> SEQ ID NO 429
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 429

Gly Phe Cys Trp Arg Val Cys Ala Tyr Arg Asn Gly Val Arg Ala Cys
1               5                   10                  15

His Arg Arg Cys Asn
            20

<210> SEQ ID NO 430
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 430

Gly Phe Cys Trp Arg Val Cys Ala Tyr Arg Asn Gly Val Arg Ser Cys
1               5                   10                  15

His Arg Arg Cys Asn
            20
```

<210> SEQ ID NO 431
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 431

Gly Phe Cys Trp Arg Val Cys Ala Lys Arg Asn Gly Val Arg Lys Cys
1               5                   10                  15

Tyr Arg Arg Cys Asn
            20

<210> SEQ ID NO 432
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 432

Gly Phe Cys Trp Arg Val Cys Ala Lys Arg Asn Gly Val Arg Ser Cys
1               5                   10                  15

Tyr Arg Arg Cys Asn
            20

<210> SEQ ID NO 433
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 433

Gly Phe Cys Trp Arg Val Cys Ala Lys Arg Asn Gly Val Arg Val Cys
1               5                   10                  15

His Arg Arg Cys Asn
            20

<210> SEQ ID NO 434
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 434

Gly Phe Cys Trp Arg Val Cys Ala Arg Arg Asn Gly Val Arg Ser Cys
1               5                   10                  15

Tyr Arg Arg Cys Asn
            20

<210> SEQ ID NO 435
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 435

Gly Phe Cys Trp Arg Val Cys Ala Ser Arg Asn Gly Leu Arg Val Cys
1               5                   10                  15

Tyr Arg Arg Cys Asn
            20

```
<210> SEQ ID NO 436
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 436

Gly Phe Cys Trp Arg Val Cys Gly Tyr Arg Asn Ser Lys Arg Val Cys
1               5                   10                  15

Tyr Arg Arg Cys Asn
            20

<210> SEQ ID NO 437
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 437

Gly Phe Cys Trp Arg Val Cys His Tyr Arg Asn Ser Lys Arg Val Cys
1               5                   10                  15

Tyr Arg Arg Cys Asn
            20

<210> SEQ ID NO 438
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 438

Gly Phe Cys Trp Arg Val Cys His Tyr Lys Asn Gly Lys Arg Val Cys
1               5                   10                  15

Tyr Arg Arg Cys Asn
            20

<210> SEQ ID NO 439
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 439

Gly Phe Cys Trp Arg Val Cys His Tyr Ser Asn Gly Lys Arg Val Cys
1               5                   10                  15

Tyr Arg Arg Cys Asn
            20

<210> SEQ ID NO 440
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 440

Gly Phe Cys Trp Arg Val Cys Ser Lys Arg Asn Gly Val Arg Lys Cys
1               5                   10                  15

Tyr Arg Arg Cys Asn
```

```
                20

<210> SEQ ID NO 441
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 441

Gly Phe Cys Trp Arg Val Cys Val Lys Arg Asn Gly Ala Arg Lys Cys
1               5                   10                  15

Tyr Arg Arg Cys Asn
            20

<210> SEQ ID NO 442
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 442

Gly Phe Cys Trp Arg Val Cys Val Lys Arg Asn Gly Val Arg Ser Cys
1               5                   10                  15

Ser Arg Arg Cys Asn
            20

<210> SEQ ID NO 443
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 443

Gly Phe Cys Trp Arg Val Cys Val Arg Arg Asn Gly Ala Arg Lys Cys
1               5                   10                  15

Tyr Arg Arg Cys Asn
            20

<210> SEQ ID NO 444
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 444

Gly Phe Cys Trp Arg Val Cys Val Arg Arg Asn Gly Ala Arg Ser Cys
1               5                   10                  15

Tyr Arg Arg Cys Asn
            20

<210> SEQ ID NO 445
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 445

Gly Phe Cys Trp Arg Val Cys Val Arg Arg Asn Gly Leu Arg Lys Cys
1               5                   10                  15
```

```
Tyr Arg Arg Cys Asn
            20

<210> SEQ ID NO 446
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 446

Gly Phe Cys Trp Arg Val Cys Val Arg Arg Asn Gly Leu Arg Val Cys
1               5                   10                  15

His Arg Arg Cys Asn
            20

<210> SEQ ID NO 447
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 447

Gly Phe Cys Trp Arg Val Cys Val Arg Arg Asn Gly Val Arg Ser Cys
1               5                   10                  15

Ser Arg Arg Cys Asn
            20

<210> SEQ ID NO 448
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 448

Gly Phe Cys Trp Arg Val Cys Val Arg Arg Asn Gly Val Arg Val Cys
1               5                   10                  15

Ser Arg His Cys Asn
            20

<210> SEQ ID NO 449
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 449

Gly Phe Cys Trp Arg Val Cys Val Ser Arg Asn Gly Ala Arg Val Cys
1               5                   10                  15

Ser Arg Arg Cys Asn
            20

<210> SEQ ID NO 450
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 450

Gly Phe Cys Trp Tyr Ala Cys Ala Lys Arg Asn Gly Leu Arg Val Cys
1               5                   10                  15
```

Tyr Arg Arg Cys Asn
            20

<210> SEQ ID NO 451
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 451

Gly Phe Cys Trp Tyr Ala Cys Val Ser Arg Asn Gly Leu Arg Ser Cys
1               5                   10                  15

Tyr Arg Arg Cys Asn
            20

<210> SEQ ID NO 452
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 452

Gly Phe Cys Trp Tyr Val Cys Ala Tyr Ser Asn Gly Val Arg Ser Cys
1               5                   10                  15

His Arg Arg Cys Asn
            20

<210> SEQ ID NO 453
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 453

Gly Phe Cys Trp Tyr Val Cys Ala Arg Arg Asn Gly Leu Arg Ser Cys
1               5                   10                  15

Tyr Arg Arg Cys Asn
            20

<210> SEQ ID NO 454
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 454

Gly Phe Cys Trp Tyr Val Cys Val Lys Arg Asn Gly Ala Arg Lys Cys
1               5                   10                  15

His Arg Arg Cys Asn
            20

<210> SEQ ID NO 455
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 455

Gly Phe Cys Ala Arg Val Cys Val Lys Arg Asn Gly Ala Arg Lys Cys

```
1               5                   10                  15

Tyr Arg Arg Cys Asn
            20

<210> SEQ ID NO 456
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 456

Gly Phe Cys Ala Arg Val Cys Val Lys Arg Asn Gly Ala Arg Val Cys
1               5                   10                  15

His Arg Arg Cys Asn
            20

<210> SEQ ID NO 457
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 457

Gly Phe Cys Ala Arg Val Cys Val Ser Arg Asn Gly Leu Arg Lys Cys
1               5                   10                  15

Tyr Arg Arg Cys Asn
            20

<210> SEQ ID NO 458
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 458

Gly Phe Cys Ala Tyr Val Cys Val Ser Arg Asn Gly Ala Arg Ser Cys
1               5                   10                  15

His Arg Arg Cys Asn
            20

<210> SEQ ID NO 459
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 459

Gly Phe Cys Phe His Val Cys Ala Arg Arg Asn Gly Val Arg Lys Cys
1               5                   10                  15

Tyr Arg Arg Cys Asn
            20

<210> SEQ ID NO 460
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 460
```

```
Gly Phe Cys Phe His Val Cys Ala Arg Arg Asn Gly Val Arg Val Cys
1               5                   10                  15

His Arg Arg Cys Asn
            20
```

<210> SEQ ID NO 461
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 461

```
Gly Phe Cys Phe His Val Cys Val Lys Arg Asn Gly Val Arg Lys Cys
1               5                   10                  15

Ser Arg Arg Cys Asn
            20
```

<210> SEQ ID NO 462
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 462

```
Gly Phe Cys Phe Lys Val Cys Ser Tyr Arg Asn Gly Leu Arg Lys Cys
1               5                   10                  15

Tyr Arg Arg Cys Asn
            20
```

<210> SEQ ID NO 463
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 463

```
Gly Phe Cys Phe Lys Val Cys Ser Lys Arg Asn Gly Val Arg Lys Cys
1               5                   10                  15

Tyr Arg Arg Cys Asn
            20
```

<210> SEQ ID NO 464
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 464

```
Gly Phe Cys Phe Asn Val Cys Ala Arg Arg Asn Gly Val Arg Val Cys
1               5                   10                  15

Ser Arg Arg Cys Asn
            20
```

<210> SEQ ID NO 465
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 465

-continued

```
Gly Phe Cys Phe Arg Val Cys Val Tyr Arg Asn Gly Ala Arg Lys Cys
1               5                   10                  15

Ser Arg Arg Cys Asn
            20

<210> SEQ ID NO 466
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 466

Gly Phe Cys Phe Arg Ala Cys Ala Tyr Arg Asn Gly Val Arg Val Cys
1               5                   10                  15

His Arg Arg Cys Asn
            20

<210> SEQ ID NO 467
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 467

Gly Phe Cys Phe Arg Ala Cys Thr Ser Arg Asn Gly Val Arg Val Cys
1               5                   10                  15

Tyr Arg Arg Cys Asn
            20

<210> SEQ ID NO 468
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 468

Gly Phe Cys Phe Arg Ala Cys Val Lys Arg Asn Gly Ala Arg Val Cys
1               5                   10                  15

Tyr Arg Arg Cys Asn
            20

<210> SEQ ID NO 469
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 469

Gly Phe Cys Phe Arg Ala Cys Val Arg Arg Asn Gly Val Arg Val Cys
1               5                   10                  15

His Arg Arg Cys Asn
            20

<210> SEQ ID NO 470
<211> LENGTH: 21
<212> TYPE: PRT
<213> ORGANISM: Artificial
<220> FEATURE:
<223> OTHER INFORMATION: Synthetic antimicrobial peptide
```

```
<400> SEQUENCE: 470

Gly Phe Cys Phe Arg Ala Cys Val Ser Arg Asn Gly Val Arg Ser Cys
1               5                   10                  15

Tyr Arg Arg Cys Asn
            20

<210> SEQ ID NO 471
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 471

Gly Phe Cys Phe Arg Ser Cys Ala Arg Arg Asn Gly Val Arg Val Cys
1               5                   10                  15

Tyr Arg Arg Cys Asn
            20

<210> SEQ ID NO 472
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 472

Gly Phe Cys Phe Arg Ser Cys Ala Ser Arg Asn Gly Val Arg Val Cys
1               5                   10                  15

Tyr Arg Arg Cys Asn
            20

<210> SEQ ID NO 473
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 473

Gly Phe Cys Phe Arg Val Cys Ala Tyr Arg Asn Gly Ala Arg Ser Cys
1               5                   10                  15

Tyr Arg Arg Cys Asn
            20

<210> SEQ ID NO 474
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 474

Gly Phe Cys Phe Arg Val Cys Ala Tyr Arg Asn Gly Ala Arg Val Cys
1               5                   10                  15

His Arg Arg Cys Asn
            20

<210> SEQ ID NO 475
<211> LENGTH: 21
<212> TYPE: PRT
<213> ORGANISM: Artificial
<220> FEATURE:
<223> OTHER INFORMATION: Synthetic antimicrobial peptide
```

```
<400> SEQUENCE: 475

Gly Phe Cys Phe Arg Val Cys Ala Tyr Arg Asn Gly Ala Arg Val Cys
1               5                   10                  15

Ser Arg Arg Cys Asn
            20

<210> SEQ ID NO 476
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 476

Gly Phe Cys Phe Arg Val Cys Ala Tyr Arg Asn Gly Val Arg Lys Cys
1               5                   10                  15

His Arg Arg Cys Asn
            20

<210> SEQ ID NO 477
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 477

Gly Phe Cys Phe Arg Val Cys Ala Lys Arg Asn Gly Ala Arg Val Cys
1               5                   10                  15

Tyr Arg Arg Cys Asn
            20

<210> SEQ ID NO 478
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 478

Gly Phe Cys Phe Arg Val Cys Ala Lys Arg Asn Gly Val Arg Lys Cys
1               5                   10                  15

Tyr Arg Arg Cys Asn
            20

<210> SEQ ID NO 479
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 479

Gly Phe Cys Phe Arg Val Cys Ala Lys Arg Asn Gly Val Arg Val Cys
1               5                   10                  15

His Arg Arg Cys Asn
            20

<210> SEQ ID NO 480
<211> LENGTH: 21
<212> TYPE: PRT
<213> ORGANISM: Artificial
<220> FEATURE:
```

<223> OTHER INFORMATION: Synthetic antimicrobial peptide

<400> SEQUENCE: 480

Gly Phe Cys Phe Arg Val Cys Ala Ser Arg Asn Gly Val Arg Lys Cys
1               5                   10                  15

Tyr Arg Arg Cys Asn
            20

<210> SEQ ID NO 481
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 481

Gly Phe Cys Phe Arg Val Cys Ser Tyr Arg Asn Gly Ala Arg Ser Cys
1               5                   10                  15

Tyr Arg Arg Cys Asn
            20

<210> SEQ ID NO 482
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 482

Gly Phe Cys Phe Arg Val Cys Ser Tyr Arg Asn Gly Leu Arg Lys Cys
1               5                   10                  15

Tyr Arg Arg Cys Asn
            20

<210> SEQ ID NO 483
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 483

Gly Phe Cys Phe Arg Val Cys Ser Lys Arg Asn Gly Ala Arg Val Cys
1               5                   10                  15

Tyr Arg Arg Cys Asn
            20

<210> SEQ ID NO 484
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 484

Gly Phe Cys Phe Arg Val Cys Ser Lys Arg Asn Gly Val Arg Val Cys
1               5                   10                  15

His Arg Arg Cys Asn
            20

<210> SEQ ID NO 485
<211> LENGTH: 21
<212> TYPE: PRT
<213> ORGANISM: Artificial

```
<220> FEATURE:
<223> OTHER INFORMATION: Synthetic antimicrobial peptide

<400> SEQUENCE: 485

Gly Phe Cys Phe Arg Val Cys Ser Arg Arg Asn Gly Leu Arg Val Cys
1               5                   10                  15

Tyr Arg Arg Cys Asn
            20

<210> SEQ ID NO 486
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 486

Gly Phe Cys Phe Arg Val Cys Ser Ser Arg Asn Gly Ala Arg Val Cys
1               5                   10                  15

Tyr Arg Arg Cys Asn
            20

<210> SEQ ID NO 487
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 487

Gly Phe Cys Phe Arg Val Cys Ser Ser Arg Asn Gly Val Arg Lys Cys
1               5                   10                  15

Tyr Arg Arg Cys Asn
            20

<210> SEQ ID NO 488
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 488

Gly Phe Cys Phe Arg Val Cys Val Lys Arg Asn Gly Ala Arg Ser Cys
1               5                   10                  15

Tyr Arg Arg Cys Asn
            20

<210> SEQ ID NO 489
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 489

Gly Phe Cys Phe Arg Val Cys Val Arg Arg Asn Gly Val Arg Lys Cys
1               5                   10                  15

Ser Arg Arg Cys Asn
            20

<210> SEQ ID NO 490
<211> LENGTH: 21
<212> TYPE: PRT
```

-continued

```
<213> ORGANISM: Artificial
<220> FEATURE:
<223> OTHER INFORMATION: Synthetic antimicrobial peptide

<400> SEQUENCE: 490

Gly Phe Cys Phe Tyr Val Cys Val Ser Arg Asn Gly Ala Arg Lys Cys
1               5                   10                  15

His Arg Arg Cys Asn
            20

<210> SEQ ID NO 491
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 491

Gly Phe Cys Gly Lys Val Cys Val Lys Arg Asn Gly Leu Arg Lys Cys
1               5                   10                  15

Tyr Arg Arg Cys Asn
            20

<210> SEQ ID NO 492
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 492

Gly Phe Cys Gly Arg Val Cys Val Tyr Arg Asn Ser Lys Arg Ser Cys
1               5                   10                  15

Tyr Arg Arg Cys Asn
            20

<210> SEQ ID NO 493
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 493

Gly Phe Cys Gly Arg Val Cys Val Tyr Lys Asn Gly Lys Arg Ala Cys
1               5                   10                  15

Tyr Arg Arg Cys Asn
            20

<210> SEQ ID NO 494
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 494

Gly Phe Cys Ser Tyr Ser Cys Ala Tyr Arg Asn Gly Ser Arg Ser Cys
1               5                   10                  15

Tyr Arg Arg Cys Asn
            20

<210> SEQ ID NO 495
<211> LENGTH: 21
```

```
<212> TYPE: PRT
<213> ORGANISM: Artificial
<220> FEATURE:
<223> OTHER INFORMATION: Synthetic antimicrobial peptide

<400> SEQUENCE: 495

Gly Phe Cys Ser Asn Ser Cys Val Lys Arg Asn Gly Val Arg Val Cys
1               5                   10                  15

Ser Arg Arg Cys Asn
            20

<210> SEQ ID NO 496
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 496

Gly Phe Cys Thr Asn Val Cys Ala Lys Arg Asn Gly Ala Arg Val Cys
1               5                   10                  15

Tyr Arg Arg Cys Asn
            20

<210> SEQ ID NO 497
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 497

Gly Phe Cys Trp His Ala Cys Val Arg Arg Asn Gly Ala Arg Ser Cys
1               5                   10                  15

Tyr Arg Arg Cys Asn
            20

<210> SEQ ID NO 498
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 498

Gly Phe Cys Trp His Ala Cys Val Arg Arg Asn Gly Leu Arg Lys Cys
1               5                   10                  15

Tyr Arg Arg Cys Asn
            20

<210> SEQ ID NO 499
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 499

Gly Phe Cys Trp His Ala Cys Val Arg Arg Asn Gly Leu Arg Val Cys
1               5                   10                  15

His Arg Arg Cys Asn
            20

<210> SEQ ID NO 500
```

```
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 500

Gly Phe Cys Trp His Val Cys Ala Tyr Lys Asn Gly Val Arg Ala Cys
1               5                   10                  15

His Arg Arg Cys Asn
            20

<210> SEQ ID NO 501
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 501

Gly Phe Cys Trp His Val Cys Ala Arg Arg Asn Gly Leu Arg Val Cys
1               5                   10                  15

Ser Arg Arg Cys Asn
            20

<210> SEQ ID NO 502
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 502

Gly Phe Cys Trp Lys Arg Cys Val Tyr Arg Asn Gly Leu Arg Lys Cys
1               5                   10                  15

His Arg Arg Cys Asn
            20

<210> SEQ ID NO 503
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 503

Gly Phe Cys Trp Lys Ser Cys Val Arg Arg Asn Gly Leu Arg Ser Cys
1               5                   10                  15

Tyr Arg Arg Cys Asn
            20

<210> SEQ ID NO 504
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 504

Gly Phe Cys Trp Lys Val Cys Ala Arg Arg Asn Gly Ala Arg Ser Cys
1               5                   10                  15

Tyr Arg Arg Cys Asn
            20
```

```
<210> SEQ ID NO 505
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 505

Gly Phe Cys Trp Lys Val Cys Ser Ser Arg Asn Gly Leu Arg Ser Cys
1               5                   10                  15

Tyr Arg Arg Cys Asn
            20

<210> SEQ ID NO 506
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 506

Gly Phe Cys Trp Lys Val Cys Val Ser Arg Asn Gly Ala Arg Lys Cys
1               5                   10                  15

Ser Arg Arg Cys Asn
            20

<210> SEQ ID NO 507
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 507

Gly Phe Cys Trp Asn Val Cys Ala Arg Arg Asn Gly Leu Arg Val Cys
1               5                   10                  15

His Arg Arg Cys Asn
            20

<210> SEQ ID NO 508
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 508

Gly Phe Cys Trp Asn Val Cys Val Arg Arg Asn Gly Leu Arg Lys Cys
1               5                   10                  15

His Arg Arg Cys Asn
            20

<210> SEQ ID NO 509
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 509

Gly Phe Cys Trp Arg Val Cys Val Tyr Ser Asn Gly Lys Arg Ser Cys
1               5                   10                  15

His Arg Arg Cys Asn
            20
```

<210> SEQ ID NO 510
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 510

Gly Phe Cys Trp Arg Ala Cys Val Tyr Lys Asn Ser Lys Arg Val Cys
1               5                   10                  15

Tyr Arg Arg Cys Asn
            20

<210> SEQ ID NO 511
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 511

Gly Phe Cys Trp Arg Ala Cys Val Tyr Lys Asn Gly Val Arg Ala Cys
1               5                   10                  15

His Arg Arg Cys Asn
            20

<210> SEQ ID NO 512
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 512

Gly Phe Cys Trp Arg Ala Cys Ala Tyr Arg Asn Gly Lys Arg Ala Cys
1               5                   10                  15

Tyr Arg Arg Cys Asn
            20

<210> SEQ ID NO 513
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 513

Gly Phe Cys Trp Arg Ala Cys Ala Tyr Arg Asn Gly Lys Arg Ser Cys
1               5                   10                  15

Tyr Arg Arg Cys Asn
            20

<210> SEQ ID NO 514
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 514

Gly Phe Cys Trp Arg Ala Cys Ala Ser Arg Asn Gly Val Arg Val Cys
1               5                   10                  15

His Arg Arg Cys Asn
            20

<210> SEQ ID NO 515
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 515

Gly Phe Cys Trp Arg Ala Cys Ser Arg Arg Asn Gly Leu Arg Val Cys
1               5                   10                  15

Tyr Arg Arg Cys Asn
            20

<210> SEQ ID NO 516
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 516

Gly Phe Cys Trp Arg Ala Cys Val Lys Arg Asn Gly Ala Arg Val Cys
1               5                   10                  15

Ser Arg Arg Cys Asn
            20

<210> SEQ ID NO 517
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 517

Gly Phe Cys Trp Arg Ala Cys Val Lys Arg Asn Gly Leu Arg Ser Cys
1               5                   10                  15

Tyr Arg Arg Cys Asn
            20

<210> SEQ ID NO 518
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 518

Gly Phe Cys Trp Arg Ala Cys Val Arg Arg Asn Gly Ala Arg Ser Cys
1               5                   10                  15

Tyr Arg Arg Cys Asn
            20

<210> SEQ ID NO 519
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 519

Gly Phe Cys Trp Arg Ala Cys Val Arg Arg Asn Gly Leu Arg Ser Cys
1               5                   10                  15

Tyr Arg Arg Cys Asn

20

<210> SEQ ID NO 520
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 520

Gly Phe Cys Trp Arg Ala Cys Val Ser Arg Asn Gly Ala Arg Ser Cys
1               5                   10                  15

Tyr Arg Arg Cys Asn
            20

<210> SEQ ID NO 521
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 521

Gly Phe Cys Trp Arg Ala Cys Val Ser Arg Asn Gly Leu Arg Val Cys
1               5                   10                  15

Ser Arg Arg Cys Asn
            20

<210> SEQ ID NO 522
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 522

Gly Phe Cys Trp Arg Arg Cys Val Arg Arg Asn Gly Ala Arg Ser Cys
1               5                   10                  15

Tyr Arg Arg Cys Asn
            20

<210> SEQ ID NO 523
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 523

Gly Phe Cys Trp Arg Val Cys Ala Tyr Lys Asn Gly Lys Arg Ser Cys
1               5                   10                  15

Tyr Arg Arg Cys Asn
            20

<210> SEQ ID NO 524
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 524

Gly Phe Cys Trp Arg Val Cys Ala Arg Arg Asn Gly Leu Arg Val Cys
1               5                   10                  15

-continued

His Arg Arg Cys Asn
            20

<210> SEQ ID NO 525
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 525

Gly Phe Cys Trp Arg Val Cys Ala Ser Arg Asn Gly Ala Arg Val Cys
1               5                   10                  15

Ser Arg Arg Cys Asn
            20

<210> SEQ ID NO 526
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 526

Gly Phe Cys Trp Arg Val Cys Gly Tyr Lys Asn Gly Val Arg Ala Cys
1               5                   10                  15

His Arg Arg Cys Asn
            20

<210> SEQ ID NO 527
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 527

Gly Phe Cys Trp Arg Val Cys Gly Tyr Arg Asn Gly Lys Arg Ala Cys
1               5                   10                  15

His Arg Arg Cys Asn
            20

<210> SEQ ID NO 528
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 528

Gly Phe Cys Trp Arg Val Cys Ser Tyr Ser Asn Ser Lys Arg Val Cys
1               5                   10                  15

Tyr Arg Arg Cys Asn
            20

<210> SEQ ID NO 529
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 529

Gly Phe Cys Trp Arg Val Cys Ser Arg Arg Asn Gly Leu Arg Ser Cys
1               5                   10                  15

Tyr Arg Arg Cys Asn
            20

<210> SEQ ID NO 530
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 530

Gly Phe Cys Trp Arg Val Cys Val Arg Arg Asn Gly Leu Arg Ser Cys
1               5                   10                  15

Ser Arg Arg Cys Asn
            20

<210> SEQ ID NO 531
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 531

Gly Phe Cys Trp Arg Val Cys Val Ser Arg Asn Gly Ala Arg Lys Cys
1               5                   10                  15

Ser Arg Arg Cys Asn
            20

<210> SEQ ID NO 532
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 532

Gly Phe Cys Trp Arg Val Cys Val Ser Arg Asn Gly Leu Arg Ser Cys
1               5                   10                  15

Ser Arg Arg Cys Asn
            20

<210> SEQ ID NO 533
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 533

Gly Leu Cys Trp Arg Val Cys Ala Tyr Ser Asn Gly Lys Arg Ala Cys
1               5                   10                  15

Tyr Arg Arg Cys Asn
            20

<210> SEQ ID NO 534
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 534

Gly Phe Cys Phe Asn Val Cys Val Ser Arg Asn Gly Ala Arg Lys Cys

His Arg Arg Cys Asn
            20

<210> SEQ ID NO 535
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 535

Gly Phe Cys Phe Arg Ala Cys Ala Arg Arg Asn Gly Val Arg Ser Cys
1               5                   10                  15

Tyr Arg Arg Cys Asn
            20

<210> SEQ ID NO 536
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 536

Gly Phe Cys Phe Arg Ala Cys Ser Lys Arg Asn Gly Leu Arg Val Cys
1               5                   10                  15

Tyr Arg Arg Cys Asn
            20

<210> SEQ ID NO 537
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 537

Gly Phe Cys Phe Arg Ala Cys Val Lys Arg Asn Gly Leu Arg Lys Cys
1               5                   10                  15

Tyr Arg Arg Cys Asn
            20

<210> SEQ ID NO 538
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 538

Gly Phe Cys Phe Arg Ala Cys Val Lys Arg Asn Gly Leu Arg Val Cys
1               5                   10                  15

His Arg Arg Cys Asn
            20

<210> SEQ ID NO 539
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 539

Gly Phe Cys Phe Arg Val Cys Ala Lys Arg Asn Gly Ala Arg Ser Cys
1               5                   10                  15

Tyr Arg Arg Cys Asn
            20

<210> SEQ ID NO 540
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 540

Gly Phe Cys Phe Arg Val Cys Ala Ser Arg Asn Gly Val Arg Lys Cys
1               5                   10                  15

His Arg Arg Cys Asn
            20

<210> SEQ ID NO 541
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 541

Gly Phe Cys Phe Arg Val Cys Ser Lys Arg Asn Gly Ala Arg Lys Cys
1               5                   10                  15

Tyr Arg Arg Cys Asn
            20

<210> SEQ ID NO 542
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 542

Gly Phe Cys Gly His Arg Cys Ser Arg Arg Asn Gly Val Arg Lys Cys
1               5                   10                  15

Tyr Arg Arg Cys Asn
            20

<210> SEQ ID NO 543
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 543

Gly Phe Cys Ser His Arg Cys Ser Tyr Arg Asn Ser Val Arg Ala Cys
1               5                   10                  15

Tyr Arg Arg Cys Asn
            20

<210> SEQ ID NO 544
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 544

Gly Phe Cys Ser Arg Val Cys Ser Tyr Arg Asn Gly Ser Arg Ala Cys
1               5                   10                  15

His Arg Arg Cys Asn
            20

<210> SEQ ID NO 545
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 545

Gly Phe Cys Trp Arg Ala Cys Ala Ser Arg Asn Gly Leu Arg Val Cys
1               5                   10                  15

Ser Arg Arg Cys Asn
            20

<210> SEQ ID NO 546
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 546

Gly Phe Cys Ser Asn Arg Cys His Tyr Ser Asn Gly Ser Arg Ala Cys
1               5                   10                  15

His Arg Arg Cys Asn
            20

<210> SEQ ID NO 547
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 547

Gly Phe Cys Trp Gly Ala Val Asn Tyr Thr Ser Asn Cys Arg Ala Cys
1               5                   10                  15

Lys Arg Arg Cys Asn
            20

<210> SEQ ID NO 548
<211> LENGTH: 21
<212> TYPE: PRT
<213> ORGANISM: Artificial
<220> FEATURE:
<223> OTHER INFORMATION: Synthetic antimicrobial peptide

<400> SEQUENCE: 548

Gly Ser Cys Trp Gly Ala Val Asn Tyr Thr Ser Asn Cys Arg Ala Cys
1               5                   10                  15

Lys Arg Arg Cys Asn
            20